US011517598B2

(12) United States Patent
Selman et al.

(10) Patent No.: US 11,517,598 B2
(45) Date of Patent: Dec. 6, 2022

(54) COMPOSITIONS AND METHODS FOR ENHANCING GROWTH, SPREAD, AND ONCOLYTIC AND IMMUNOTHERAPEUTIC EFFICACY OF ONCOLYTIC RNA VIRUSES

(71) Applicant: Ottawa Hospital Research Institute, Ottawa (CA)

(72) Inventors: Mohammed Selman, Ottawa (CA); Jean-Simon Diallo, Ottawa (CA)

(73) Assignee: Ottawa Hospital Research Institute, Ottawa (CA)

( * ) Notice: Subject to any disclaimer, the term of this patent is extended or adjusted under 35 U.S.C. 154(b) by 917 days.

(21) Appl. No.: 16/339,294

(22) PCT Filed: Oct. 3, 2017

(86) PCT No.: PCT/CA2017/051176
§ 371 (c)(1),
(2) Date: Apr. 3, 2019

(87) PCT Pub. No.: WO2018/064762
PCT Pub. Date: Apr. 12, 2018

(65) Prior Publication Data
US 2019/0231832 A1    Aug. 1, 2019

Related U.S. Application Data

(60) Provisional application No. 62/403,586, filed on Oct. 3, 2016.

(51) Int. Cl.
*A61K 35/768* (2015.01)
*A61K 33/24* (2019.01)
(Continued)

(52) U.S. Cl.
CPC ............ *A61K 35/768* (2013.01); *A61K 33/24* (2013.01); *A61K 33/243* (2019.01); *A61K 35/76* (2013.01);
(Continued)

(58) Field of Classification Search
None
See application file for complete search history.

(56) References Cited

PUBLICATIONS

Extended European Search Report, EP 17857734.2, dated May 26, 2020.
(Continued)

*Primary Examiner* — Brian J Davis
(74) *Attorney, Agent, or Firm* — Bereskin & Parr LLP/S.E.N.C.R.L., s.r.l.; Dominique Lambert

(57) ABSTRACT

Provided herein are methods for enhancing infection, growth, spread, or titer of an oncolytic RNA virus in a cancer or tumor cell; enhancing the oncolytic activity, cytokine-induced cell death activity, and/or cytotoxic activity of an oncolytic RNA virus in a cancer or tumor cell; upregulating cytokine response to, and/or enhancing the immunotherapeutic activity of an oncolytic RNA virus in a cancer or tumor cell; and/or treating a tumor or cancer in a subject in need thereof. Such methods employ a vanadium-containing compound, administered to the cancer or tumor cells before, after, or concurrently with infection of the cancer or tumor cells with the oncolytic RNA virus. Related compositions, uses, and kits therefor are also provided. Methods for producing RNA viruses, RNA virus-based cancer vaccines, and RNA virus-based cancer gene therapy vectors are also provided.

21 Claims, 36 Drawing Sheets

Specification includes a Sequence Listing.

(51) Int. Cl.
*A61P 35/00* (2006.01)
*C12N 15/86* (2006.01)
*A61K 35/76* (2015.01)
*C12N 7/00* (2006.01)
*A61K 33/243* (2019.01)
*A61K 39/00* (2006.01)

(52) U.S. Cl.
CPC ............... *A61P 35/00* (2018.01); *C12N 7/00* (2013.01); *C12N 15/86* (2013.01); *A61K 2039/5254* (2013.01); *C12N 2760/20221* (2013.01); *C12N 2760/20232* (2013.01); *C12N 2760/20243* (2013.01); *C12N 2760/20271* (2013.01)

(56) References Cited

PUBLICATIONS

International Preliminary Report on Patentability, PCT/CA2017/051176, dated Apr. 18, 2019.
Arulanandam et al. Microtubule disruption synergizes with oncolytic virotherapy by inhibiting interferon translation and potentiating bystander killing. Nat Commun. 2015;6:6410. Published Mar. 30, 2015. doi:10.1038/ncomms7410.
Bergeron et al. Enhancement of oncolytic virotherapy by vanadium(V) dipicolinates. Biometals. 2019;32(3):545-561. doi:10.1007/s10534-019-00200-9.
Selman et al. Multi-modal Potentiation of Oncolytic Virotherapy by Vanadium Compounds. Mol Ther. 2018;26(1):56-69. doi:10.1016/j.ymthe.2017.10.014.
Yamamoto et al. Enhancement of Newcastle disease virus-induced fusion of mouse L cells by sodium vanadate. Microbiol Immunol. 1984;28(1):75-83. doi:10.1111/j.1348-0421.1984.tb02948.x.
International Search Report and Written Opinion for PCT/CA2017/051176, dated Jan. 9, 2018.
Bishayee et al., Vanadium in the detection, prevention and treatment of cancer: the in vivo evidence. Cancer Lett. Aug. 1, 2010;294(1):1-12. doi: 10.1016/j.canlet.2010.01.030. Epub Mar. 4, 2010.
Evangelou, Vanadium in cancer treatment. Crit Rev Oncol Hematol. Jun. 2002;42(3):249-65.
Novotny et al., Vanadium: Possible Use in Cancer Chemoprevention and Therapy. Journal of Cancer Research Updates 2014;42(3):97-102.

h

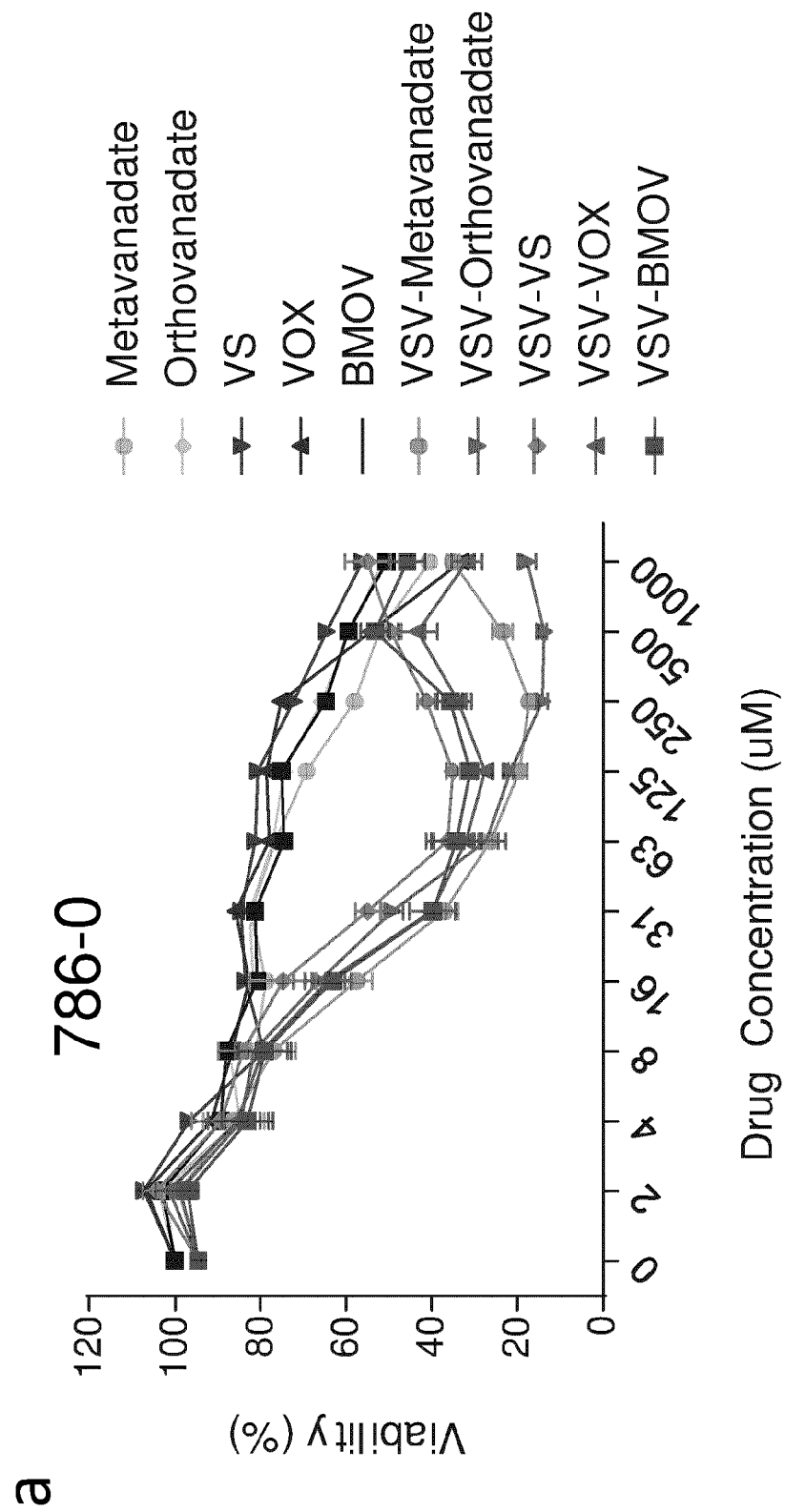

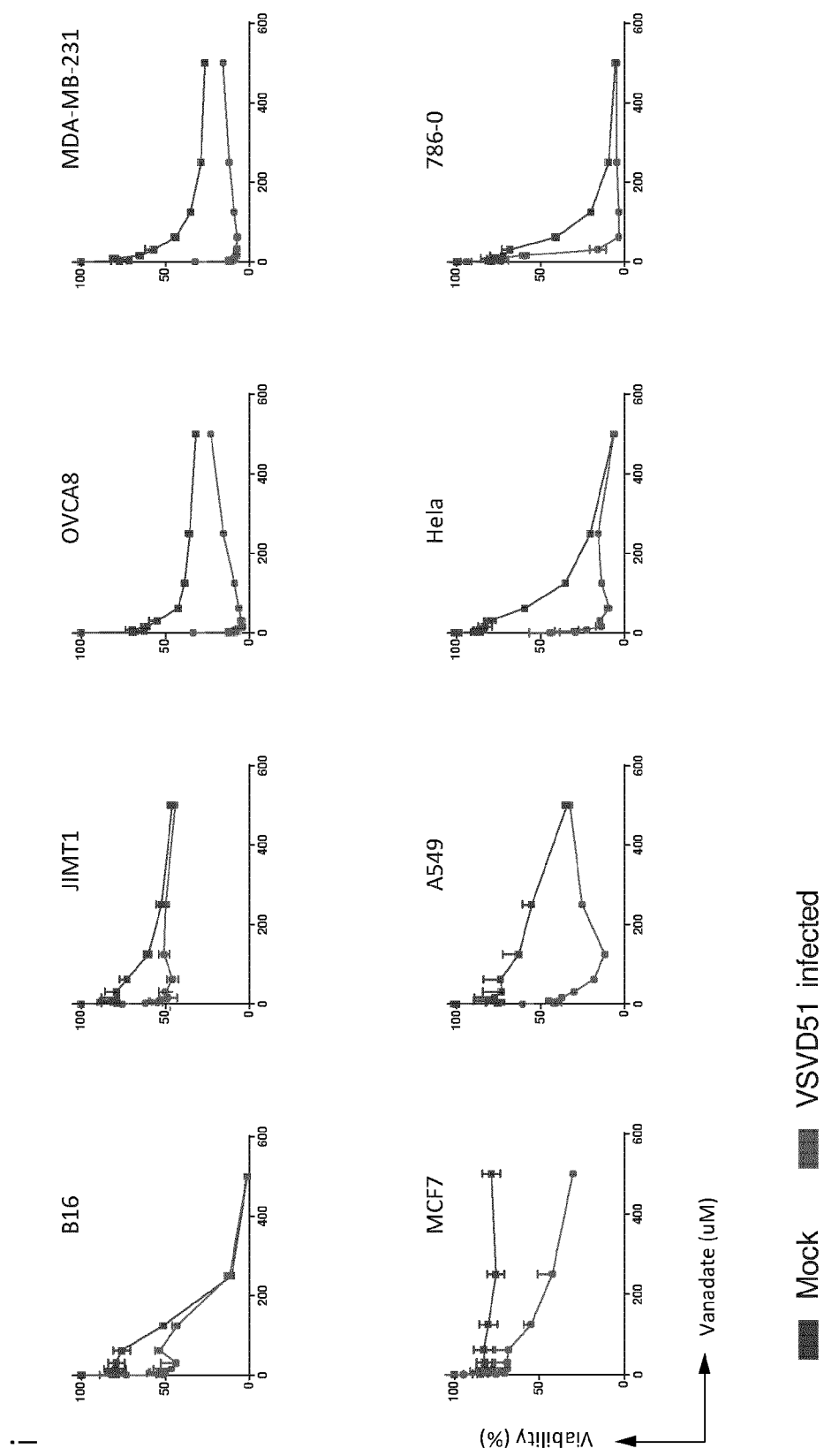

a f c d e

COMPOSITIONS AND METHODS FOR ENHANCING GROWTH, SPREAD, AND ONCOLYTIC AND IMMUNOTHERAPEUTIC EFFICACY OF ONCOLYTIC RNA VIRUSES

RELATED APPLICATIONS

This application is a national stage filing under 35 U.S.C. § 371 of international PCT application, PCT/CA2017/051176, filed Oct. 3, 2017, which claims priority under 35 U.S.C. § 119(e) to U.S. Provisional Application, U.S. Ser. No. 62/403,586, filed Oct. 3, 2016, each of which is incorporated herein by reference.

FIELD OF INVENTION

The present invention relates to compounds, methods, and compositions for enhancing oncolytic RNA virus activity in cancer or tumor cells.

BACKGROUND

Genetically attenuated viruses form the basis of a growing number of biotechnology and pharmaceutical platforms. Emerging in the field of cancer therapeutics, oncolytic virotherapy has shown significant promise over the last decade. A number of oncolytic viruses (OV) based on a wide range of viral backbones from small RNA viruses (eg. rhabdoviruses), to large DNA viruses (eg. poxviruses, herpesviruses) are currently being evaluated in clinical trials to treat a range of cancer types. Generating substantial excitement for this form of cancer therapy, approval of the first-in-class OV based on herpes-simplex virus-1 (HSV-1) for treatment of melanoma was granted by the FDA in 2015.

Oncolytic viruses (OVs) are, typically, self-amplifying biotherapeutic agents that have been selected or engineered to preferentially infect and kill cancer cells. When effective, OVs lead to tumor eradication not only by direct lysis of cancer cells but also through downstream generation of anti-cancer immune responses, vascular shutdown, and therapeutic transgene expression. As a basis for their selectivity, OVs exploit cellular defects that are inherent to the cancerous phenotype. This includes dysfunctional anti-viral responses and immune evasion, increased cell proliferation and metabolism, and leaky tumor vasculature. The biological environment ensuing from tumorigenesis is well suited to support the growth of genetically attenuated OVs that are otherwise harmless to normal cells.

OVs stand to be an attractive therapeutic modality for cancer because of their curative potential and their relatively mild side effects amounting to acute flu-like symptoms. However, heterogeneity in the clinical response to OVs remains a significant hurdle to overcome, as demonstrated in several human clinical trials. This heterogeneity in response may be attributed to factors that impede effective OV delivery and spread within tumors.

Although oncolytic viruses can and do work as single agents, numerous studies have shown that viral oncolysis, spread and overall efficacy is improved using pharmacological compounds which manipulate the cellular innate anti-viral immune response [2-4]. Beyond oncolytic effects on tumor cells, OVs can also boost antitumor immunity by directing immune responses to the tumor [5-8]. This immunostimulatory effect may be further enhanced by integrating immune stimulatory genes into the viral genome [7-10], such as T-VEC a herpes simplex virus type 1 based OV recently approved for treatment of melanoma by the US Food and Drug Administration (FDA) [11-13]. Combination of OVs and other forms of immunotherapy has now emerged as a promising approach in human patients [6-8].

Vanadate is an inhibitor of protein tyrosine phosphatases (PTPs) [14, 15], with a wide range of effects on several biological systems [16-20]. Interestingly, numerous studies suggest that vanadate has important effects on the immune system [21-23]. It exerts a stimulatory action on peripheral blood mononuclear cells and T cells [22, 24], enhances $Ca^{2+}$ signaling in T lymphocytes [25], causes spontaneous T-cell activation and secretion of interleukin-2 [26].

Vanadate and vanadium based compounds have been proposed for the treatment of several types of diseases. They are increasingly explored for their anti-diabetic potential, for which they been evaluated in various clinical trials [27-29]. In recent years, a number of vanadium based compound were found to exhibit anticancer effect, based on its apparent ability to inhibit cell proliferation, disrupt cellular metabolism, and alter organelles or spindle proteins [30-33].

While vanadate compounds have been widely studied for their insulin-mimetic effects, and are commonly used as general inhibitors of protein tyrosine phosphatases, their modulation of anticancer immunity has not been explored. Also, little is known about the effect of vanadate on viral infection, and what has been reported in the literature suggests that its effects may be virus dependent. For example, it has been suggested that vanadate can promote the shedding of latent HSV-1 [34], and promote virus-induced cell fusion of NDV (Newcastle disease virus) [35]. In sharp contrast, Vanadate was found to limit the fusion of paramyxovirus parainfluenza virus SV5 infected cells [36]. Hence the impact of vanadate on viral infection remains unclear and has been completely unexplored for many viruses.

Compounds and compositions that enhance virus growth, spread, and/or cytotoxicity are desired in the field. Compounds and compositions that enhance virotherapy-induced anti-tumor immune responses and/or that increase anti-cancer efficacy are also desired in the field. Improved or alternative methods for treating cancer cells in vitro and in vivo are also desired.

SUMMARY OF THE INVENTION

In certain embodiments, the present invention relates to compositions and methods which may enhance RNA virus infection, growth, titer, or spread and/or potentiate the oncolytic and/or immunotherapeutic activity of oncolytic RNA viruses.

Results described herein demonstrate a previously unreported effects of vanadium-containing compounds such as vanadate. In certain embodiments, vanadium-containing compounds are shown to enhance the growth and/or spread of replicating RNA viruses, and to increase oncolytic RNA viruses anti-cancer activity, likely by increasing cytokine-induced bystander killing of cancer cells and/or stimulating adaptive anti-cancer immunity in vivo.

In an embodiment, there is provided herein a method of enhancing or increasing the infection, spread, titer, or the oncolytic or immunotherapeutic activity of an oncolytic RNA virus in cancer or tumor cells, comprising administering a vanadium-containing compound to said cells prior to, after, or concurrently with infection of the cells with the virus.

In another embodiment, there is provided herein a method of enhancing, increasing or potentiating the infection, spread, titer, or the oncolytic or immunotherapeutic activity of an RNA virus in cancer or tumor cells, comprising administering one or more vanadium-containing compounds selected from:

Orthovanadate, Metavanadate, Vanadium (V) oxytriethoxyde (VOx), Vanadium (IV) oxide sulphate (VS) and bismaltolato oxovanadium (IV) (BMOV), Vanadium tetra-fluoride and Vanadium tri-bromide, to said cells prior to, after, or concurrently with infection of the cells with the virus.

In still another embodiment of any one of the method or methods described herein, the vanadium-containing compound or combination of compounds may be present in a composition comprising the compound(s) and a carrier, diluent or excipient.

In another embodiment, there is provided herein a composition comprising one or more of the vanadium-containing compounds, and one or more of a) an RNA virus, a genetically modified RNA virus, an attenuated RNA virus, an oncolytic RNA virus, an RNA virus-based cancer vaccine or cancer gene therapy vector, b) one or more cancer cells, c) a carrier, diluent or excipient, d) a pharmaceutically acceptable carrier, diluent or excipient, e) non-cancer cells; f) cell culture media; or g) one or more cancer therapeutics; or any combination of a)-g). The present invention also contemplates embodiments wherein any one or a combination of a-g) are specifically excluded from the composition or kit. Any component or group of components may be excluded if desired.

In yet another embodiment, there is provided herein a kit comprising one or more of the vanadium-containing compounds, and one or more of a) an RNA virus, a genetically modified RNA virus, an attenuated RNA virus, an oncolytic RNA virus, an RNA virus-based cancer vaccine or cancer gene therapy vector, b) one or more cancer cells, c) a pharmaceutically acceptable carrier, diluent or excipient, d) non-cancer cells; e) cell culture media; f) one or more cancer therapeutics, g) a cell culture plate or multi-well dish; h) an apparatus to deliver the compound to a cell, medium or to a subject; i) instructions for using the compound or any component in the kit, or j) a carrier diluent or excipient, or any combination of a)-j). The present invention also contemplates kits wherein any one or a combination thereof of a)-j) are specifically excluded.

In another embodiment, the cells may be cancer cells in vivo, or in vitro.

In a further embodiment, the in vivo cancer cells may be from a mammalian subject.

In still a further embodiment, the mammalian subject may be a human subject.

In yet another embodiment, there is provided herein a method of increasing the oncolytic activity of an oncolytic RNA virus in cancer or tumor cells, comprising administering a vanadium-containing compound, or a combination of vanadium containing compounds to said cancer or tumor cells prior to, concurrently with or after the oncolytic virus.

In another embodiment, there is provided herein a method of increasing the immunotherapeutic activity of an oncolytic RNA virus in cancer or tumor cells, comprising administering a vanadium-containing compound, or a combination of vanadium containing compounds to said cancer or tumor cells prior to, concurrently with or after the oncolytic virus.

In another embodiment, the cancer cells may be in vivo, or in vitro.

In still another embodiment, the in vivo cancer cells may be from a mammalian subject.

In yet another embodiment, the mammalian subject may be a human subject.

In another embodiment, there is provided herein a method of increasing the immunotherapeutic activity of an oncolytic RNA virus in cancer or tumor cells, comprising administering a vanadium-containing compound to a cancerous subject prior to, concurrently with or after the oncolytic virus.

In another embodiment, there is provided herein a use of vanadium-containing compounds in the manufacture of a medicament for enhancing or increasing the infection, spread, titer, cytotoxicity or immunotherapeutic activity of an oncolytic RNA virus in cancer or tumor cells.

In a further embodiment of any of the compositions, method or methods described above, the vanadium-containing compound is in a reduced or any of its oxidized state.

In yet another embodiment of any of the compositions, method or methods described above, the vanadium-containing compound may enhance RNA virus infection, growth or spread in infection-resistant cancer cells.

In yet another embodiment of any of compositions, method or methods described above, the vanadium-containing compound may enhance RNA virus infection, growth or spread in cancer cells and tumors in vivo without inducing virus spread to major organs.

In a further embodiment of any of compositions, method or methods described above, the vanadium-containing compound may enhance the virally induced cancer cell death in vivo, in vitro, or both.

In a further embodiment of any of compositions, method or methods described above, the vanadium-containing compound may potentiate the immunogenic response following RNA virus infection.

In an embodiment of any of the method or methods above, the oncolytic RNA virus may be any suitable oncolytic RNA virus known in the art which preferentially infects and lyses cancer or tumor cells as compared to non-cancer or normal cells. Examples of oncolytic RNA viruses known in the art which may be employed herein may include, without limitation, reovirus, newcastle disease virus, polio virus, mumps virus, measles virus, influenza virus, rhabdoviruses such as vesicular stomatitis virus and derivatives/variants thereof. In a preferred embodiment, the virus may be a Vesicular stomatitis virus (VSV), or a related rhabdovirus variant/derivative thereof for example, selected under specific growth conditions, one that has been subjected to a range of selection pressures, one that has been genetically modified using recombinant techniques known within the art, or a combination thereof. In another preferred embodiment, the virus may be VSVΔ51 (Stojdl et al., VSV strains with defects in their ability to shutdown innate immunity are potent systemic anti-cancer agents, Cancer Cell. 2003 October; 4(4):263-75, herein incorporated by reference). Other derivatives or variants may be based on viruses such as Maraba (MG-1, for example), Rabies, Rotavirus, Influenza, Hepatitis A, Mumps, Measles, Rubella, Reovirus, Dengue Virus, Chikungunya Virus, Respiratory Syncitial Virus, LCMV, lentivirus, or replicating retrovirus, for example.

In another embodiment of any of the method or methods above, the one or more types of cancer or tumor cells may be cancer or tumor cells in vitro or in vivo from any cell, cell line, tissue or organism, for example, but not limited to human, rat, mouse, cat, dog, pig, primate, horse and the like. In a preferred embodiment, the one or more cancer or tumor cells may comprise human cancer or tumor cells, for example, but not limited to lymphoblastic leukemia, myeloid leukemia, adrenocortical carcinoma, AIDS-related cancers, AIDS-related lymphoma, anal cancer, appendix cancer, astrocytoma, atypical teratoid/rhabdoid tumor, basal cell carcinoma, bile duct cancer, bladder cancer, bone cancer, osteosarcoma, malignant fibrous histiocytoma, brain stem glioma, brain tumor, cerebellar astrocytoma, cerebral astrocytoma/malignant glioma, craniopharyngioma, ependymoblastoma, medulloblastoma, pineal parenchymal tumors of intermediate differentiation, supratentorial primitive neuroectodermal tumors and pineoblastoma, visual pathway and hypothalamic glioma, spinal cord tumors, breast cancer, bronchial tumors, Burkitt lymphoma, carcinoid tumor, central nervous system lymphoma, cervical cancer, chordoma, chronic lymphocytic leukemia, chronic myelogenous leukemia, chronic myeloproliferative disorders, colon cancer, cutaneous T-Cell lymphoma, embryonal tumors, endometrial cancer, ependymoblastoma, ependymoma, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), gastrointestinal stromal cell tumor, germ cell tumors, extracranial, extragonadal, ovarian, gestational trophoblastic tumor, glioma, hairy cell leukemia, head and neck cancer, hepatocellular (Liver) cancer, histiocytosis, Langerhans cell cancer, Hodgkin lymphoma, hypopharyngeal cancer, islet cell tumors, Kaposi sarcoma, kidney cancer, laryngeal cancer, lymphocytic leukemia, hairy cell leukemia, lip and oral cavity cancer, liver cancer, non-small cell lung cancer, small cell lung cancer, Hodgkin lymphoma, non-Hodgkin lymphoma, malignant fibrous histiocytoma of bone and osteosarcoma, medulloblastoma, medulloepithelioma, melanoma, intraocular melanoma, Merkel cell carcinoma, mesothelioma, metastatic squamous neck cancer, mouth cancer, multiple endocrine neoplasia syndrome, multiple myeloma/plasma cell neoplasm, nasal cavity and paranasal sinus cancer, nasopharyngeal cancer, neuroblastoma, oral cancer, oropharyngeal cancer, ovarian cancer, pancreatic cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter cancer, transitional cell cancer, respiratory tract carcinoma, retinoblastoma, rhabdomyosarcoma, salivary gland cancer, uterine sarcoma, skin cancer, Merkel cell skin carcinoma, small intestine cancer, soft tissue sarcoma, squamous cell carcinoma, squamous neck cancer, stomach (Gastric) cancer, supratentorial primitive neuroectodermal tumors, T-Cell lymphoma, testicular cancer, throat cancer, thymoma and thymic carcinoma, thyroid cancer, trophoblastic tumor, urethral cancer, uterine cancer, endometrial cancer, uterine sarcoma, vaginal cancer, vulvar cancer, or Wilms tumor. However, the compounds and compositions described herein possible may be used to treat other cancers or tumor in vivo or in vitro.

In another embodiment, there is provided herein a composition comprising the vanadium-containing compound(s) as described herein, and an acceptable carrier, diluent or excipient. In a further embodiment, the carrier is a pharmaceutically acceptable carrier.

In another embodiment, there is provided herein a method of enhancing or increasing the infection, spread and/or titer, and/or cytotoxicity of a RNA virus in cells comprising, administering the vanadium-containing compound(s) as described herein to the cells prior to, after or concurrently with the RNA virus, and culturing the RNA virus and cells to enhance or increase the infection, spread and/or titer, or cytotoxicity of the RNA virus in said cells. Preferably, the cells comprise cancer cells, tumor cells or cells which have been immortalized. More preferably, the cells are in vivo cancer cells from a mammalian, still more preferably a human subject and the method is practiced in vivo.

Also provided is a method of enhancing or increasing the oncolytic activity of an oncolytic RNA virus in cancer cells comprising, administering the compound(s) as described herein to the cancer cells or subject prior to, concurrently with or after the oncolytic RNA virus and culturing the oncolytic RNA virus and cancer cells. In a further embodiment, the cancer cells are in vivo cancer cells. In a separate embodiment, the cancer cells are in vitro cancer cells. The cells may be from a mammalian subject, preferably a human subject.

In a particular embodiment, which is not meant to be limiting in any manner, there is provided a kit comprising a vanadium-containing compound and a medium for growing, culturing or infecting cells with a RNA virus and optionally, one or more cells which are capable of being infected by the virus. The kit may also comprise instructions for using any component or combination of components and/or practicing any method as described herein.

In another embodiment, there is provided herein a method of enhancing or increasing the infection, spread and/or titer, or oncolytic or immunotherapeutic activity of a RNA virus in cells comprising, administering the vanadium-containing compound as described herein to the cells prior to, after or concurrently with the virus. The method is preferably practiced in vivo but in vitro applications are also contemplated.

In another embodiment, there is provided herein a method of enhancing or increasing the spread of an oncolytic RNA virus in tumor or cancer cells comprising, administering the compound as described above to the cancer or tumor cells prior to, after or concurrently with the oncolytic virus. The cancer or tumor cells may be in vivo, or in vitro, preferably in vivo from a mammalian subject such as, but not limited to, a human subject.

Also provided is a method of enhancing or increasing the oncolytic activity of an oncolytic RNA virus in cancer or tumor cells comprising, administering the compound as described above to the cancer or tumor cells prior to, concurrently with or after the oncolytic RNA virus. The cancer or tumor cells may be in vivo, or in vitro, preferably from a mammalian subject such as, but not limited to a human subject.

In yet another embodiment, there is provided herein a method of producing a RNA virus by growing the virus in an appropriate medium in the presence of the vanadium-containing compound as described above.

In still another embodiment, there is provided herein a method of producing an attenuated RNA virus by growing the virus in an appropriate medium in the presence of the vanadium-containing compound as described above.

In yet another embodiment, there is provided herein a method of producing a genetically modified RNA virus by growing the virus in an appropriate medium in the presence of the vanadium-containing compound as described above.

In another embodiment, there is provided herein a method of producing an oncolytic RNA virus by growing the virus in an appropriate medium in the presence of the vanadium-containing compound as described above.

In still another embodiment, there is provided herein a method of producing a RNA virus-based cancer vaccine by growing the virus in an appropriate medium in the presence of the vanadium-containing compound as described above.

In yet another embodiment, there is provided herein a method of producing a RNA virus-based cancer gene therapy vector by growing the virus in an appropriate medium in the presence of the vanadium-containing compound as described above.

In another embodiment, there is provided herein a method for enhancing infection, growth, spread, or titer of an oncolytic RNA virus in a cancer or tumor cell, said method comprising:
  administering a vanadium-containing compound to the cancer or tumor cell before, after, or concurrently with infection of the cancer or tumor cell with the oncolytic RNA virus.

In another embodiment, there is provided herein a method for enhancing the oncolytic activity, cytokine-induced cell death activity, and/or cytotoxic activity of an oncolytic RNA virus in a cancer or tumor cell, said method comprising:
  administering a vanadium-containing compound to the cancer or tumor cell before, after, or concurrently with infection of the cancer or tumor cell with the oncolytic RNA virus.

In yet another embodiment, there is provided herein a method for potentiating immune response to, upregulating cytokine response to, and/or enhancing the immunotherapeutic activity of an oncolytic RNA virus in a cancer or tumor cell, said method comprising:
  administering a vanadium-containing compound to the cancer or tumor cell before, after, or concurrently with infection of the cancer or tumor cell with the oncolytic RNA virus.

In still another embodiment, there is provided herein a method for treating a tumor or cancer in a subject in need thereof, said method comprising:
  administering a vanadium-containing compound to the subject before, after, or concurrently with administering an oncolytic RNA virus to the subject.

In another embodiment, there is provided herein a use of a vanadium-containing compound for enhancing infection, growth, spread, or titer of an oncolytic RNA virus in a cancer or tumor cell.

In yet another embodiment, there is provided herein a use of a vanadium-containing compound for enhancing the oncolytic activity, cytokine-induced cell death activity, and/or cytotoxic activity of an oncolytic RNA virus in a cancer or tumor cell.

In still another embodiment, there is provided herein a use of a vanadium-containing compound for potentiating immune response to, upregulating cytokine response to, and/or enhancing the immunotherapeutic activity of an oncolytic RNA virus in a cancer or tumor cell.

In another embodiment, there is provided herein a use of a vanadium-containing compound in combination with an oncolytic RNA virus for treating a tumor or cancer in a subject in need thereof, wherein said vanadium-containing compound is for administration to the subject before, after, or concurrently with the oncolytic RNA virus.

In another embodiment, there is provided herein a use of a vanadium-containing compound in the manufacture of a medicament for enhancing infection, growth, spread, or titer of an oncolytic RNA virus in a cancer or tumor cell.

In yet another embodiment, there is provided herein a use of a vanadium-containing compound in the manufacture of a medicament for enhancing the oncolytic activity, cytokine-induced cell death activity, and/or cytotoxic activity of an oncolytic RNA virus in a cancer or tumor cell.

In still another embodiment, there is provided herein a use of a vanadium-containing compound in the manufacture of a medicament for potentiating immune response to, upregulating cytokine response to, and/or enhancing the immunotherapeutic activity of an oncolytic RNA virus in a cancer or tumor cell.

In another embodiment, there is provided herein a use of a vanadium-containing compound in the manufacture of a medicament for use in combination with an oncolytic RNA virus for treating a tumor or cancer in a subject in need thereof, wherein said medicament is for administration to the subject before, after, or concurrently with the oncolytic RNA virus.

In another embodiment, there is provided herein a use of a vanadium-containing compound and an oncolytic RNA virus in the manufacture of a medicament for treating a tumor or cancer in a subject in need thereof.

In another embodiment, there is provided herein a vanadium-containing compound for use in enhancing infection, growth, spread, or titer of an oncolytic RNA virus in a cancer or tumor cell.

In yet another embodiment, there is provided herein a vanadium-containing compound for use in enhancing the oncolytic activity, cytokine-induced cell death activity, and/or cytotoxic activity of an oncolytic RNA virus in a cancer or tumor cell.

In still another embodiment, there is provided herein a vanadium-containing compound for use in potentiating immune response to, upregulating cytokine response to, and/or enhancing the immunotherapeutic activity of an oncolytic RNA virus in a cancer or tumor cell.

In another embodiment, there is provided herein a vanadium-containing compound for use in combination with an oncolytic RNA virus for treating a tumor or cancer in a subject in need thereof, wherein said vanadium-containing compound is for administration to the subject before, after, or concurrently with the oncolytic RNA virus.

In another embodiment, there is provided herein a composition comprising a vanadium-containing compound and an oncolytic RNA virus.

In another embodiment, there is provided herein a kit comprising an oncolytic RNA virus and a vanadium-containing compound.

In another embodiment of any of the methods or uses above, the Vanadium-containing compound may comprise Orthovanadate, Metavanadate, Vanadium (V) oxytriethoxyde (VOx), Vanadium (IV) oxide sulphate (VS) and bismaltolato oxovanadium (IV) (BMOV), Vanadium tetrafluoride and Vanadium tri-bromide, or a pharmaceutically acceptable salt, solvate, hydrate, reduced, or oxidized form thereof.

In another embodiment of any of the methods or uses above, the oncolytic RNA virus may comprise a reovirus, newcastle disease virus, polio virus, mumps virus, measles virus, influenza virus, Maraba virus (such as MG-1), Rabies virus, Rotavirus, Hepatitis A virus, Rubella virus, Dengue virus, Chikungunya virus, Respiratory Syncitial Virus, LCMV, lentivirus, replicating retrovirus, or rhabdovirus, or a variant or derivative thereof.

In another embodiment of any of the methods or uses above, the RNA virus may comprise a rhabdovirus which is vesicular stomatitis virus or a derivative or variant thereof.

In yet another embodiment of any of the methods or uses above, the RNA virus may comprise a virus selected under specific growth conditions, subjected to one or more selection pressures, genetically modified using a recombinant technique, or any combination thereof.

In another embodiment of any of the methods or uses above, the cell or subject may be mammalian.

In yet another embodiment of any of the methods or uses above, the cell or subject may be human.

In still another embodiment of any of the methods or uses above, the cancer or tumor may comprise lymphoblastic leukemia, myeloid leukemia, adrenocortical carcinoma, AIDS-related cancer, AIDS-related lymphoma, anal cancer, appendix cancer, astrocytoma, atypical teratoid/rhabdoid tumor, basal cell carcinoma, bile duct cancer, bladder cancer, bone cancer, osteosarcoma, malignant fibrous histiocytoma, brain stem glioma, brain tumor, cerebellar astrocytoma, cerebral astrocytoma/malignant glioma, craniopharyngioma, ependymoblastoma, medulloblastoma, pineal parenchymal tumors of intermediate differentiation, supratentorial primitive neuroectodermal tumors and pineoblastoma, visual pathway and hypothalamic glioma, spinal cord tumors, breast cancer, bronchial tumors, Burkitt lymphoma, carcinoid tumor, central nervous system lymphoma, cervical cancer, chordoma, chronic lymphocytic leukemia, chronic myelogenous leukemia, chronic myeloproliferative disorders, colon cancer, cutaneous T-Cell lymphoma, embryonal tumors, endometrial cancer, ependymoblastoma, ependymoma, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), gastrointestinal stromal cell tumor, germ cell tumors, extracranial, extragonadal, ovarian, gestational trophoblastic tumor, glioma, hairy cell leukemia, head and neck cancer, hepatocellular (Liver) cancer, histiocytosis, Langerhans cell cancer, Hodgkin lymphoma, hypopharyngeal cancer, islet cell tumors, Kaposi sarcoma, kidney cancer, laryngeal cancer, lymphocytic leukemia, hairy cell leukemia, lip and oral cavity cancer, liver cancer, non-small cell lung cancer, small cell lung cancer, Hodgkin lymphoma, non-Hodgkin lymphoma, malignant fibrous histiocytoma of bone and osteosarcoma, medulloblastoma, medulloepithelioma, melanoma, intraocular melanoma, Merkel cell carcinoma, mesothelioma, metastatic squamous neck cancer, mouth cancer, multiple endocrine neoplasia syndrome, multiple myeloma/plasma cell neoplasm, nasal cavity and paranasal sinus cancer, nasopharyngeal cancer, neuroblastoma, oral cancer, oropharyngeal cancer, ovarian cancer, pancreatic cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter cancer, transitional cell cancer, respiratory tract carcinoma, retinoblastoma, rhabdomyosarcoma, salivary gland cancer, uterine sarcoma, skin cancer, Merkel cell skin carcinoma, small intestine cancer, soft tissue sarcoma, squamous cell carcinoma, squamous neck cancer, stomach (Gastric) cancer, supratentorial primitive neuroectodermal tumors, T-Cell lymphoma, testicular cancer, throat cancer, thymoma and thymic carcinoma, thyroid cancer, trophoblastic tumor, urethral cancer, uterine cancer, endometrial cancer, uterine sarcoma, vaginal cancer, vulvar cancer, or Wilms tumor.

In yet another embodiment, there is provided herein a method for producing an RNA virus comprising:
culturing a cancer or tumor cell infected with the RNA virus in an appropriate medium in the presence of a vanadium-containing compound; and
producing the RNA virus from the cancer or tumor cell via viral replication.

In another embodiment of the above method, the RNA virus may be an attenuated RNA virus, a genetically modified RNA virus, or an oncolytic RNA virus.

In yet another embodiment, there is provided herein a method for producing an RNA virus-based cancer vaccine comprising:
culturing a cancer or tumor cell infected with an RNA virus in an appropriate medium in the presence of a vanadium-containing compound;
producing the RNA virus from the cancer or tumor cell via viral replication; and
preparing the RNA virus-based cancer vaccine from the produced RNA virus.

In still another embodiment, there is provided herein a method for producing an RNA virus-based cancer gene therapy vector comprising:
culturing a cancer or tumor cell infected with an RNA virus in an appropriate medium in the presence of a vanadium-containing compound;
producing the RNA virus from the cancer or tumor cell via viral replication; and
preparing the RNA virus-based cancer gene therapy vector from the produced RNA virus.

In another embodiment of any of the methods, uses, kits, or compositions above, the RNA virus may be VSVΔ51.

In another embodiment of any of the methods, uses, kits, or compositions above, the vanadium-containing compound may be a vanadate.

In still another embodiment of any of the methods, uses, kits, or compositions above, the vanadium-containing compound may be a pharmaceutically acceptable salt of orthovanadate.

The present invention will be better understood with reference to the following description and accompanying drawings.

BRIEF DESCRIPTION OF THE DRAWINGS

These and other features of the invention will become more apparent from the following description in which reference is made to the appended drawings wherein.

DETAILED DESCRIPTION

Figure 1:
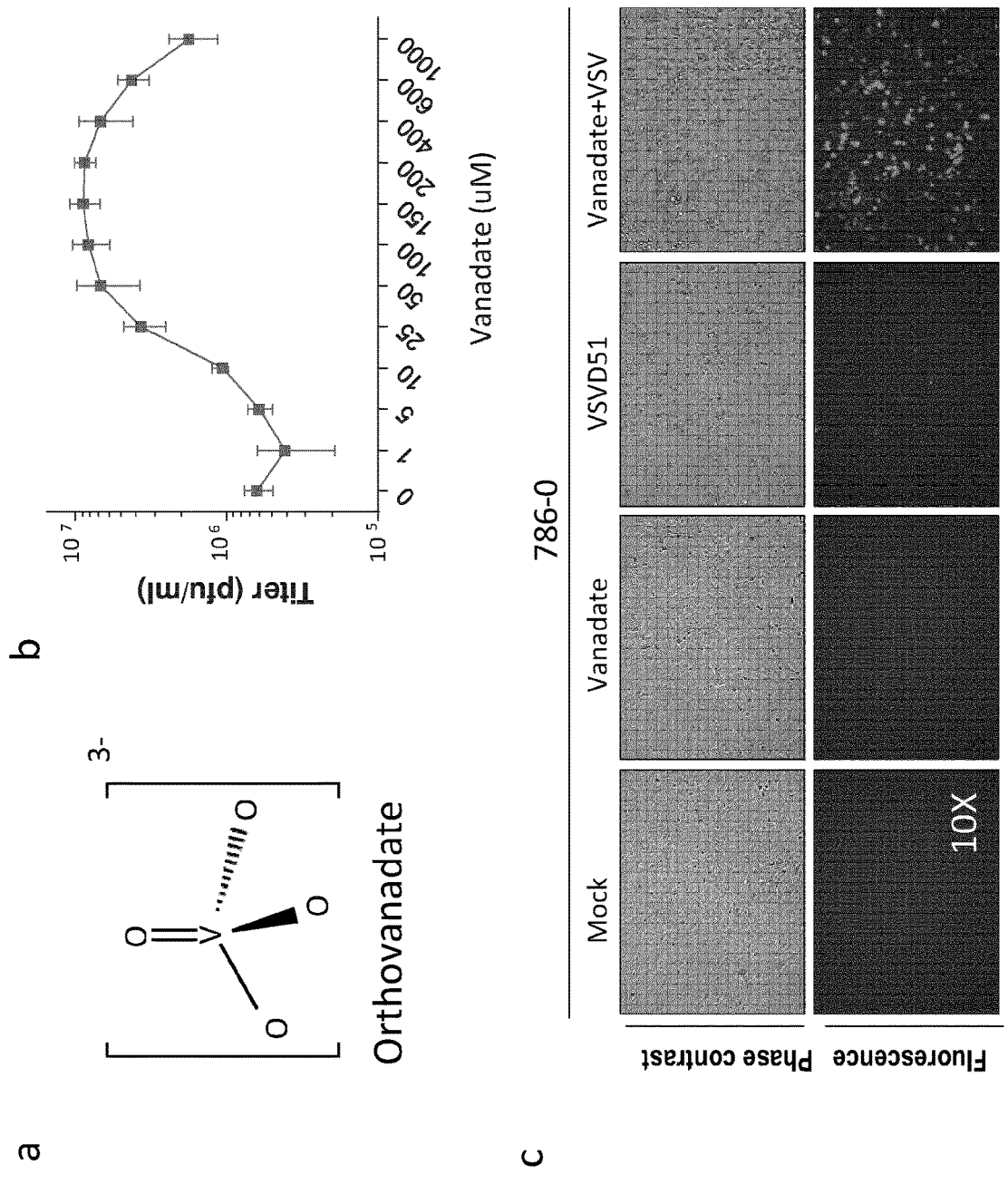
FIG. 1 shows results in which vanadate enhanced RNA virus infection in cancer cells but not in normal cells. (a) Structure of orthovanadate ion. (b, c) Resistance human renal cancer cell lines 786-0 were pretreated with dose range of orthovanadate for 4 hours and subsequently infected with oncolytic VSVΔ51 expressing GFP at an MOI of 0.01. (b) Corresponding viral titer were determined 24 hours post infection from supernatants (N=3). (c) 24 hours post infection fluorescent and phase contrast images were taken of the 786-0 cells mock treated or 200 uM of orthovanadate. (d) Multi-step, and (e) single-step growth curve of 786-0 pretreated with orthovanadate and infected with VSVΔ51 (d) MOI: 0.01 or (e) MOI: 0.01, supernatants were titred by plaque assay. (f) 786-0 cells treated with 200 uM of orthovanadate at various time pre or post infection with VSVΔ51 (MOI: 0.01), supernatants were collected 24 hours post infect, and titred by plaque assay. Black dotted line represents titer value for infected, untreated 786-0 cells. (i) 786-0 were pretreated with dose range of orthovanadate for 4 hours and subsequently infected with VSVΔ51 (MOI: 0.01), VSVwt (MOI: 0.01), Measles (MOI: 0.01), Sindbis (MOI: 10) or HSV (MOI: 0.01). Corresponding viral titer were determined 24 (VSVΔ51, VSVwt) or 48 (Measles, Sindbis, HSV) hours post infection from supernatants (N=3). (k) Normal cell line GM38 were pretreated with dose range of orthovanadate for 4 hours and subsequently infected with oncolytic VSVΔ51 expressing GFP at an MOI of 0.01. Corresponding viral titer were determined 24 hours post infection from supernatants (N=3), and corresponding fluorescent images was taken. (g) 24 hours post infection, RNA was collect from 786-0 and CT26WT, and expression of VSV-M gene was quantified by qPCR. (h) CT26 wt and DBT tumors were grown subcutaneously in Balb/c mice and excised when the tumor reached 10 mm×10 mm and subsequently cored. Balb/c mice spleen, muscle, lung, and brain tissue were also collected, and cored. Tumor and normal tissue cores were pretreated with 300 uM of orthovanadate for 4 hours and subsequently infected with 1×10$^4$ PFU of oncolytic VSVΔ51 expressing GFP. 24 hours post infection fluorescent images were acquired of the tumor and normal tissue cores. Representative images from each triplicate set are shown.
Figure 1:
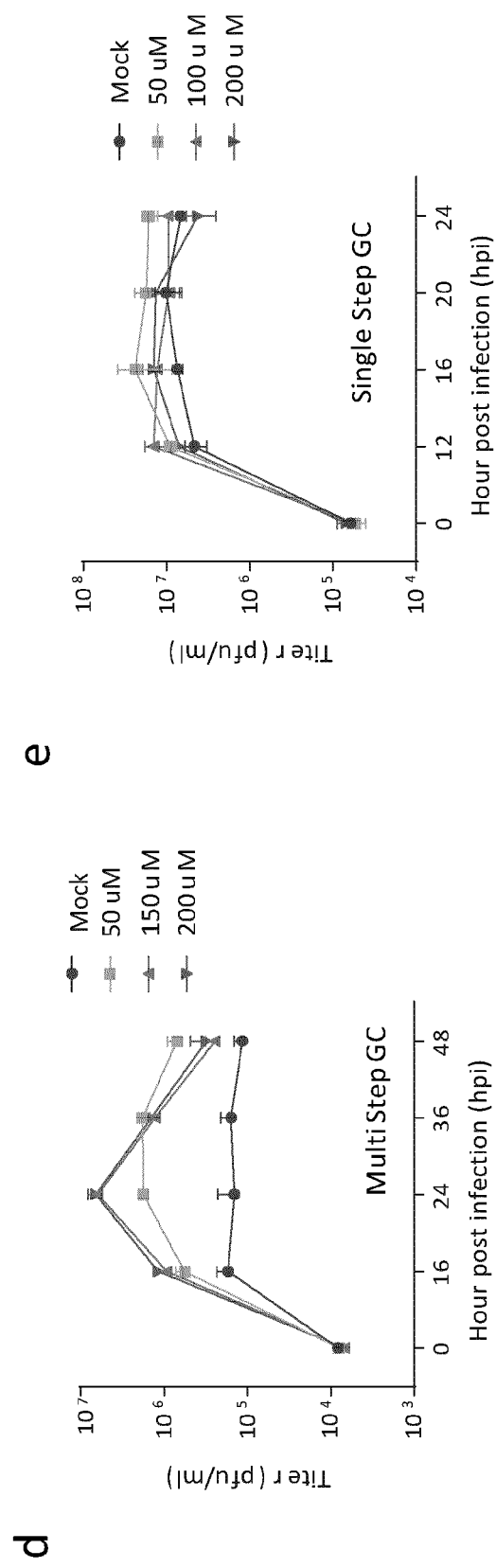
Figure 1:
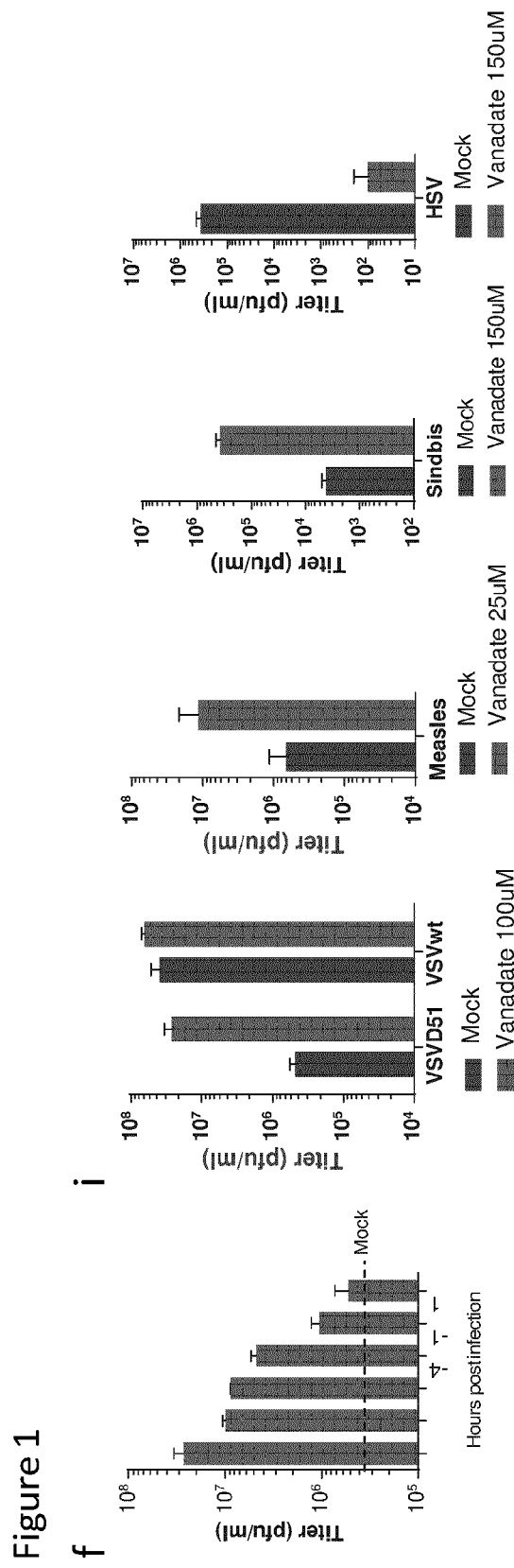
Figure 1:
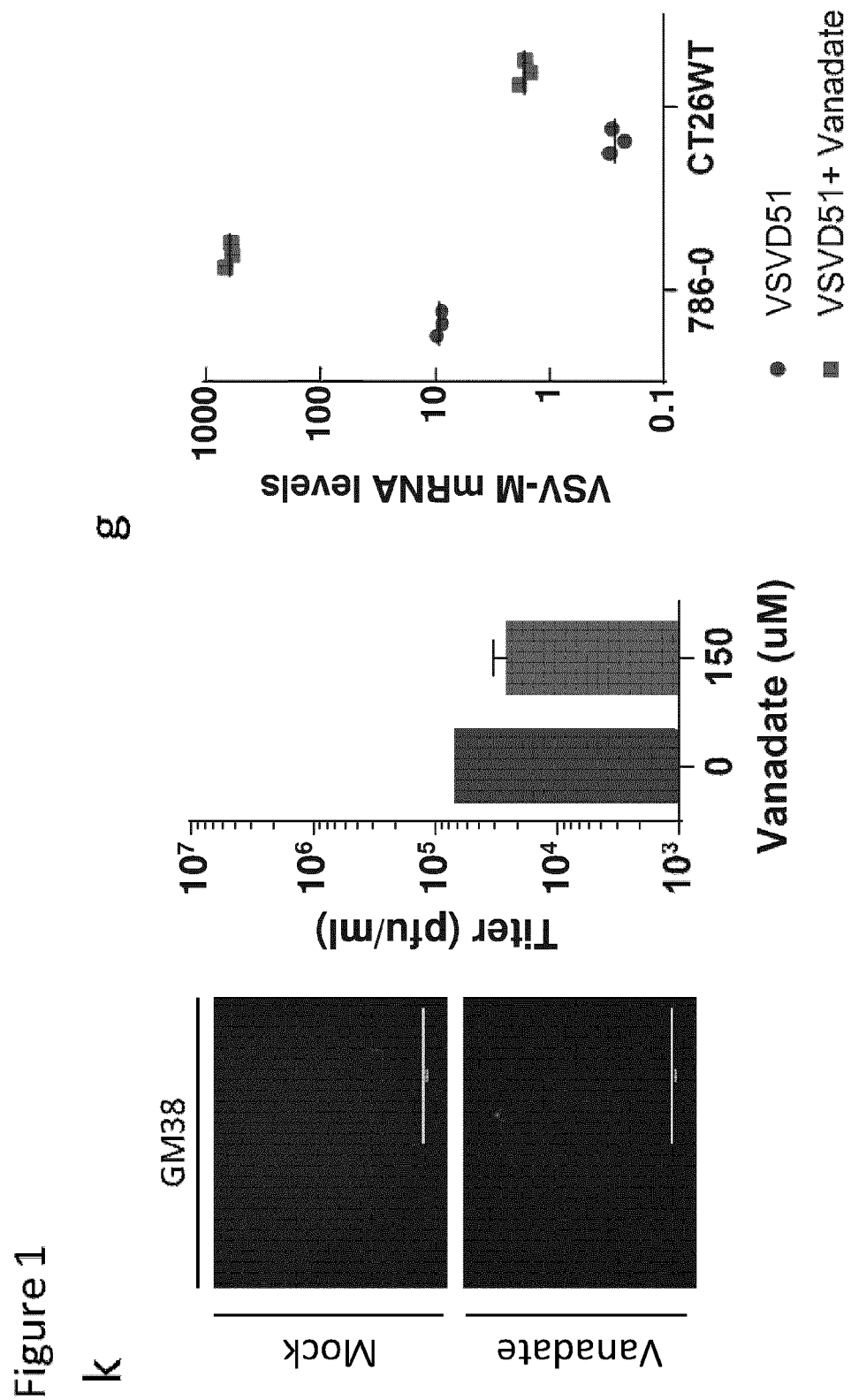
Figure 1H:
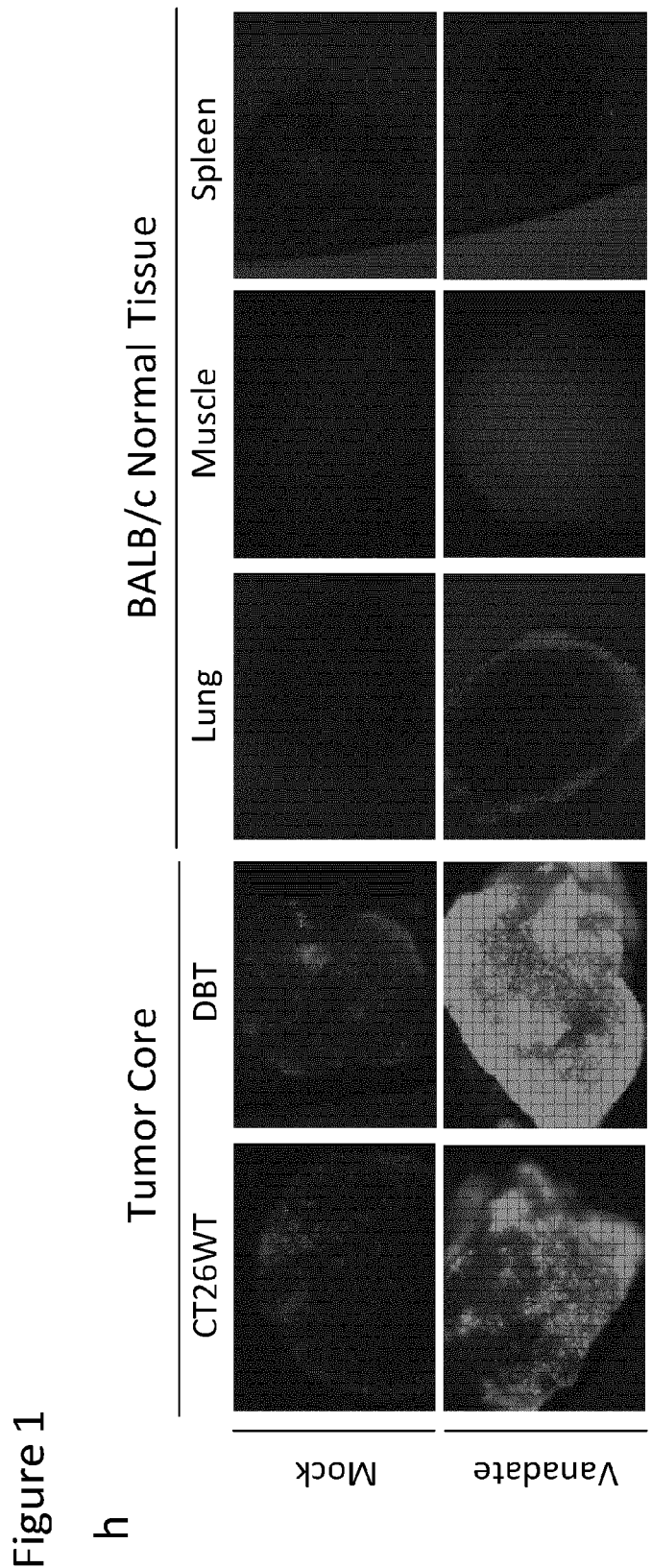

The following description is of one or more preferred embodiments. Several inventions may be described herein with compositions, and kits provided with identical, similar or distinct uses or methods of use.

In an embodiment, there is provided herein a method of enhancing or increasing the infection, spread, titer, or the oncolytic or immunotherapeutic activity of an RNA virus in a cell, for example, but not limited to, a cancer, tumor, or immortalized cell, the method comprising administering a vanadium-containing compound to said cell prior to, after, or concurrently with infection of the cell with the virus.

In another embodiment, there is provided herein a method of enhancing or increasing the infection, spread, titer, or the oncolytic or immunotherapeutic activity of an oncolytic RNA virus in cancer or tumor cells, the method comprising administering a vanadium-containing compound to said cells prior to, after, or concurrently with infection of the cells with the virus.

In a further embodiment, which is not meant to be limiting, the oncolytic RNA virus oncolytic or immunotherapeutic activity is potentiated in cancer or tumor cells as compared to the oncolytic or immunotherapeutic activity of the virus alone or the immunotherapeutic activity of the vanadium-containing compound alone.

In yet another embodiment of any of the compositions, method or methods described above, the vanadium-containing compound enhances RNA virus infection, growth or spread in infection-resistant cancer cells.

In yet another embodiment of any of compositions, method or methods described above, the vanadium-containing compound enhances RNA virus infection, growth or spread in cancer cells and tumors in vivo without inducing virus spread to major organs.

In a further embodiment of any of compositions, method or methods described above, the vanadium-containing compound enhances the virally induced cancer cell death in vivo and in vitro.

In still a further embodiment, which is not meant to be limiting, there is provided compositions comprising one or more of the vanadium-containing compounds, and one or more of a) an RNA virus, a genetically modified RNA virus, an attenuated RNA virus, an oncolytic RNA virus, an RNA virus-based cancer vaccine or cancer gene therapy vector, b) one or more cancer cells, c) a carrier, diluent or excipient, d) a pharmaceutically acceptable carrier, diluent or excipient, e) non-cancer cells; f) cell culture media; g) one or more cancer therapeutics; or any combination of a)-g). The present invention also contemplates embodiments wherein any one or a combination of a-g) are specifically excluded from the composition or kit. Any component or group of components may be excluded if desired.

In yet another embodiment, there is provided herein a kit comprising one or more of the vanadium-containing compounds, and one or more of a) an RNA virus, a genetically modified RNA virus, an attenuated RNA virus, an oncolytic RNA virus, an RNA virus-based cancer vaccine or cancer gene therapy vector, b) one or more cancer cells, c) a pharmaceutically acceptable carrier, diluent or excipient, d)

non-cancer cells; e) cell culture media; f) one or more cancer therapeutics, g) a cell culture plate or multi-well dish; h) an apparatus to deliver the compound to a cell, medium or to a subject; i) instructions for using the compound or any component in the kit, j) a carrier diluent or excipient, or any combination of a)-j). The present invention also contemplates kits wherein any one or a combination thereof of a)-j) are specifically excluded.

It will be understood by the person of skill in the art having regard to the teachings herein that enhancing or increasing viral activity, production, oncolytic activity, or cytotoxicity may include enhancing or increasing at least one of viral infection and/or rate thereof, viral production and/or rate thereof, viral titer and/or rate at which full titer may be reached, viral spread and/or rate thereof, cell lysis and/or rate thereof, viral cytotoxicity and/or rate thereof, or any combination thereof, as compared to when the one or more compounds are not used.

It will be understood by the person of skill in the art having regard to the teachings herein that enhancing or increasing the immunotherapeutic activity of an oncolytic RNA virus may include enhancing or increasing the systemic antitumor immune response through the up-regulation of many cytokines, including higher expression of cytokines induced by the virus or the vanadium-containing compound alone or up-regulation of cytokines not up-regulated by either the virus or the vanadium-containing compound alone.

In certain embodiments, and without wishing to be bound by theory, a vanadium-containing compound as described herein may be used to at least partially subvert the antiviral type I IFN response toward a death-inducing and proinflammatory type II IFN response, which may improve oncolytic virus spread, increase bystander killing of cancer cells, and/or enhance anti-tumor immune stimulation.

By the term "vanadium-containing compound", it is meant compounds which include a vanadium transition metal core. The vanadium core can be in any oxidation state. Such compounds include but are not limited to: Orthovanadate, Metavanadate, Vanadium (V) oxytriethoxyde (VOx), Vanadium (IV) oxide sulphate (VS) and bismaltolato oxovanadium (IV) (BMOV), Vanadium tetra-fluoride and Vanadium tri-bromide. In certain embodiments, Vanadium-containing compounds may include vanadium-based phosphatase inhibitors, for example.

In certain embodiments, vanadium salts and compounds are known to undergo different hydrolytic conversions in solution. Orthovanadate, metavanadate and vanadium(V) oxytriethoxide all result in a solution of $H_2VO_4^-$ at physiological pH, while the solutions prepared from vanadyl sulfate and vanadium(IV) fluoride result in a solution of aqueous V(IV) and V(V), and those prepared from bis (maltolato)oxovanadium(IV) will contain both V(IV) and V(V) maltolato complexes. In the studies described in further detail herein, such compounds may, in certain embodiments, show a robust capacity to enhance OV activity, for example.

By the term "oncolytic virus" it is meant a virus that preferentially infects and lyses cancer or tumor cells as compared to non-cancer or normal cells. Examples of oncolytic viruses known in the art include, without limitation, reovirus, newcastle disease virus, adenovirus, herpes virus, polio virus, mumps virus, measles virus, influenza virus, vaccinia virus, rhabdoviruses such as vesicular stomatitis virus and derivatives/variants thereof. In a preferred embodiment, the virus in the presence of a the vanadium-containing compound as described herein preferentially infects and lyses cancer cells or tumor cells as compared to the virus alone and as compared to normal cells alone or in the presence of the vanadium-containing compound.

By the term "RNA virus" it is meant a virus that has RNA (ribonucleic acid) as its genetic material. The nucleic acid can be either single-stranded RNA or double-stranded RNA, and the RNA can be either negative-sense or positive-sense. Examples of RNA viruses include reovirus, newcastle disease virus, polio virus, mumps virus, measles virus, influenza virus, rhabdoviruses such as vesicular stomatitis virus.

Cytotoxic/oncolytic activity of the virus may be present, observed or demonstrated in vitro, in vivo, or both. Preferably, the virus exhibits cytotoxic/oncolytic activity in vivo.

By a "derivative" or "variant" of a virus, it is meant a virus obtained by selecting the virus under different growth conditions, one that has been subjected to a range of selection pressures, that has been genetically modified using recombinant techniques known within the art, or one that has been engineered to be replication defective and/or express transgenes, or any combination thereof. Examples of such viruses are known in the art, for example from US patent applications 20040115170, 20040170607, 20020037543, WO 00/62735; U.S. Pat. Nos. 7,052,832, 7,063,835, 7,122, 182 (which are hereby incorporated by reference) and others. Preferably the virus is a Vesicular stomatitis virus (VSV), or a related rhabdovirus variant/derivative thereof, for example, selected under specific growth conditions, one that has been subjected to a range of selection pressures, one that has been genetically modified using recombinant techniques known within the art, or a combination thereof. In a preferred embodiment, the virus is VSVΔ51 (Stojdl et al., VSV strains with defects in their ability to shutdown innate immunity are potent systemic anti-cancer agents, Cancer Cell. 2003 October; 4(4):263-75, herein incorporated by reference).

The one or more types of cancer or tumor cells may be cancer or tumor cells in vitro or in vivo from any cell, cell line, tissue or organism, for example, but not limited to human, rat, mouse, cat, dog, pig, primate, horse and the like. In a preferred embodiment, the one or more cancer or tumor cells comprise human cancer or tumor cells, for example, but not limited to lymphoblastic leukemia, myeloid leukemia, adrenocortical carcinoma, AIDS-related cancers, AIDS-related lymphoma, anal cancer, appendix cancer, astrocytoma, atypical teratoid/rhabdoid tumor, basal cell carcinoma, bile duct cancer, bladder cancer, bone cancer, osteosarcoma, malignant fibrous histiocytoma, brain stem glioma, brain tumor, cerebellar astrocytoma, cerebral astrocytoma/malignant glioma, craniopharyngioma, ependymoblastoma, medulloblastoma, pineal parenchymal tumors of intermediate differentiation, supratentorial primitive neuroectodermal tumors and pineoblastoma, visual pathway and hypothalamic glioma, spinal cord tumors, breast cancer, bronchial tumors, Burkitt lymphoma, carcinoid tumor, central nervous system lymphoma, cervical cancer, chordoma, chronic lymphocytic leukemia, chronic myelogenous leukemia, chronic myeloproliferative disorders, colon cancer, cutaneous T-Cell lymphoma, embryonal tumors, endometrial cancer, ependymoblastoma, ependymoma, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), gastrointestinal stromal cell tumor, germ cell tumors, extracranial, extragonadal, ovarian, gestational trophoblastic tumor, glioma, hairy cell leukemia, head and neck cancer, hepatocellular (Liver) cancer, histiocytosis, Langerhans cell cancer, Hodgkin lymphoma, hypopharyngeal cancer, islet cell tumors, Kaposi sarcoma, kidney cancer, laryngeal cancer, lymphocytic leukemia, hairy cell leukemia, lip and oral cavity cancer, liver cancer, non-small cell lung cancer, small cell lung cancer, Hodgkin lymphoma, non-Hodgkin lymphoma, malignant fibrous histiocytoma of bone and osteosarcoma, medulloblastoma, medulloepithelioma, melanoma, intraocular melanoma, Merkel cell carcinoma, mesothelioma, metastatic squamous neck cancer, mouth cancer, multiple endocrine neoplasia syndrome, multiple myeloma/plasma cell neoplasm, nasal cavity and paranasal sinus cancer, nasopharyngeal cancer, neuroblastoma, oral cancer, oropharyngeal cancer, ovarian cancer, pancreatic cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter cancer, transitional cell cancer, respiratory tract carcinoma, retinoblastoma, rhabdomyosarcoma, salivary gland cancer, uterine sarcoma, skin cancer, Merkel cell skin carcinoma, small intestine cancer, soft tissue sarcoma, squamous cell carcinoma, squamous neck cancer, stomach (Gastric) cancer, supratentorial primitive neuroectodermal tumors, T-Cell lymphoma, testicular cancer, throat cancer, thymoma and thymic carcinoma, thyroid cancer, trophoblastic tumor, urethral cancer, uterine cancer, endometrial cancer, uterine sarcoma, vaginal cancer, vulvar cancer, or Wilms tumor. However, the compounds and compositions described herein possible may be used to treat other cancers or tumor in vivo or in vitro.

In another embodiment, there is provided herein a composition comprising a) one or more vanadate-containing compounds as described herein and b) one or more additional components, for example, but not limited to 1) a carrier, diluent or excipient, 2) a pharmaceutically acceptable carrier, diluent or excipient, 3) a RNA virus, for example, but not limited to an attenuated virus, a genetically modified virus or an oncolytic virus, 4) cancer or tumor cells, 5) non-cancerous or normal cells, 6) cell culture media, 7) one or more cancer therapeutics, for example, but not limited to chemotherapeutics. As an example, but not to be considered limiting in any manner, cyclophosphamide (CPA) is a common chemotherapy drug used primarily for the treatment of lymphoma, chronic lymphocytic leukemia and breast, ovarian and bladder cancers. CPA is converted into its active metabolites, 4-hydroxycyclophosphamide and aldophosphamide by liver oxidases. Use of CPA as an immune suppressant to enhance viral oncolysis has improved virotherapy efficacy in combination with oncolytic variants of HSV, adenoviruses, measles virus, reovirus, and vaccinia virus.

A further cancer therapeutic known in the art is cisplatin. Cisplatin binds and cross-links cellular DNA leading to apoptosis when DNA is not repaired. Cisplatin has been investigated in combination with oncolytic adenoviruses, herpes viruses, parvovirus, vaccinia virus, and vesicular stomatitis virus. Enhanced therapeutic activity in vitro and in vivo has been observed when combining cisplatin with oncolytic variants of adenovirus, herpesvirus, parvovirus and vaccinia virus whereas slight inhibition was observed for oncolytic variant of vesicular stomatitis virus.

Mitomycin C (MMC) is a DNA cross-linking antibiotic with antineoplastic properties. MMC exhibited synergistic cytotoxicty with oncolytic HSV. In vivo, combination of oncolytic herpes virus and MMC significantly improved therapeutic effects in models of gastric carcinomatosis and non-small cell lung cancer.

Doxorubicin is an anthracycline antibiotic that intercalates into DNA and prevents the action of topoisomerase II. Doxorubicin was synergistically cytotoxic when combined with oncolytic adenovirus (ONYX-015) and the combination reduced tumor growth relative to the monotherapies. ONYX-015 was successfully combined with MAP (mitomycin C, doxorubicin and cisplatin) chemotherapy in a phase I-II clinical trial for treatment of advanced sarcomas.

Gancyclovir (GCV) is a widely used antiviral agent, originally developed for the treatment of cytomegalovirus infections. GCV is a guanasine analogue prodrug that upon phosphorylation by herpes virus thymidine kinase (TK) competes with cellular dGTP for incorporation into DNA resulting in elongation termination. Oncolytic viruses encoding the HSV TK gene lead to an accumulation of toxic GCV metabolites in tumor cells which interfere with cellular DNA synthesis leading to apoptosis. Targeted oncolytic HSV viruses in combination with GCV significantly improved survival in models of human ovarian cancer and rat gliosarcoma. Adenoviruses, engineered to express the HSV TK gene, also show enhanced anti-tumor activity when combined with GCV.

CD/5-FC enzyme/pro-drug therapy has also proven successful in combination with oncolytic virotherapy. 5-FU is a pyrimidine analogue that inhibits the synthesis of thymidine. The anti-tumor activity of two different oncolytic vaccinia viruses expressing CD was significantly enhanced when combined with 5-FC therapy in immune-competent ovarian cancer and immune suppressed colon cancer models.

Taxanes are a class of chemotherapy drugs, including paclitaxel and docetaxel, which cause stabilization of cellular microtubules thereby preventing function of the cellular cytoskeleton, a requirement for mitosis. Combination of docetaxel or paclitaxel with an urothelium- or prostate-targeted oncolytic adenovirus significantly reduced in vivo tumor volume and resulted in synergistic in vitro cytotoxicity.

Rapamycin (sirolimus) is an immunosuppressant commonly used in transplant patients however it has also been shown to significantly enhance the oncolytic effects of the oncolytic variants of poxviruses myxoma and vaccinia virus.

The prototypical proteosome inhibitor MG-132 enhanced cellular CAR expression in Lovo colon carcinoma cells, which was accompanied with enhanced oncolytic adenovirus target gene expression and oncolysis.

The efficacy of oncolytic VSV against chronic lymphocytic leukemia cells was increased by combination therapy with the BCL-2 inhibitor EM20-25.

One group showed that a single dose of angiostatic cRGD peptide treatment before oncolytic virus treatment enhanced the antitumor efficacy of oncolytic HSV.

Other groups have shown that immune checkpoint inhibitors targeting CTLA4 or PD1 in combination with oncolytic Newcastle disease virus[42], oncolytic measles virus[43], and oncolytic VSV[44] as well as oncolytic HSV-1 [45] enhance their anticancer activity.

For in vivo therapeutic applications, preferably there is provided a pharmaceutical composition comprising one or more vanadate-containing compounds and a pharmaceutically acceptable carrier, diluent or excipient, optionally containing other solutes such as dissolved salts and the like. In a preferred embodiment, the solution comprises enough saline, glucose or the like to make the solution isotonic. Pharmaceutical compositions and methods of preparing pharmaceutical compositions are known in the art and are described, for example, in "Remington: The Science and Practice of Pharmacy" (formerly "Remingtons Pharmaceutical Sciences"); Gennaro, A., Lippincott, Williams & Wilkins, Philidelphia, Pa. (2000), herein incorporated by reference.

Administration of such compositions may be via a number of routes depending upon whether local and/or systemic treatment is desired and upon the area to be treated. In a first embodiment, which is not meant to be limiting, the compound is administered locally to the area to be treated. Administration may be topical (including ophthalmic and to mucous membranes including vaginal and rectal delivery), pulmonary (e.g. by inhalation or insufflation of powders or aerosols, including by nebulizer), intratracheal, intranasal, epidermal and transdermal, oral or parenteral. Parenteral administration includes intravenous, intraarterial, subcutaneous, intraperitoneal or intramuscular injection or infusion, or intracranial, e.g. intrathecal or intraventricular, administration. Also contemplated is intra-tumor injection, perfusion or delivery into the general vicinity of the tumor or injection into the vasculature supplying a tumor. Alternatively, the vanadate-containing compounds may be formulated in a tablet or capsule for oral administration. Alternate dosage forms, including slow-release, sustained-release, extended release, as would be known in the art are also contemplated.

For administration by inhalation or insufflation, the compounds can be formulated into an aqueous or partially aqueous solution, which can then be utilized in the form of an aerosol. For topical use, the modulators can be formulated as dusting powders, creams or lotions in pharmaceutically acceptable vehicles, which are applied to affected portions of the skin.

Without wishing to be liming, the dosage requirements for the vanadate-containing compounds of the present invention may vary with the particular compositions employed, the route of administration and the particular subject being treated. Dosage requirements can be determined by standard clinical techniques known to a worker skilled in the art. Typically, treatment will generally be initiated with small dosages less than the optimum dose of the compound or compound/virus. Thereafter, the dosage is increased until the optimum or satisfactory effect under the circumstances is reached. In general, the vanadate-containing compound or pharmaceutical compositions comprising the vanadate-containing compound are administered at a concentration that will generally afford effective results without causing significant harmful or deleterious side effects. Administration can be either as a single unit dose or, if desired, the dosage can be divided into convenient subunits that are administered at suitable times throughout the day.

The vanadate-containing compound may be employed in sequential administration, for example, before, after or both before and after administration of a RNA virus, for example, but not limited to an attenuated virus, a genetically modified virus, a cancer vaccine, a cancer gene therapy vector or an oncolytic virus. Alternatively, the vanadate-containing compound may be administered concurrently or in combination with a RNA virus as described above, preferably in combination with an oncolytic virus. In addition, the vanadate-containing compound may be used with an oncolytic virus as described above and in combination with one or more cancer therapeutics or cancer therapies as is known to a person of skill in the art, for example but not limited to interferon therapy, interleukin therapy, colony stimulating factor therapy, immunotherapy, immune checkpoint inhibitor therapy, chemotherapeutic drugs, for example, but not limited to 5-fluorodeoxyuridine amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, gliadel, hydroxycarbamide, idarubicin, ifosfamide, irinotecan, leucovorin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine or a combination thereof. Further, anti-cancer biologics may also be employed, for example, but without limitation, monoclonal antibodies and the like.

In another embodiment, there are provided herein methods and uses of the compositions as described herein for increasing or enhancing the spread of an RNA virus, for example, a genetically modified virus, an attenuated virus, a cancer vaccine, a cancer gene therapy vector, or an oncolytic virus in one or more cells, for example, but not limited to one or more types of cancer or tumor cells, increasing or enhancing the cytotoxicity/oncolytic activity of an oncolytic virus against one or more cancer or tumor cells, increasing or enhancing the production, yield or reproductive capacity of a RNA virus, for example, a genetically modified virus, an attenuated virus, cancer vaccine, cancer gene therapy vector, an oncolytic virus, or, any combination of the above. In an embodiment, which is not meant to be limiting in any manner, the compositions reduces the viability of a cancer or tumor cell by either killing the cancer or tumor cell or limiting its growth for a period of time.

In another embodiment, the cells may be cancer cells in vivo, or in vitro. In a further embodiment, the in vivo cancer cells may be from a mammalian subject. In still a further embodiment, the mammalian subject may be a human subject.

In another embodiment, there is provided herein a composition comprising a cell culture medium and a vanadium-containing compound. In certain embodiments, the composition may be used for culturing a cell infected with an RNA virus.

Figure 3:
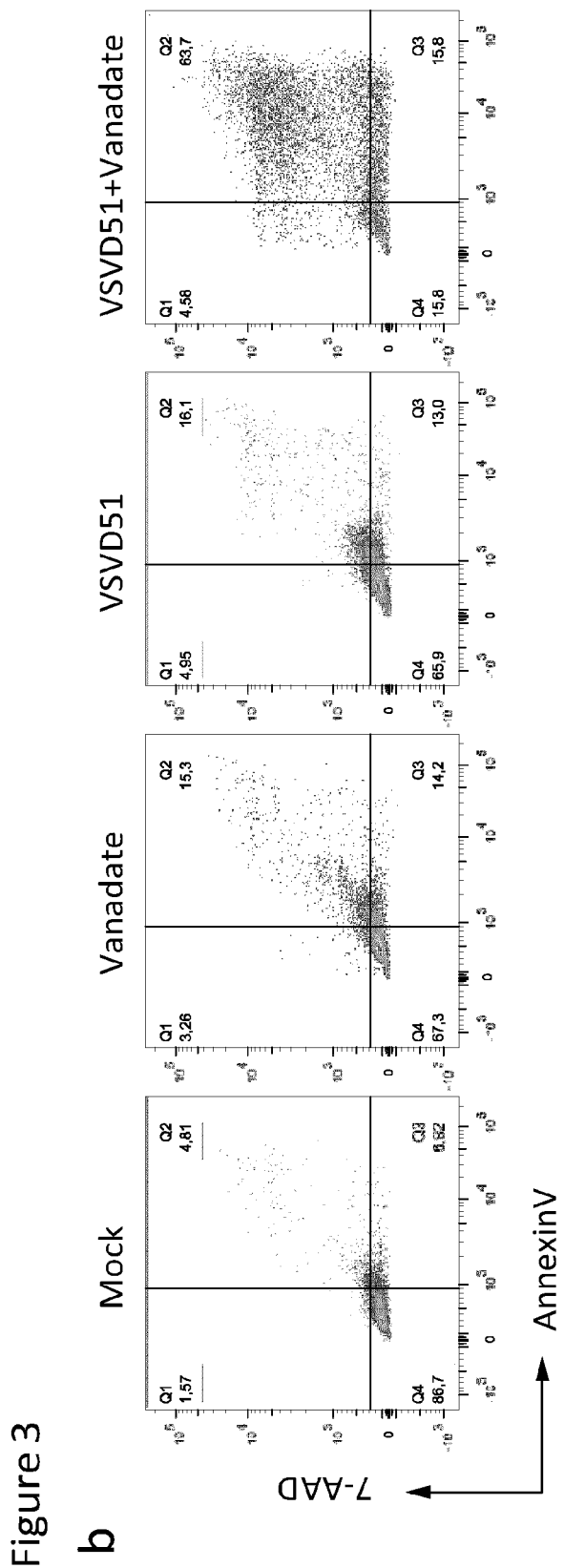
FIG. 3 shows results in which Vanadate facilitates cell death via type I interferon and ROS mediated apoptosis during viral infection. (a) 786-0 were pretreated for 4 hours with a range of concentration of various vanadate based compounds (Meta=metavanadate, ortho=orthovanadate, VS=Vanadium (IV) oxide sulfate, VOX=Vanadium (V) oxytriethoxide, BMOV=bismaltolato oxovanadium (IV)) and were subsequently infected with oncolytic VSVΔ51 expressing GFP at an MOI of 0.01. Cell viability was assayed in 786-0 cells 24 hours post infection. Results were normalized to the average of the values obtained for the corresponding uninfected, untreated cells (N=4). (b) 786-0 were pretreated with dose range of orthovanadate for 4 hours and subsequently infected with oncolytic VSVΔ51 expressing GFP at an MOI of 0.01. 24 hours post induction of cell death was determined by annexin V and 7-aminoactinomycin D (7-AAD) staining. Numbers indicate the percentage in each quadrant. (c,d,e) 786-0 were pretreated with dose range of orthovanadate for 4 hours and subsequently infected at an MOI of 0.01 with either (c) VSVΔ51, UV-inactivated VSVΔ51 or VSVΔ51 Gless, or treated with (d) IFNa, IFNb or PolyI:C. Cell viability was assayed 48 hours post infection. (e,g) Corresponding cell morphology presented. (f) 786-0 were pretreated with orthovanadate or left untreated and treated with N-acetyl-L-cysteine (NAC), and infected with VSVΔ51 (MOI: 0.01). (e) Cell viability was assayed in 786-0 cells 24 hours post infection. Results were normalized to the average of the values obtained for the corresponding uninfected, untreated cells (N=4). (g) Viral titer were determined 24 hours post infection from supernatants (N=3). (h) Cell lysates of 786-0 treated with orthovanadate and IFNb was collected and probed for pSTAT1, STAT1 and 3-tubulin by western blot. (i) Various cell lines were pretreated for 4 hours with a range of concentration of orthovanadate and were subsequently infected with oncolytic VSVΔ51 expressing GFP at an MOI of 0.01. Cell viability was assayed in 786-0 cells 48 hours post infection. Results were normalized to the average of the values obtained for the corresponding uninfected, untreated cells (N=4)
Figure 3:
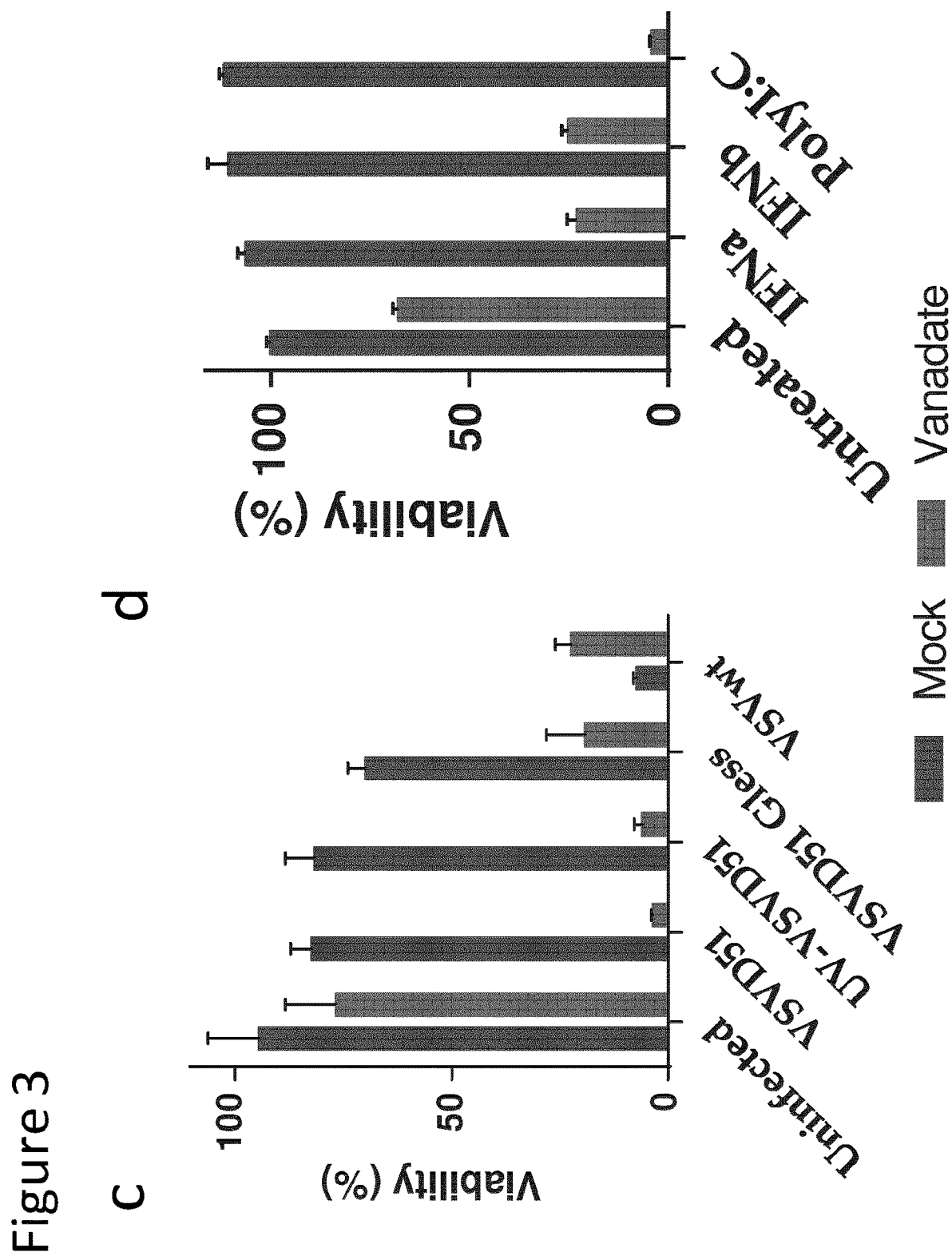
Figure 3:
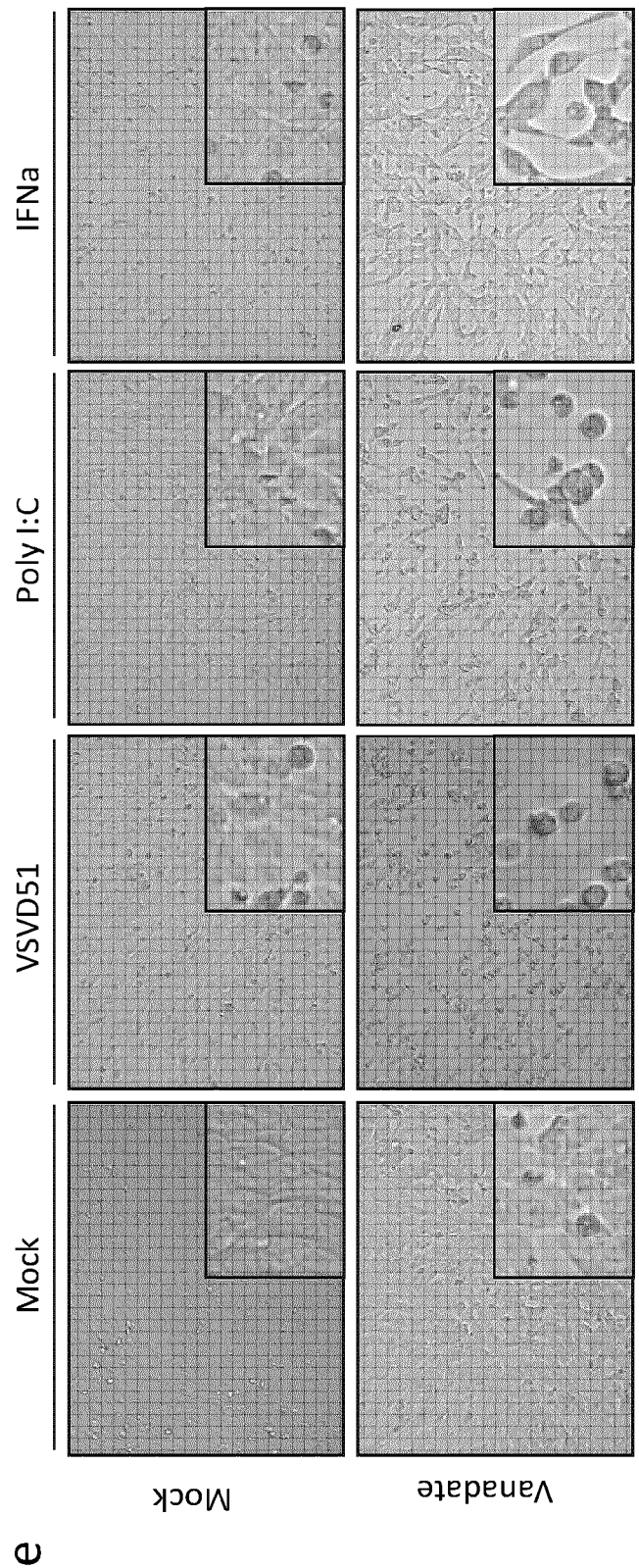
Figure 3:
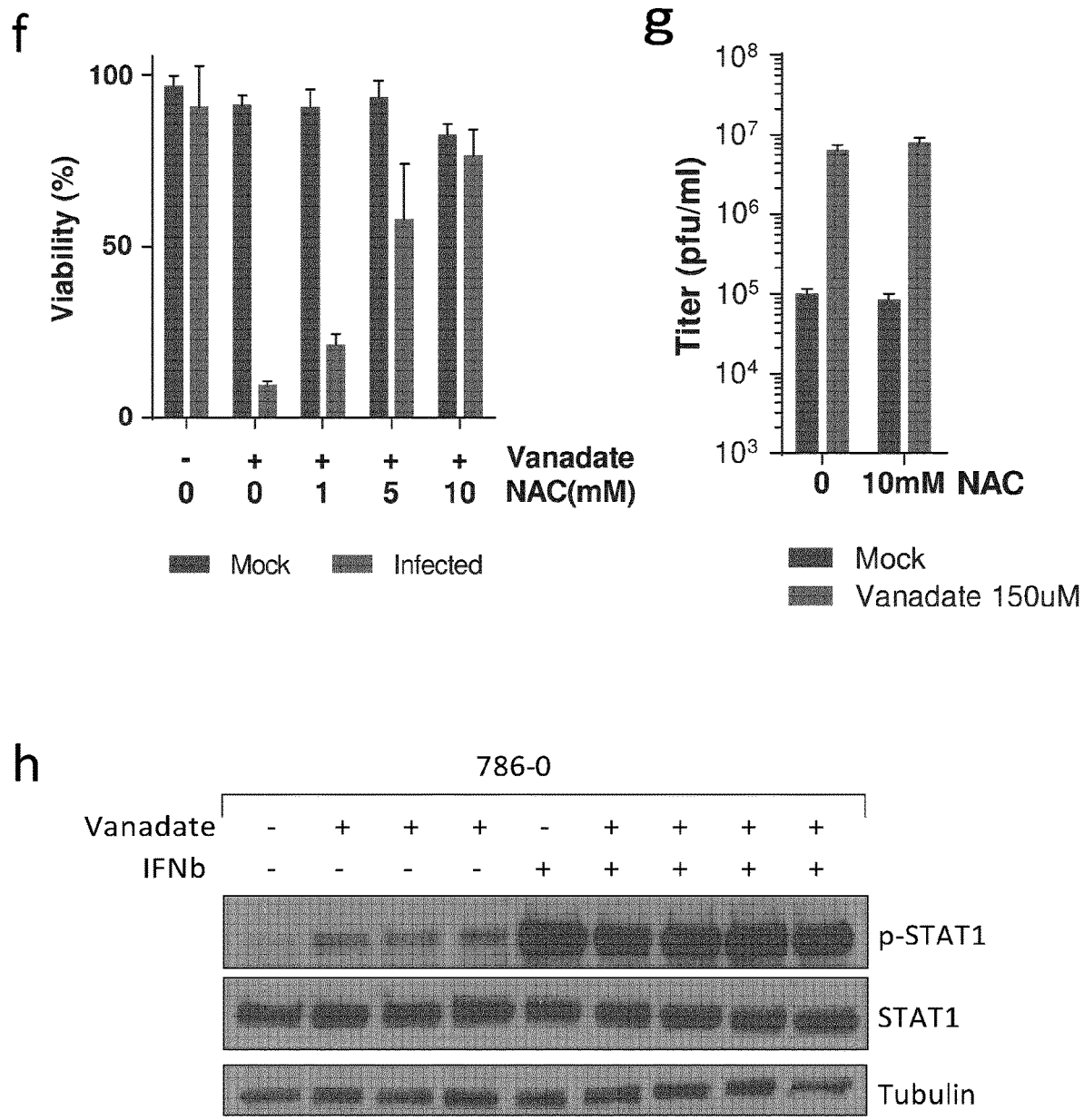

In an embodiment, there is provided herein a method of enhancing or increasing the infection, spread, titer, or the oncolytic or immunotherapeutic activity of an RNA virus in a cell, for example, but not limited to, a cancer, tumor, immortalized cell, or other suitable cell, the method comprising administering a vanadium-containing compound to said cell prior to, after, or concurrently with infection of the cell with the virus. In a further embodiment which is not meant to be limiting in any manner, the compounds and compositions described herein and throughout may be used in an industrial or pharmaceutical manufacturing setting for producing RNA viruses, genetically modified RNA viruses, oncolytic RNA viruses, RNA virus-based vaccines, and/or RNA virus-based vectors and the like in cells which may include, among others, MRC-5, WI-38 and Vero cells. Viruses that might be desirable to produce in this manner include, but are not limited to Reovirus, measles, rhabdovirus (rabies, vsv, mgl), sindbis virus, influenza virus, Poliovirus, Rhinovirus, Hepatitis A, Hepatitis C virus, Hepatitis D virus, Sindbis Virus, Semilki Forest virus, Ebola virus, Marburg Virus, Rift Valley fever virus, Lassa Virus, Dengue virus, Yellow Fever Virus, Rotavirus, Zika Virus, Japanese Encephalitis Virus, West Nile virus, Sponweni Virus, Newcastle Disease Virus, Corona Virus, SARS, Rubella virus, Ross River Virus, Chikungunya virus. Measles Virus, Mumps Virus, Human respiratory syncytial virus and others, including Group VI RNA viruses which include, but are not limited to lentiviruses and retroviruses.

In certain embodiments, the cell may comprise a cell of an egg. By way of example, in certain embodiments the cell may comprise a cell of an egg, and the egg may be used in vaccine production.

The present invention will be further illustrated in the following examples.

EXAMPLES

Example 1: Vanadate Enhances the Spread of Oncolytic RNA Viruses

We tested the impact of sodium orthovanadate (FIG. 1*a*) on the growth of oncolytic VSVΔ51 in 786-0 renal carcinoma cells. VSVΔ51 is a genetically attenuated version of wild-type vesicular stomatitis virus (wtVSV), a negative single strand RNA virus belonging to the family of rhabdoviridae. While wtVSV is inherently tumor-tropic, VSVΔ51 achieves improved tumor-selectivity over wtVSV due to its incapacity to overcome the cellular antiviral defense [37]. By plaque assay, we found that between 10-1000 uM doses, vanadate could significantly increase viral output (FIG. 1*b*). Use of a GFP-expressing VSVΔ51 revealed a correspondingly marked increase in the number of virus-infected cells (FIG. 1*c*). Comparable results were obtained in various human and mouse cancer cell lines resistant to VSVΔ51 infection (FIG. 7). Single and multi-step growth curves in 786-0 cells revealed that vanadate more robustly enhanced the yield of VSVΔ51 when provided at low multiplicity of infection (MOI) compared to high MOI, indicating that vanadate promotes improved viral spread (compare FIG. 1 *d,e*). To further assess the ability of Vanadate to enhance the spread of the virus, we treated and infected various human and mouse cancer cell lines. Plaques formed were detected by GFP fluorescence and furthermore by coomassie stain. Vanadate substantially increased plaque size in multiple cell lines, including both infection-resistant and sensitive (FIG. 8). Whereas VSVΔ51 spread was robustly enhanced by vanadate, modest improvements in wtVSV yield were observed, again suggesting the possibility that vanadate improves viral spread since wtVSV can effectively overcome cellular antiviral responses in the 786-0 cell line. The impact of Vanadate on viral growth was increasingly evident with increasing pre-treatment time (maximum tested 24 h), with the effect of vanadate being close to nil when provided over 12 h post infection (FIG. 1*f*). Corresponding to viral titers and GFP expression data, FIG. 1*g* shows that vanadate increased the production of VSVΔ51 matrix (M) protein mRNA and/or viral genomes in infected 786-0 cells as well as in mouse CT26-WT colon cancer cells. Vanadate was subsequently tested using different RNA and DNA viruses. Similarly to VSVΔ51, yield of Measles and Sindbis virus (negative and positive single strand RNA viruses respectively) was improved following treatment of 786-0 cells with vanadate. In sharp contrast, HSV-1 (mutant N212) was robustly inhibited, suggesting the growth promoting effects of vanadate are virus-specific (FIG. 1*i*). We next tested whether vanadate could also enhance VSVΔ51 in GM38 fibroblasts and found that viral growth was not enhanced in these normal cells (FIG. 1*k*). We further compared the ability of mouse tumor cores as well as normal lung, muscle and spleen tissues obtained from mice implanted with CT26WT and DBT (glioma) tumors to be infected by VSVΔ51-GFP in presence and absence of vanadate. Fluorescence microscopy images in FIG. 1*h* show that vanadate robustly increased the growth of the virus in tumor cores but not in normal tissue cores.

Example 2: Vanadium-Based Compounds have Unique Viral Enhancing Properties

Orthovanadate has been shown to inhibit tyrosine phosphatases, an activity which is linked to its close structural and steric resemblance to phosphate[46]. We therefore tested whether phosphate could reproduce similar effects but found that in contrast with vanadate, various phosphate salts had no impact on viral growth (FIG. 2*a*). A key feature of orthovanadate is its oxidized vanadium transition metal core. We wanted to determine whether other oxidized transition metals could potentially enhance viral growth. In sharp contrast with Vanadium, neither Manganese, Molybdene, or Tungsten oxide salts could enhance VSVΔ51 growth (FIG. 2*b*). Chromium trioxide did enhance viral growth but only at a single dose tested (10 uM, FIG. 2*b*) and was highly toxic in comparison to orthovanadate (not shown). The protonation state of orthovanadate at different pH had no impact on its activity (FIG. 2*c*). Because this suggested the virus-enhancing effect was linked to the vanadium itself, we tested other oxidized vanadium complexes, including Metavanadate, Vanadium (V) oxytriethoxyde (VOx), Vanadium (IV) oxide sulphate (VS) and bismaltolato oxovanadium (IV) (BMOV). All of these compounds effectively enhanced VSVΔ51 growth (FIG. 2*d-f*). Similar results were obtained using Vanadium tetra-fluoride and Vanadium tri-bromide (FIG. 2*g*). Interestingly, orthovanadate's pro-viral activity was abrogated upon inclusion of L-Ascorbic Acid, a potent metal chelating agent (FIG. 2*h*).

Example 3: Vanadate Enhances Virus and Cytokine-Induced Death

While our data suggested that Vanadium-based compounds enhanced VSVΔ51 spread in cancer cells, we wondered whether this could also impact its oncolytic activity. FIG. 3*a* shows indeed that while vanadium based compounds has some anticancer effects on their own at high doses, cytotoxicity was vastly enhanced upon co-infection with a low MOI of VSVΔ51, which is otherwise innocuous to 786-0 cells. A similar effect was observed using orthovanadate in various human and rodent cancer cell lines (FIG. 3*i*). The mode of cell death was found to exhibit characteristics of apoptosis as determined by flow cytometry following staining with Annexin V and 7-AAD (FIG. 3*b*). Interestingly, the impact of vanadate on cell death was independent on the effect of vanadate on viral replication since increased 786-0 cell death was also observed using UV-inactivated VSV, as well as using version of VSVΔ51 devoid of its capacity to produce glycoprotein (G-less), which can only undergo one round of infection and does not spread (FIG. 3*c*). This suggested a potential for bystander killing and so we tested whether antiviral IFN normally secreted following infection of 786-0 cells by VSVΔ51 could produce similar effects in combination with vanadate. Indeed, FIGS. 3*d-e* show that Type I IFN (α and β), could lead to cytotoxicity in 786-0 cells in the presence of vanadate. Similar effects were obtained when challenging cells with poly I: C, a TLR3 agonist. Because vanadate has been previously shown to increase cellular reactive oxygen species (ROS)[47], we wondered whether the effects of vanadate on virus-induced death could be ROS mediated. To evaluate this, we treated infected cells with vanadate and increasing concentrations of N-Acetyl Cysteine (NAC), which repletes cellular glutathione and reduces the levels of cellular ROS [48]. Increasing NAC had the effect of antagonizing vanadate's capacity to enhance virally induced death (FIG. 3f). However, the highest dose of NAC did not abrogate vanadate's capacity to enhance viral spread (FIG. 3g), again suggesting that these activities of vanadate are distinct. Because type I IFN is involved in limiting viral spread but also induced more significant death in combination with vanadate, we wondered what effect vanadate treatment would have on the induction of the phosphorylation of STAT-1, an event that follows immediately downstream of cytokine binding to type I IFN receptors, and which is itself regulated by various kinases and phosphatases [49]. We found that contrary to what we would expect from an enhancer of virus spread due to its association to antiviral signaling, the phosphorylation of STAT1 was increased by vanadate at baseline. As expected, IFN-β induced the phosphorylation of STAT1; however, this was not altered by treatment with vanadate (FIG. 3h).

Example 4: Vanadate Enhances the Oncolytic Activity of VSVΔ51 In Vivo

Figure 2:
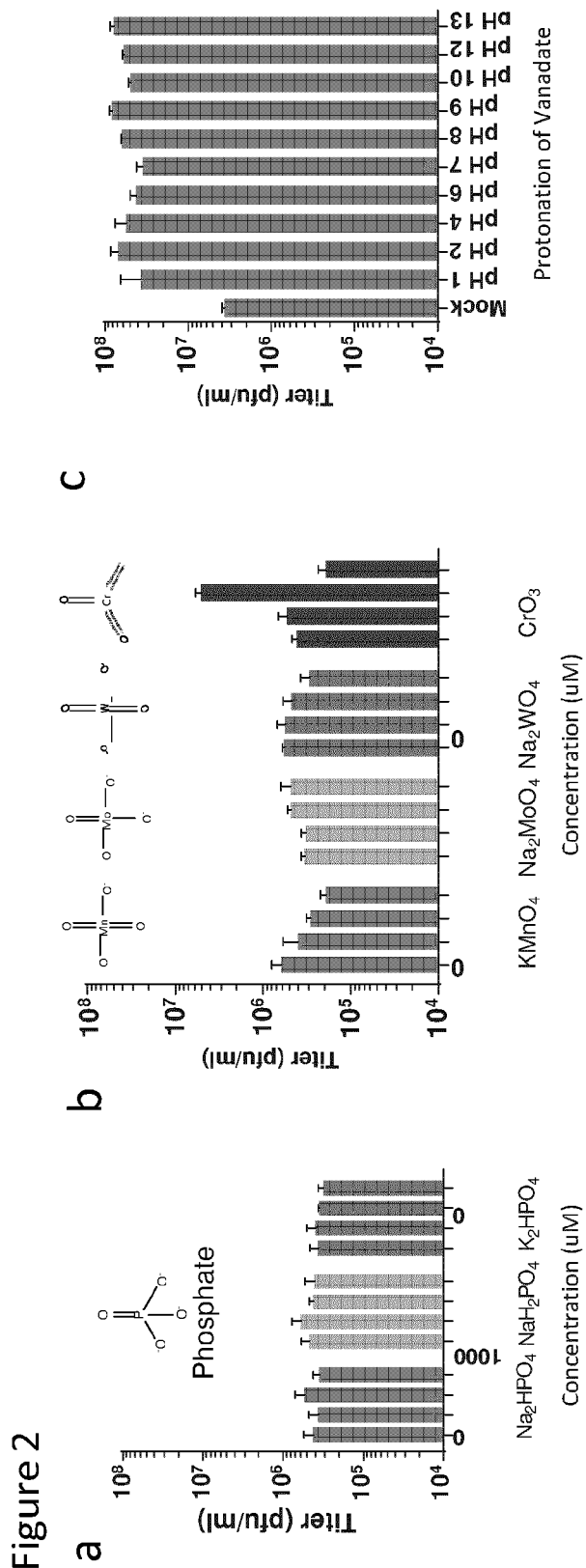
FIG. 2 shows results in which viral enhancement is dependent on Vanadium. 786-0 were pretreated for 4 hours with various concentration (a) of phosphate salts or pyrophosphate, (b) various oxidized transitional metals, (c) orthovanadate solution at various pH, (e,f) various vanadate based compounds, (g) various vanadium based compound, and were subsequently infected with oncolytic VSVΔ51 expressing GFP at an MOI of 0.01. (a,b,f,g) Corresponding viral titer were determined 24 hours post infection from supernatants (N=3). Error bars indicate s.e.m. (d,e) Corresponding GFP positive cell counts 24 hours post infection. (g) and corresponding fluorescent images are presented. (d) Structure of various vanadate based compounds is illustrated. (h) 786-0 were pretreated with 200 uM of orthovanadate or left untreated and treated with cheating agent ascorbic acid (L-AA), and infected with VSVΔ51 (MOI: 0.01). Corresponding viral titer were determined 24 hours post infection from supernatants (N=3). Error bars indicate s.e.m.
Figure 2:
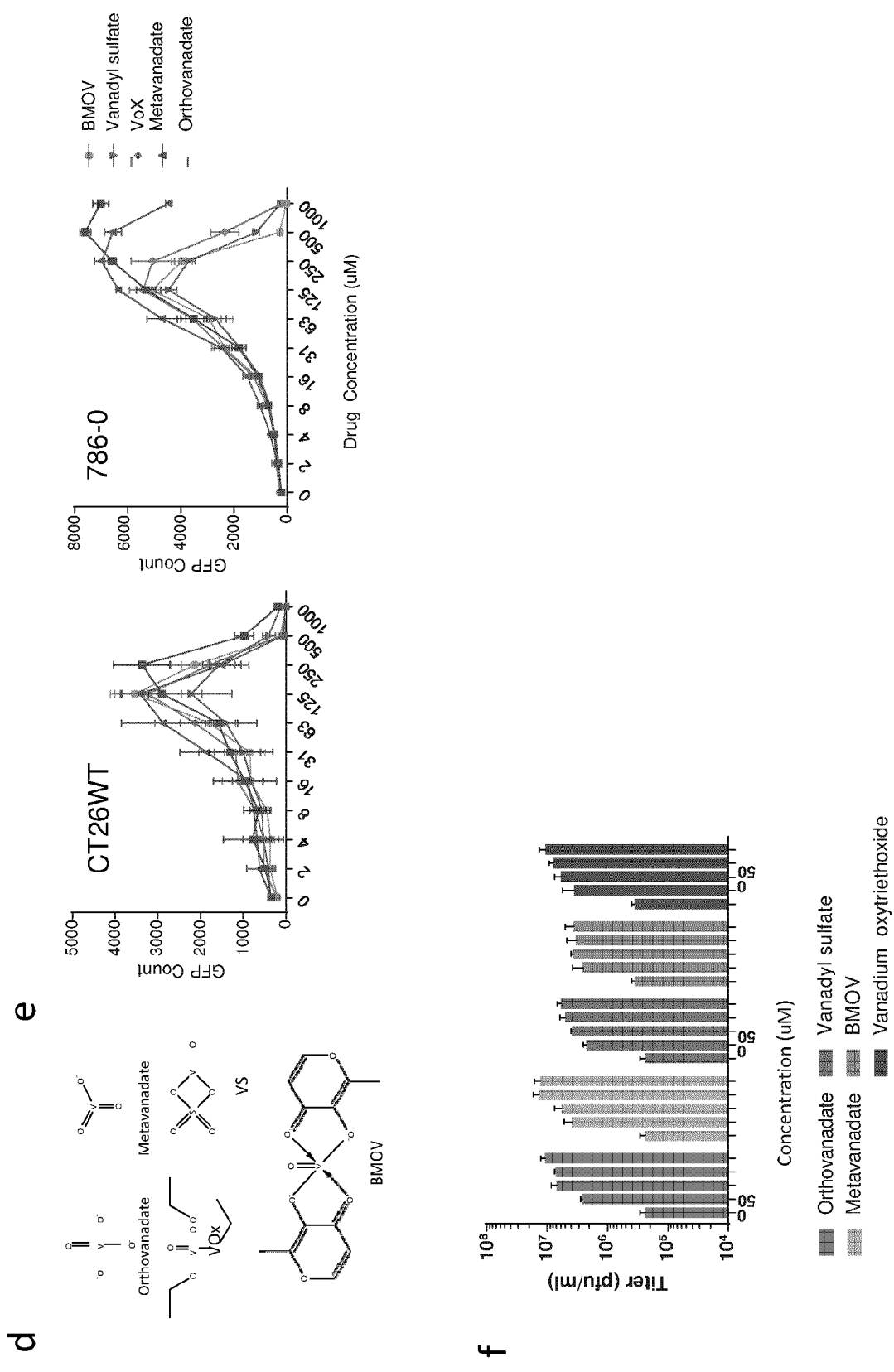
Figure 2:
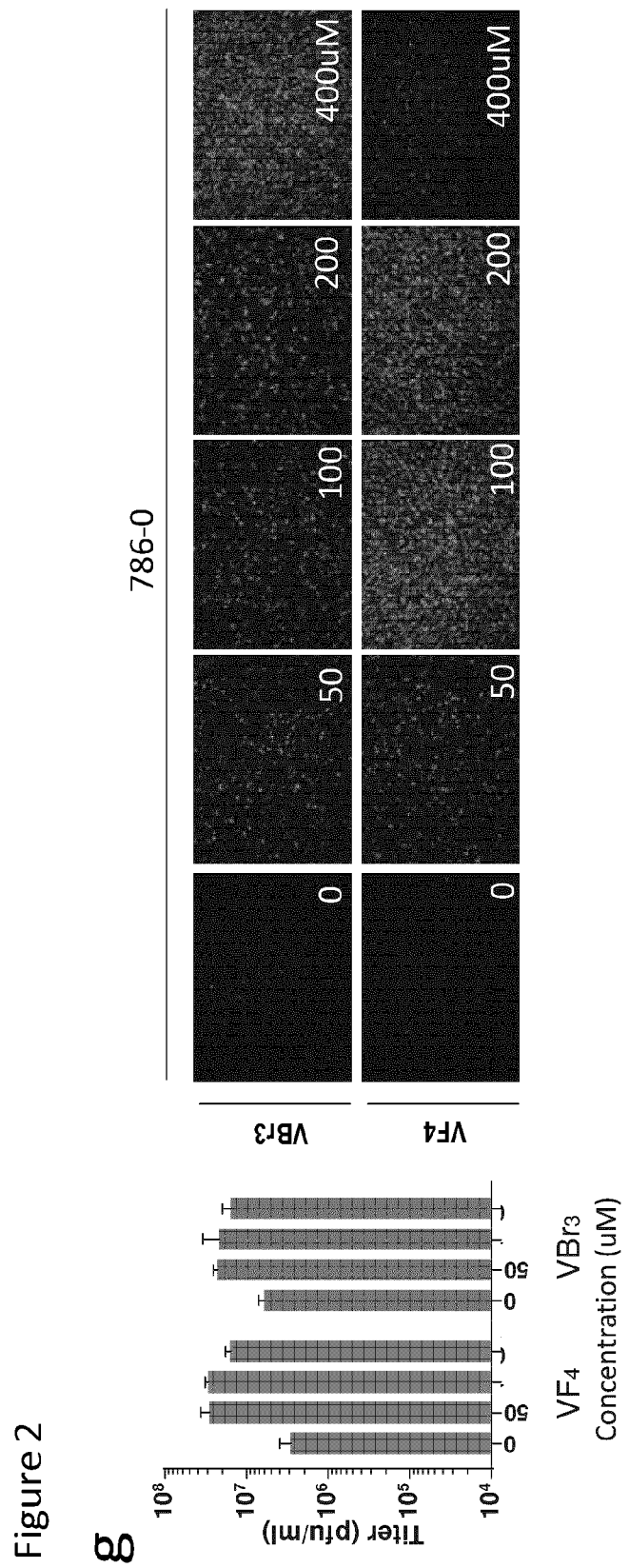
Figure 2:
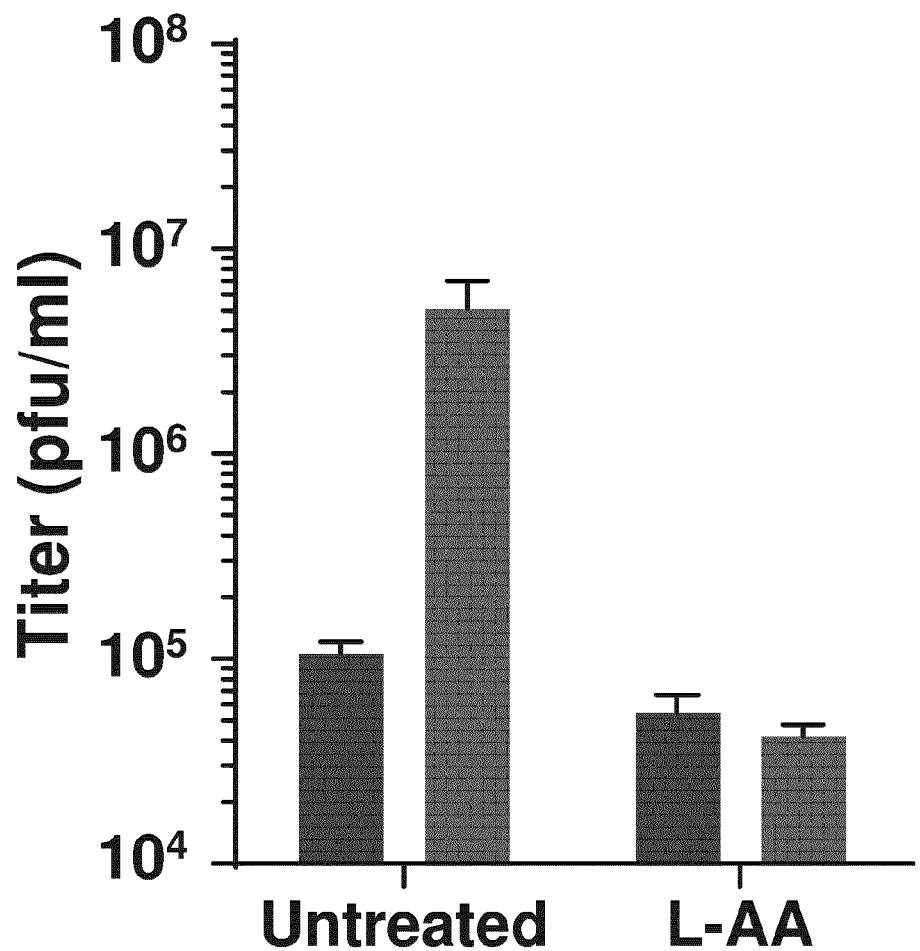
Figure 4A:
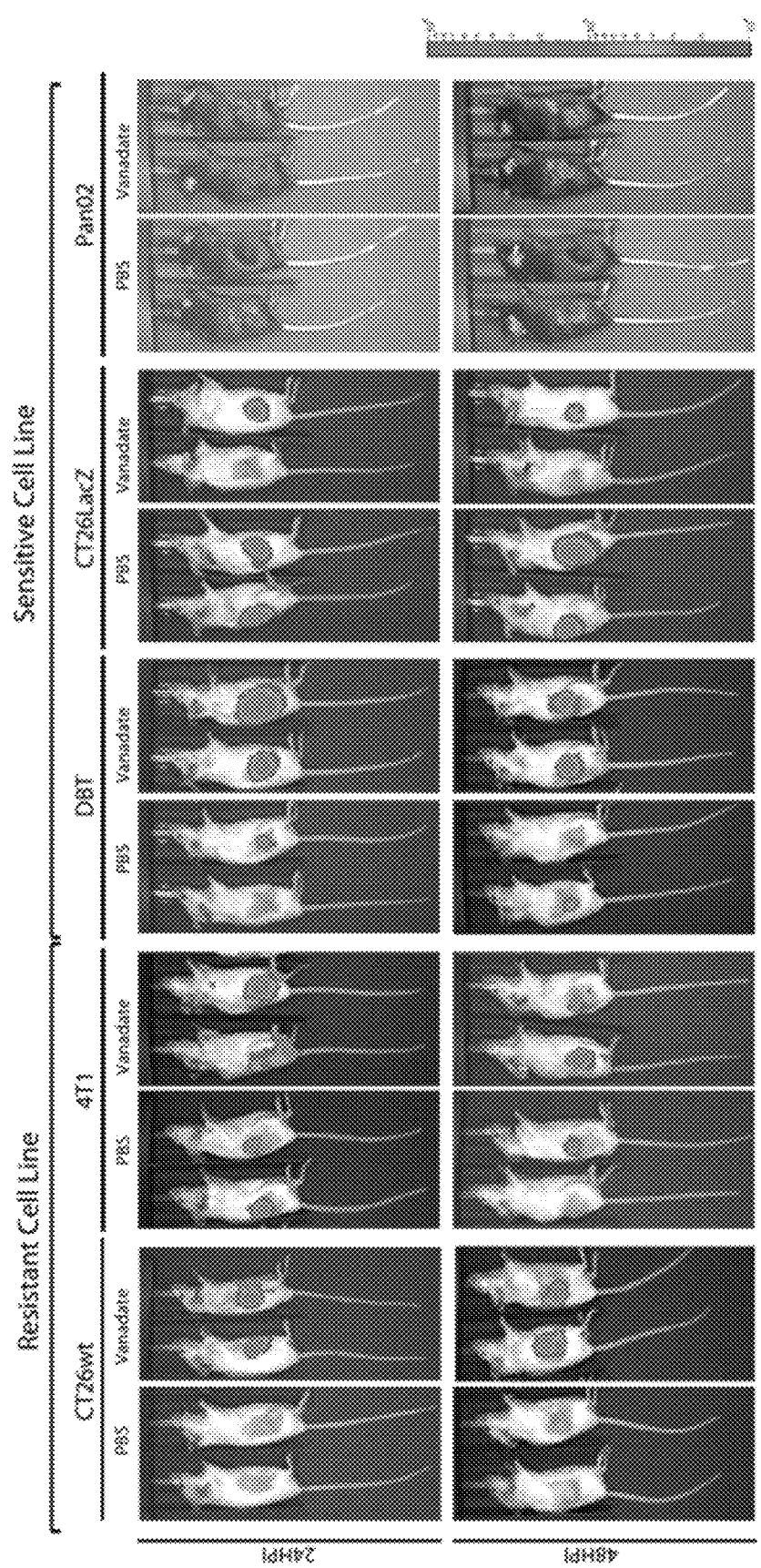
FIG. 4 shows results in which Vanadate increases VSVD51 infection in resistant syngeneic tumour models. (a) CT26 wt, CT26-LacZ, DBT, Pan02 tumour-bearing syngeneic mice were treated intratumorally with the vehicle (PBS) or 40 mg/kg of orthovanadate for 4 hours, and subsequently treated with 1×10$^8$ PFU of oncolytic VSVΔ51 expressing firefly-luciferase, intratumourally. 24 and 48 hour post infection, viral replication was monitored. Representative bioluminescence images of mice presented. (b) Quantification of luminescence. Scale represented in photons. (c) Schematic representation of treatment schedule for CT26 wt model. (d-f) Survival was monitored over time. Gehan-Breslow-Wilcoxon test indicates that the combined treatment is significantly prolonged over virus alone. (g) Survival was monitored after re-implantation of CT26WT in cured and naïve mice from (d)
Figure 4B:
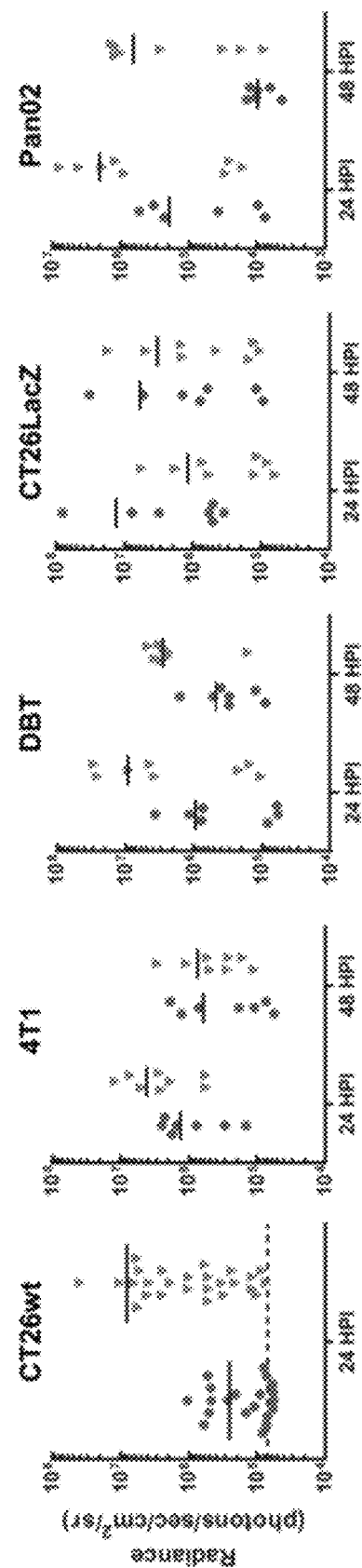
Figure 4:
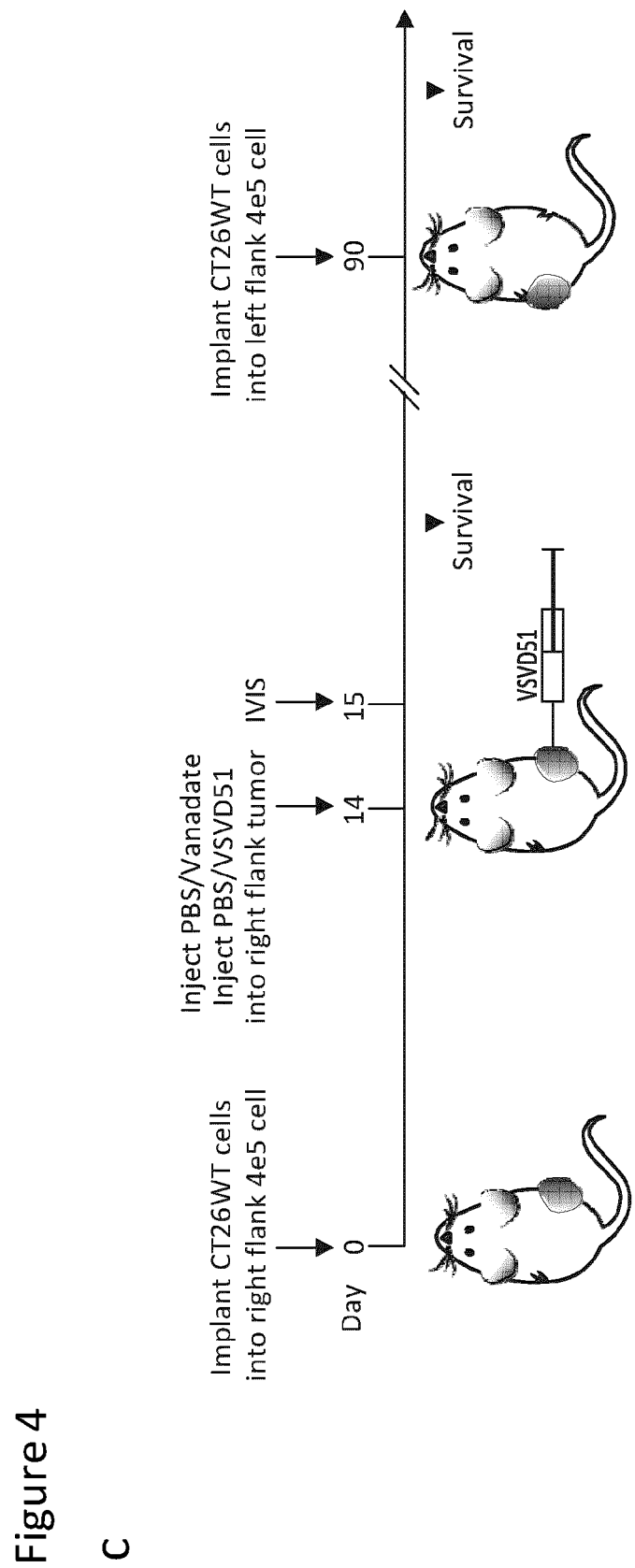
Figure 4:
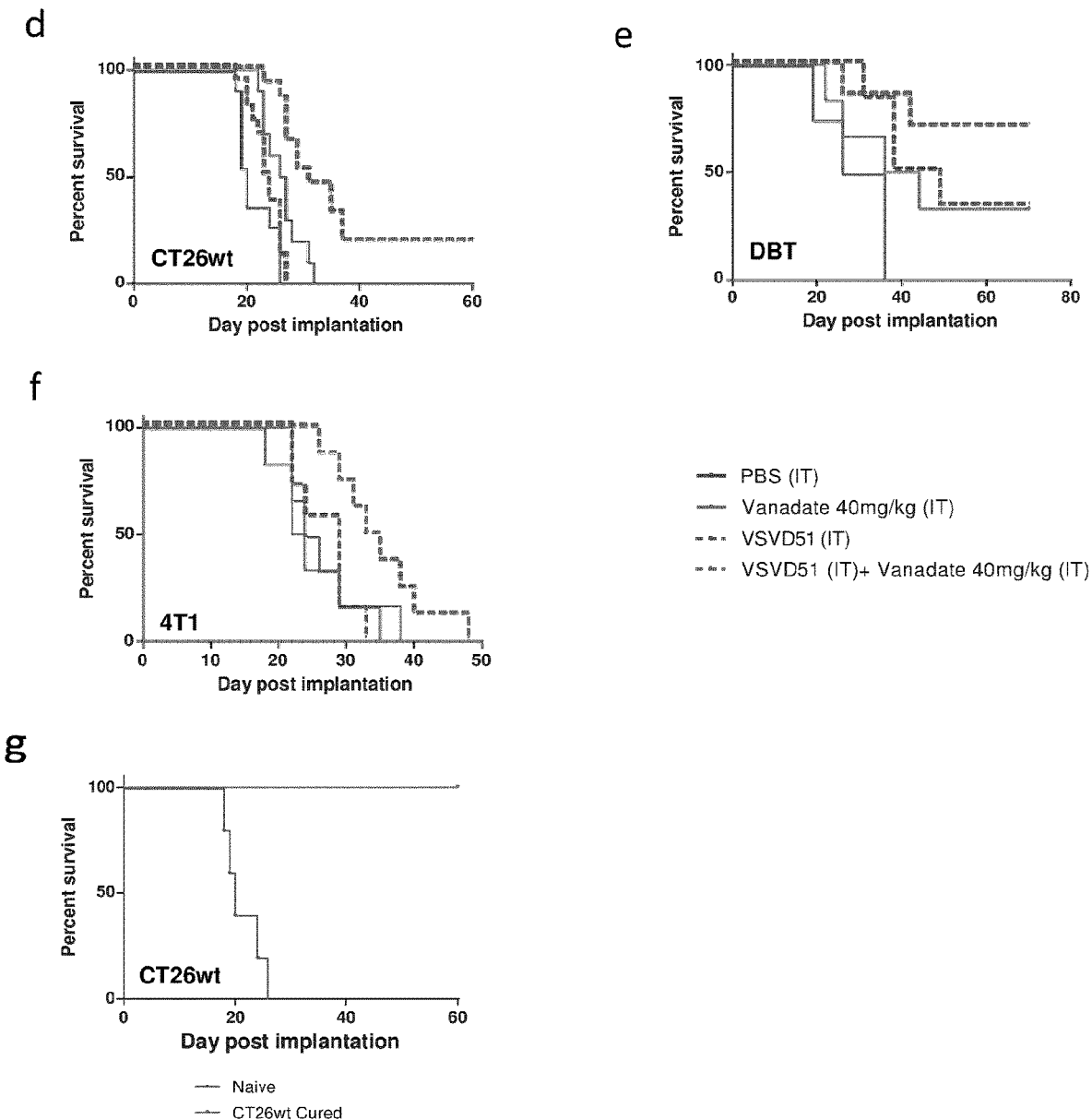
Figure 5:
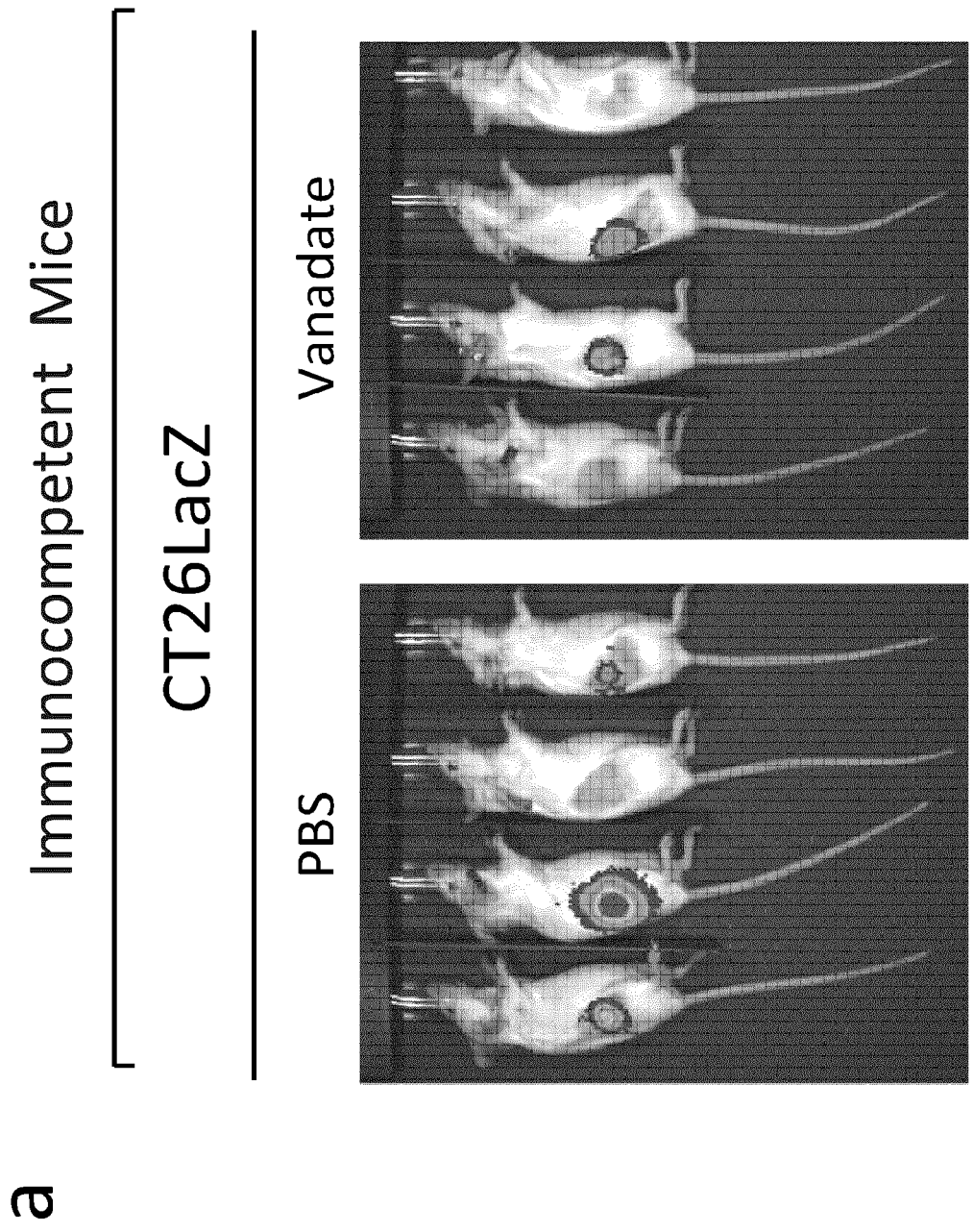
FIG. 5 shows results in which Vanadate and VSVD51 treatment leads to delay growth in distant tumor. (a,c) CT26-LacZ tumour-bearing immunocompetent mice and (b,d,e) CT26-LacZ or HT29 tumour-bearing nude mice were treated intratumorally with the vehicle (PBS) or 40 mg/kg of orthovanadate for 4 hours, and subsequently treated with 1×10$^8$ PFU of oncolytic VSVΔ51 expressing firefly-luciferase, intratumourally. 48 hour post infection, viral replication was monitored. (a,b) Representative bioluminescence images of mice presented. (c-e) Survival was monitored over time. (f) Schematic representation of treatment schedule for bilateral DBT. (g) Representative bioluminescence images of mice presented. (h) Growth of treated (right flank) and distant DBT tumors.
Figure 5:
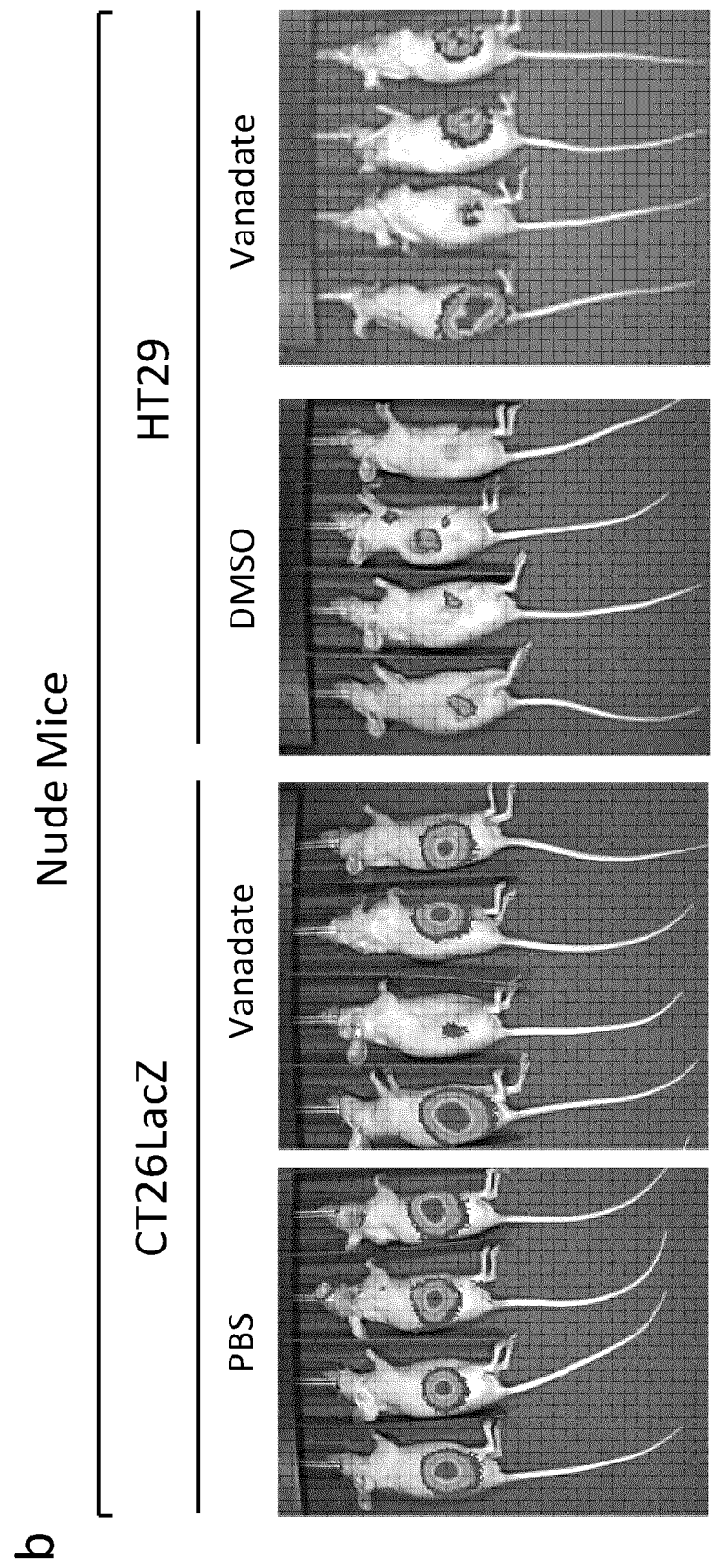
Figure 5:
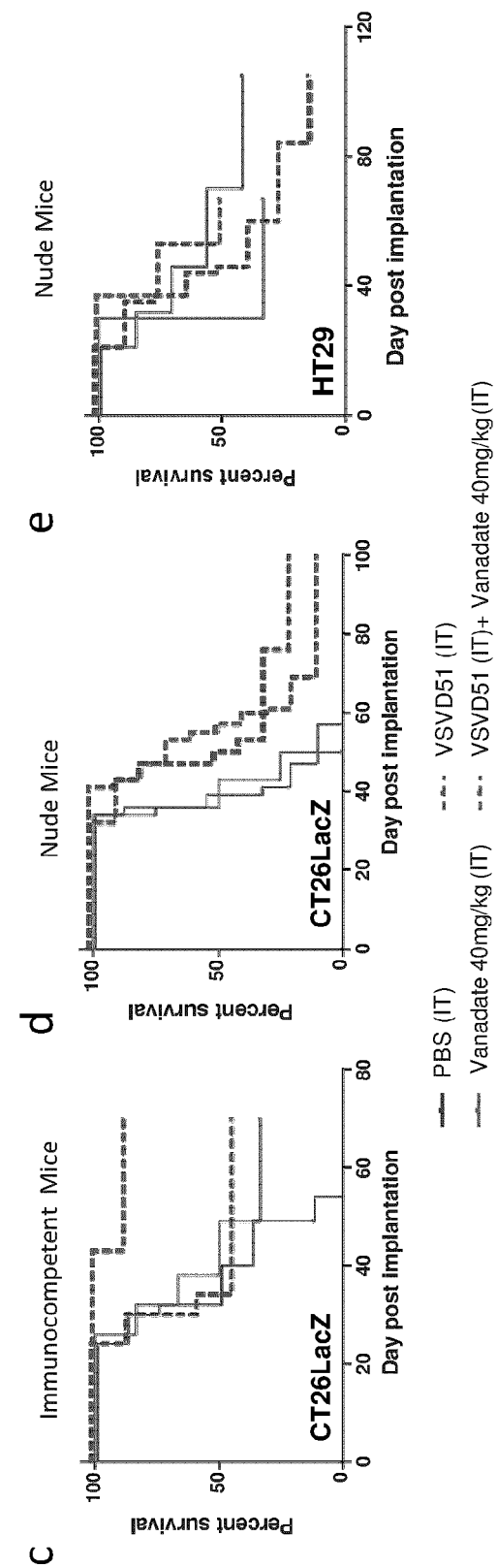
Figure 5:
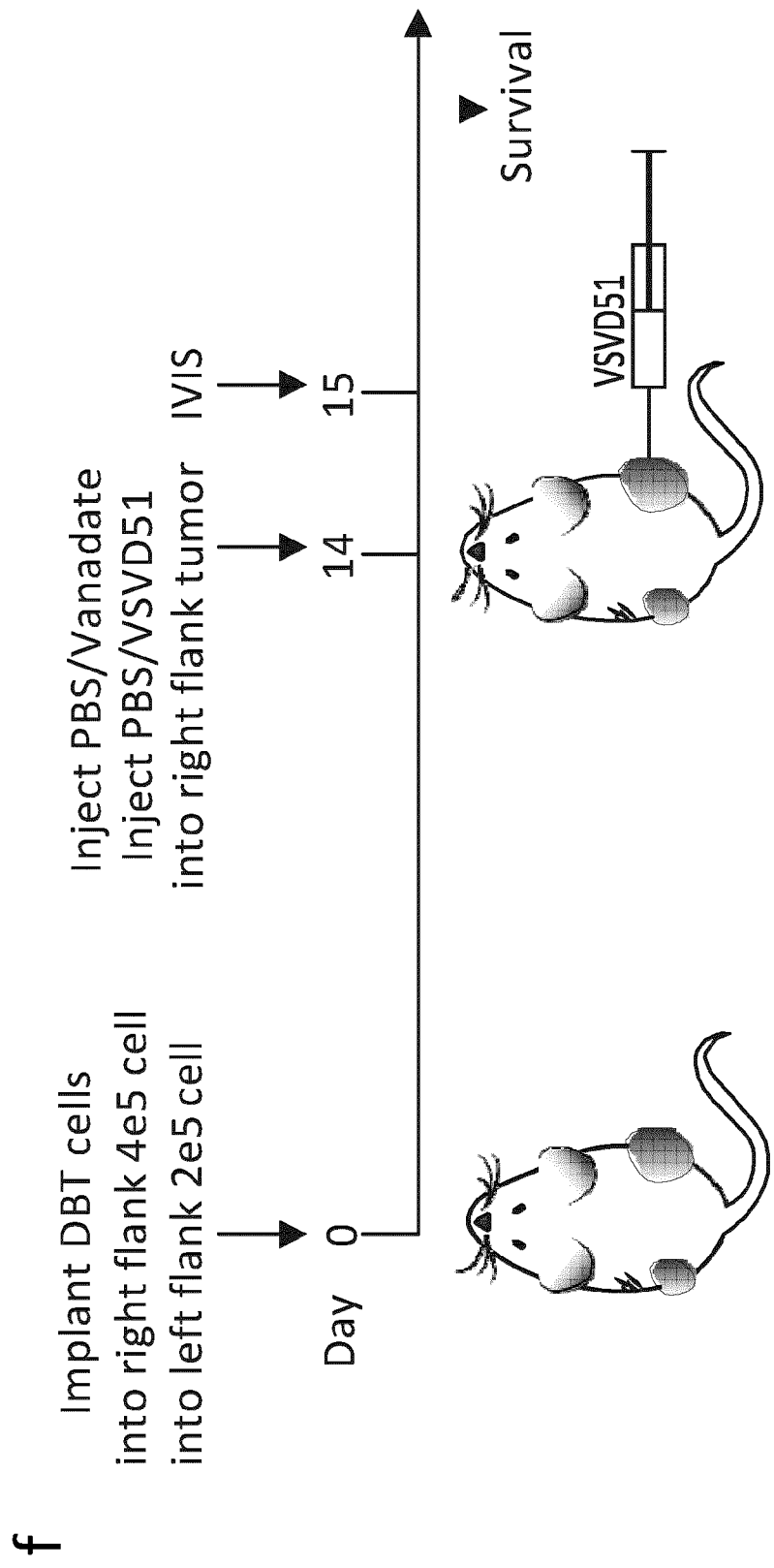
Figure 5:
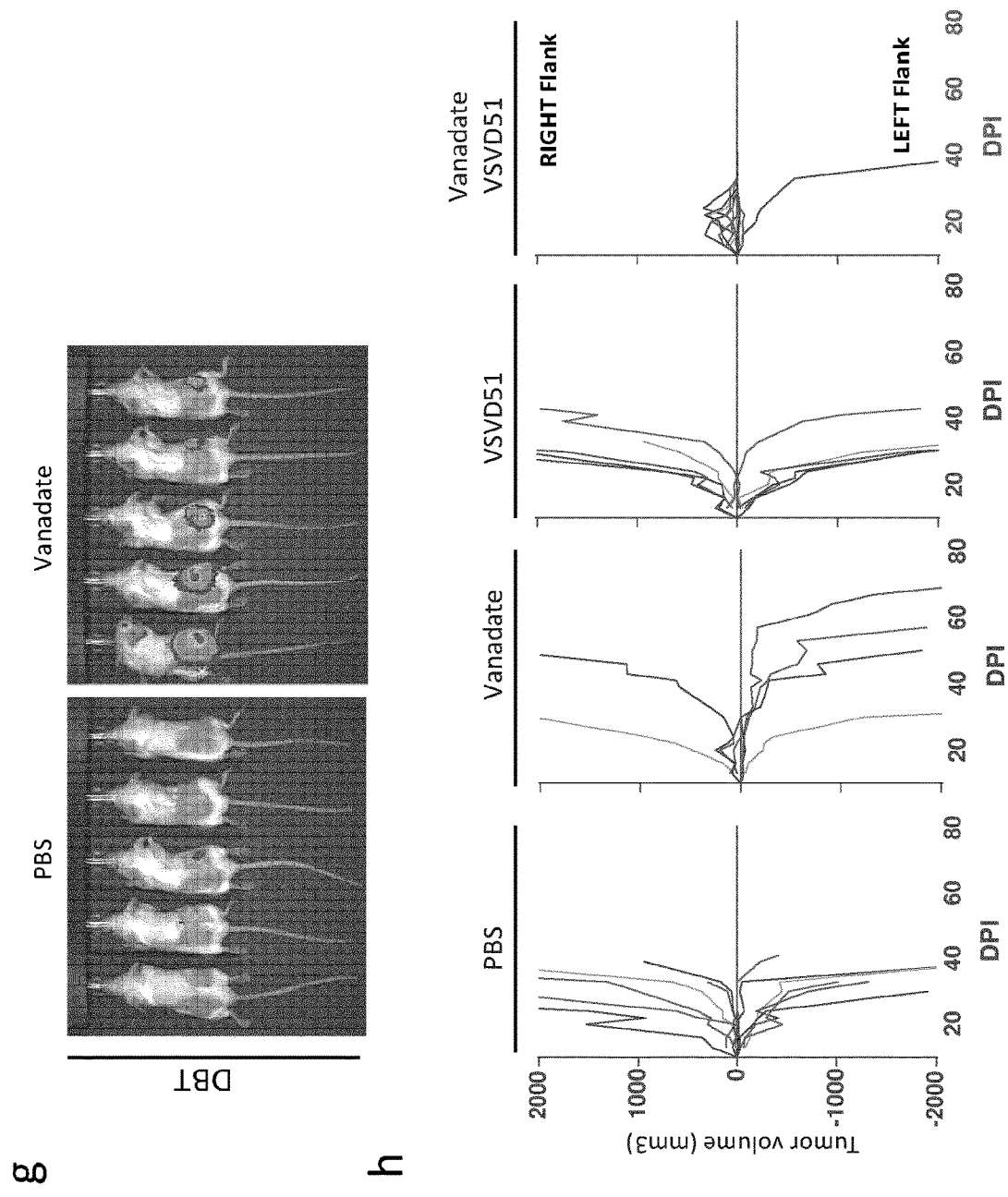
Figure 9:
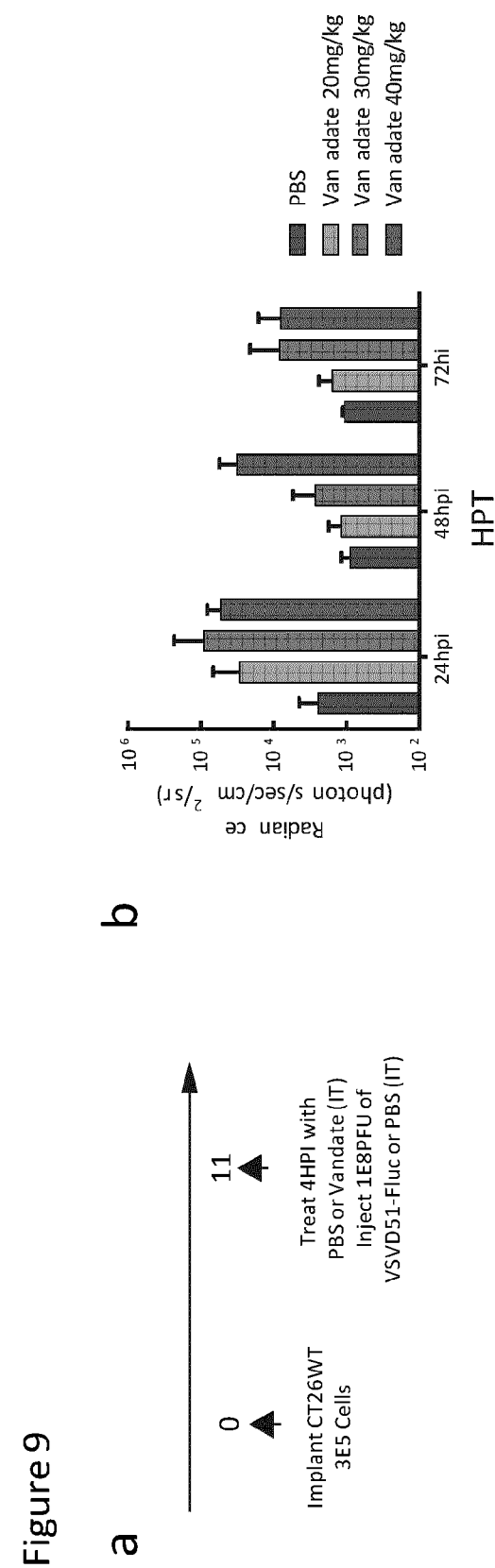
FIG. 9 shows results of optimization studies of Vanadate treatment in syngeneic tumour models. CT26 wt tumour-bearing syngeneic mice were treated intratumorally with the (a-c) vehicle (PBS), 20, 30 or 40 mg/kg of orthovanadate for 4 hours, and subsequently treated with $1 \times 10^8$ PFU of oncolytic VSVΔ51 expressing firefly-luciferase, intratumourally. 24, 48, 72 hour post infection, viral replication was monitored. (a) Treatment scheme. (c) Representative bioluminescence images of mice presented. (b) Quantification of luminescence. (d,e) To assess tolerability of orthvanadate at various pH, Balb/c mice were treated intraperitoneal with indicated concentration. Survival was monitored over time. (f) Same as (c) but were treated with indicated concentration of orthovanadate at different pH.
Figure 9C:
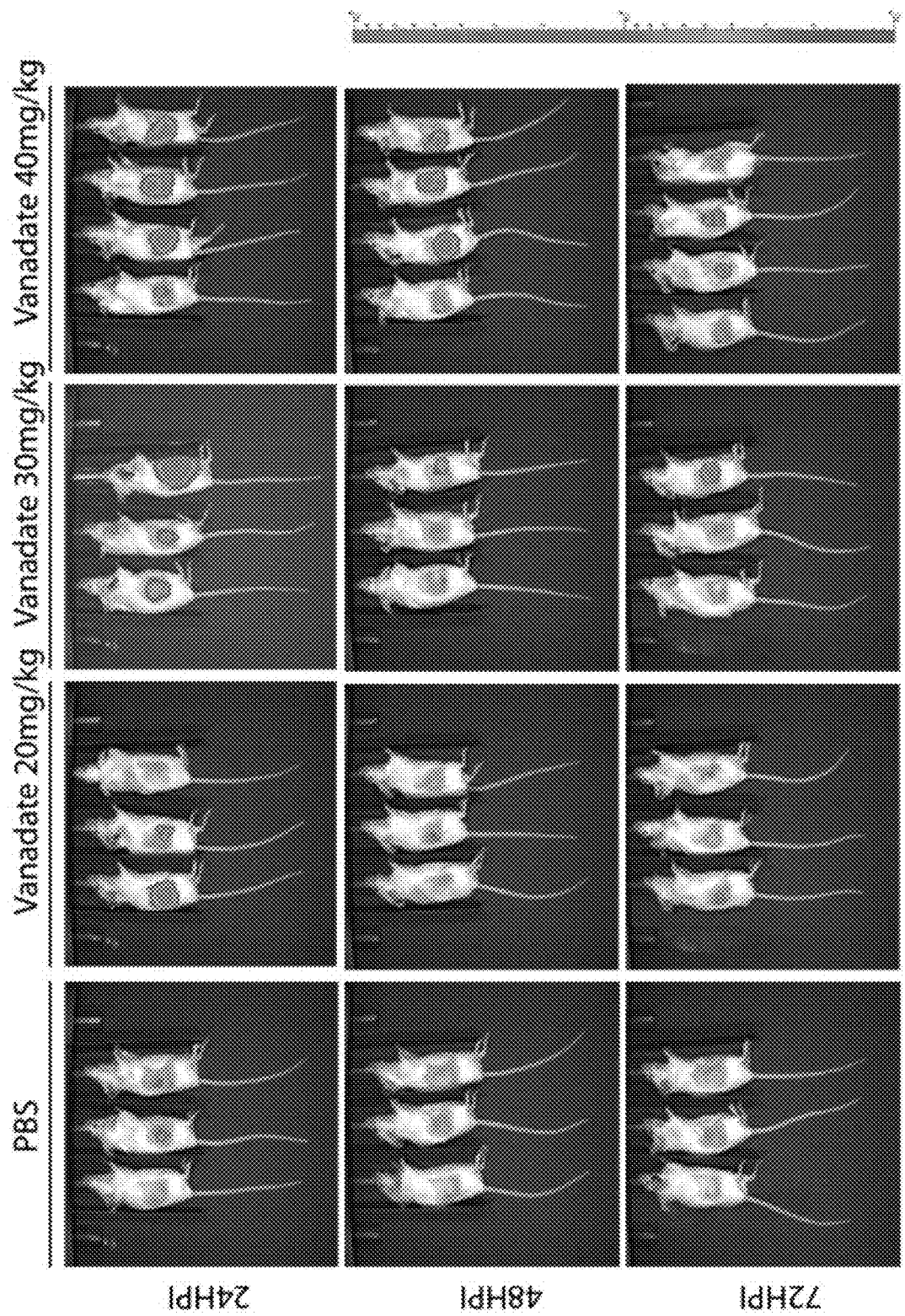
Figure 9:
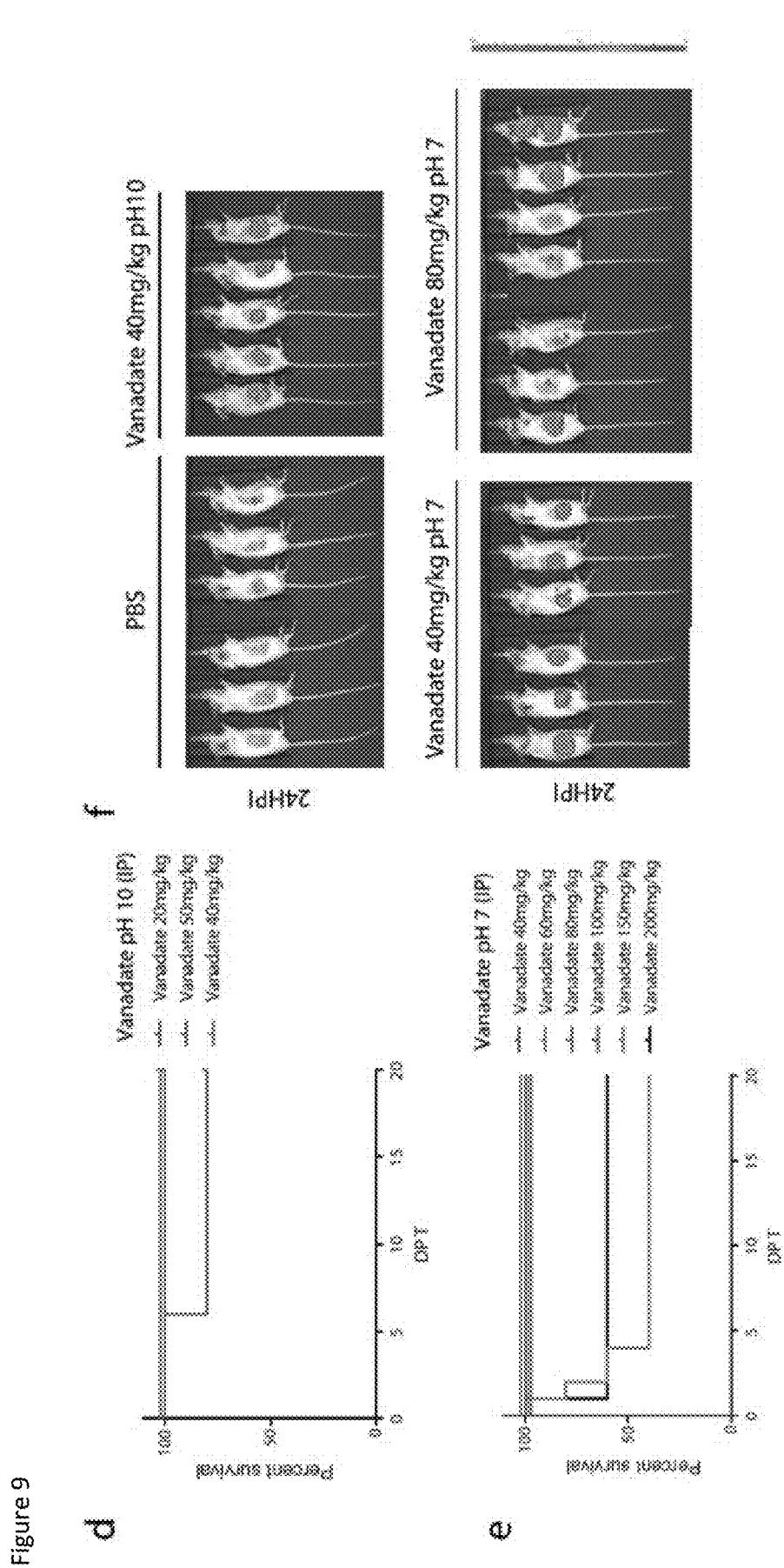
Figure 10:
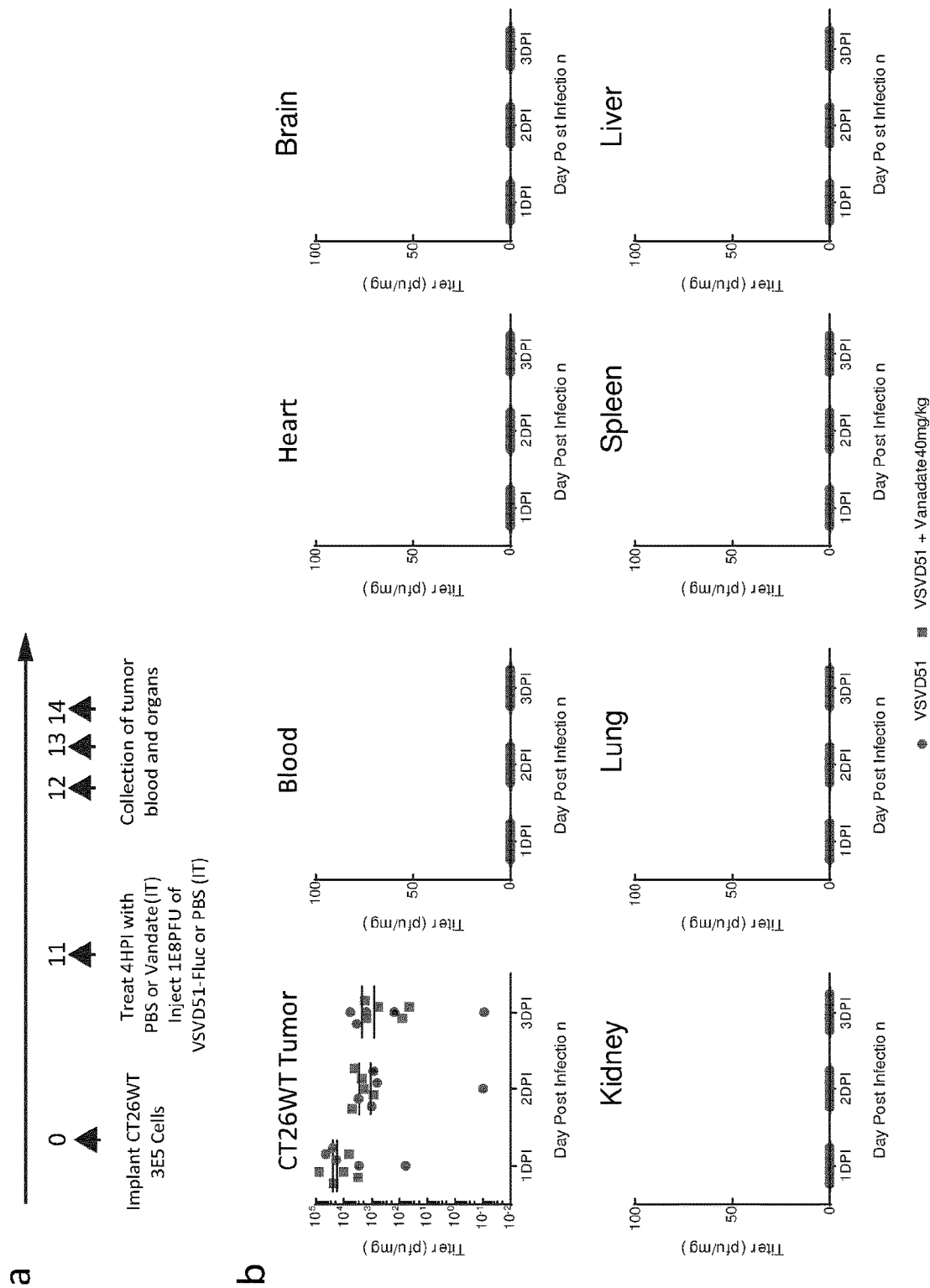
FIG. 10 shows results in which IT administration of vanadate with VSVD51 doesn't induce spread of virus to major organs. CT26 wt tumour-bearing syngeneic mice were treated intratumorally with the vehicle (PBS), 40 mg/kg of orthovanadate for 4 hours, and subsequently treated with $1 \times 10^8$ PFU of oncolytic VSVΔ51 expressing firefly-luciferase, intratumourally. Tumor and major organ were collected 1, 2, or 3 days post infection and homogenized prior to viral quantification by plaque assay. (a) Treatment scheme. (b) Corresponding viral titer presented.

Given the observation that vanadate enhanced both spread and oncolytic activity of VSVΔ51 in vitro, we wondered if the combination of VSVΔ51 and vanadate could have anti-cancer effects in animal models of cancer. Given reports in the literature suggesting vanadate has immunomodulatory properties, we performed experiments in a panel of immunocompetent syngeneic mouse models. FIG. 4a-b (FIG. 9a-b) show that direct injection of vanadate and VSVΔ51 expressing luciferase in CT26WT, 4T1 (breast cancer), DBT, and Pan02 (pancreatic cancer) tumors robustly enhanced virus-associated luciferase gene expression as assessed using an in vivo imaging system (IVIS). While evidence of toxicity was observed when using unbuffered orthovanadate, this was greatly reduced upon acidification of vanadate solution to pH 7 (FIG. 9d,e), which retained its activity (FIG. 9f) consistent with in vitro data (FIG. 2c). Additionally, bio-distribution studies showed that no virus was detected in major organs following infection in combination with orthovanadate (FIG. 10). This treatment regimen led to significantly improved survival of mice challenged with DBT, CT26WT, and 4T1 tumors compared to the monotherapies (FIG. 4c-f). In CT26WT, this led to complete remission in approximately 20% of mice (FIG. 4d), who subsequently became immune to re-challenge with the same cancer cells (FIG. 4g). One exception to this trend were CT26-LacZ tumors, which have been previously shown to be significantly more susceptible to infection using VSVΔ51 [50], where vanadate somewhat decreased virus-associated luminescence (FIG. 4a-b). However, the combination of vanadate and VSVΔ51 nevertheless led to a significant improvement of survival over the monotherapies in this model, reaching nearly 90% complete remissions (FIG. 5c). While enhanced bystander killing as observed in FIG. 3. could explain this phenomena to a certain extent, we wondered whether enhanced adaptive immune responses could play a role in generating such a high cure rate with a single intra-tumoral dose of vanadate and VSVΔ51. We therefore repeated these experiments with the CT26-LacZ tumors implanted in athymic nude mice that are devoid of T-cells. Remarkably, the enhancing effect of orthovanadate was completely abrogated in this context, albeit virus-associated luminescence was not generally affected (FIG. 5d). Similarly, while vanadate enhanced VSVΔ51 viral growth in human HT29 colon cancer cells implanted in nude mice (FIG. 5e), no improvements in survival were observed using the combination of vanadate and VSVΔ51 (FIG. 5e). To further evaluate the potential implication of an anti-tumor immune response, we implanted immunocompetent mice with bilateral DBT tumors and injected the right tumors only with the combination of VSVΔ51 and vanadate (or monotherapies/PBS) (FIG. 5f). Interestingly, we found that while enhancement of virus-associated luminescence was uniquely enhanced by vanadate in the injected tumors on the right side, the tumors on the left also shrunk following the combination therapy (FIG. 5g, h). While some tumors did regress following treatment with vanadate, this did not occur in the context of VSVΔ51 alone (FIG. 5h). Overall, this suggests that vanadate enhances the oncolytic activity of VSVΔ51 tumors in vivo, leading to the stimulation of a robust systemic antitumor immune response.

Example 5: Vanadate Potentiates an Immunogenic Response Following Infection

Figure 6:
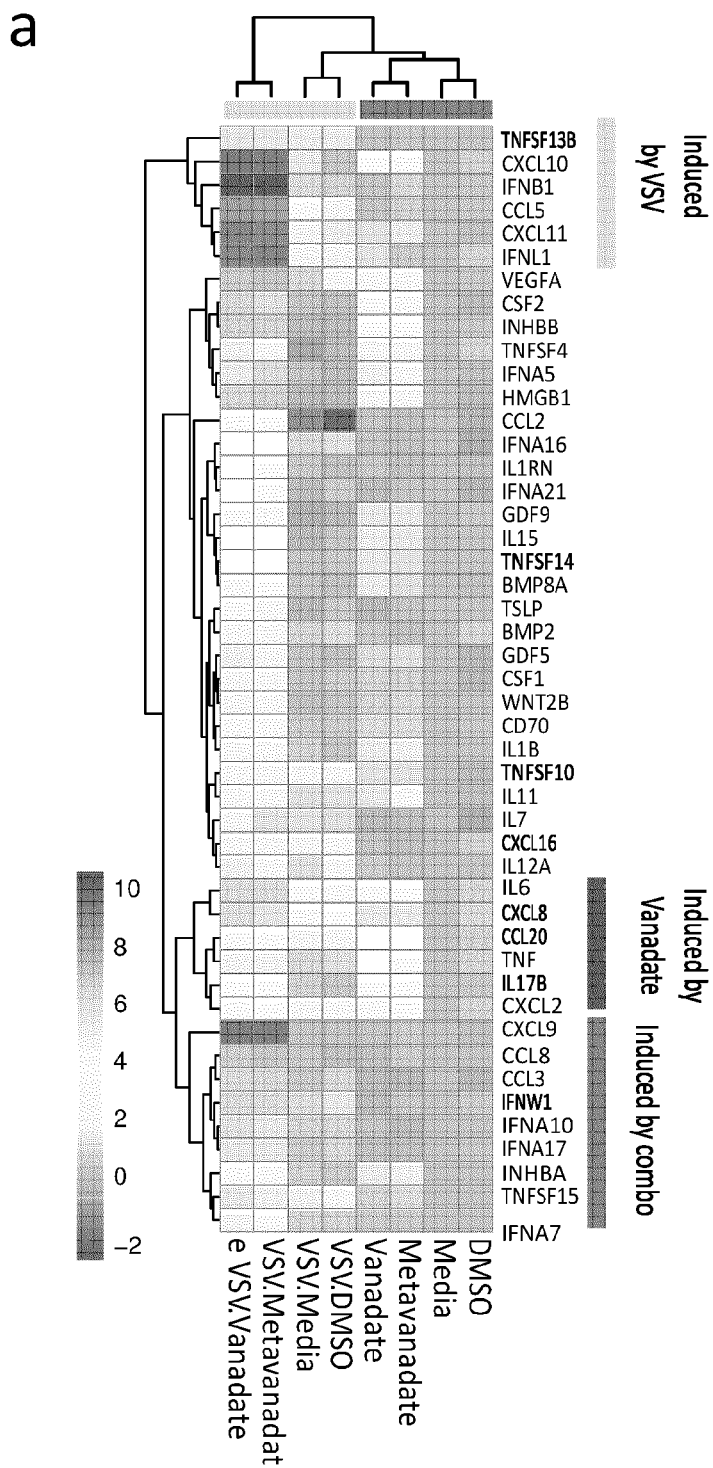
FIG. 6 shows results in which Vanadate potentiates stronger immune response after viral infection. (a,b) 786-0 and (b) CT26 wt cells were pretreated for 4 hours with the vehicle, orthovanadate, metavanadate or left untreated and infected with VSVD51 (MOI: 0.01), or left uninfected. 24 hours post infection RNA was extracted. (a) RNA was subsequently processed for hybridization on a Affymetrix Human PrimeView Array (N=1, pooled biological triplicate for each experimental condition), or processed for qPCR quantification. (a) Heatmap showing the expression levels of the differentially expressed cytokines and chemokines. Expression of genes was normalized to values obtained for untreated, uninfected control. Hierarchical clustering of genes from all samples was also performed. In the heatmap, red indicates relatively higher expression and blue indicates relatively lower expression relative to untreated, uninfected control. (b) Gene expression of various cytokines and chemokines in 786-0 and CT26 wt, quantified by qPCR. (c) Schematic representation of treatment schedule for CT26 wt model. (d) Percentage of the cells within the tumor that lymphocyte (CD45+), 10 days after treatment. (e) Absolute numbers of T-cell (CD3+ cell/million cells), 10 days after treatment. Mean+/−SEM is shown.
Figure 6:
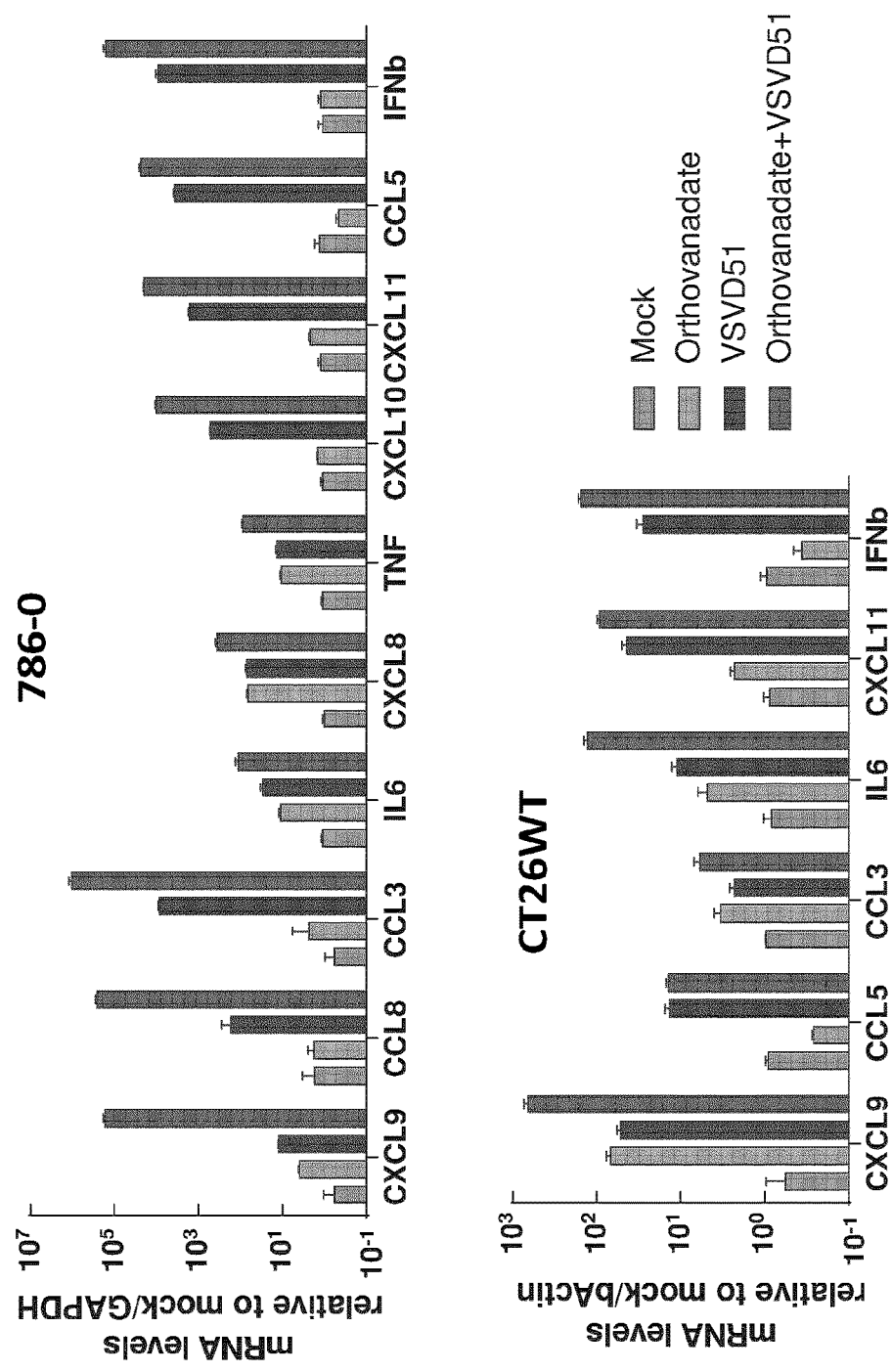
Figure 6:
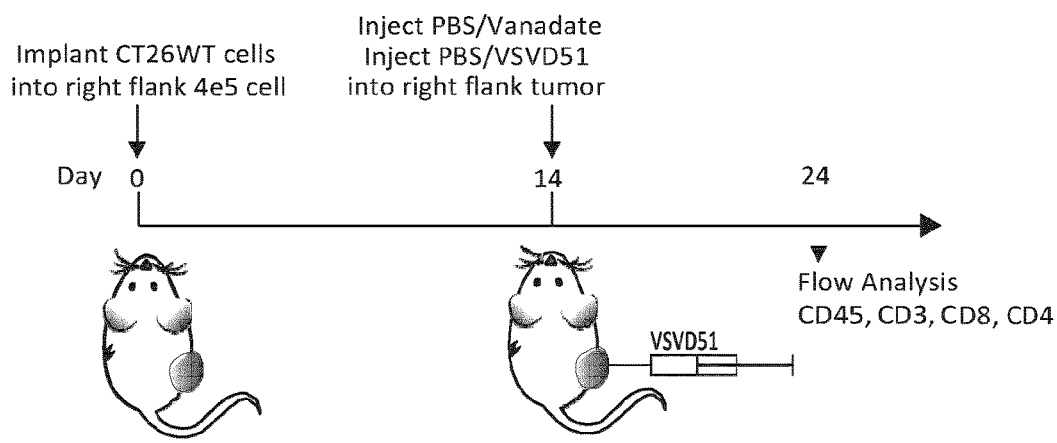
Figure 6:
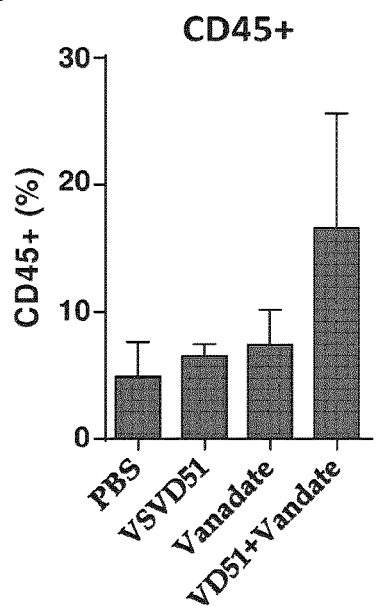
Figure 6:
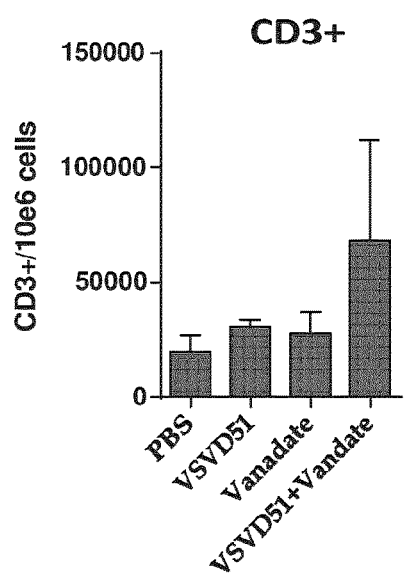
Figure 7A:
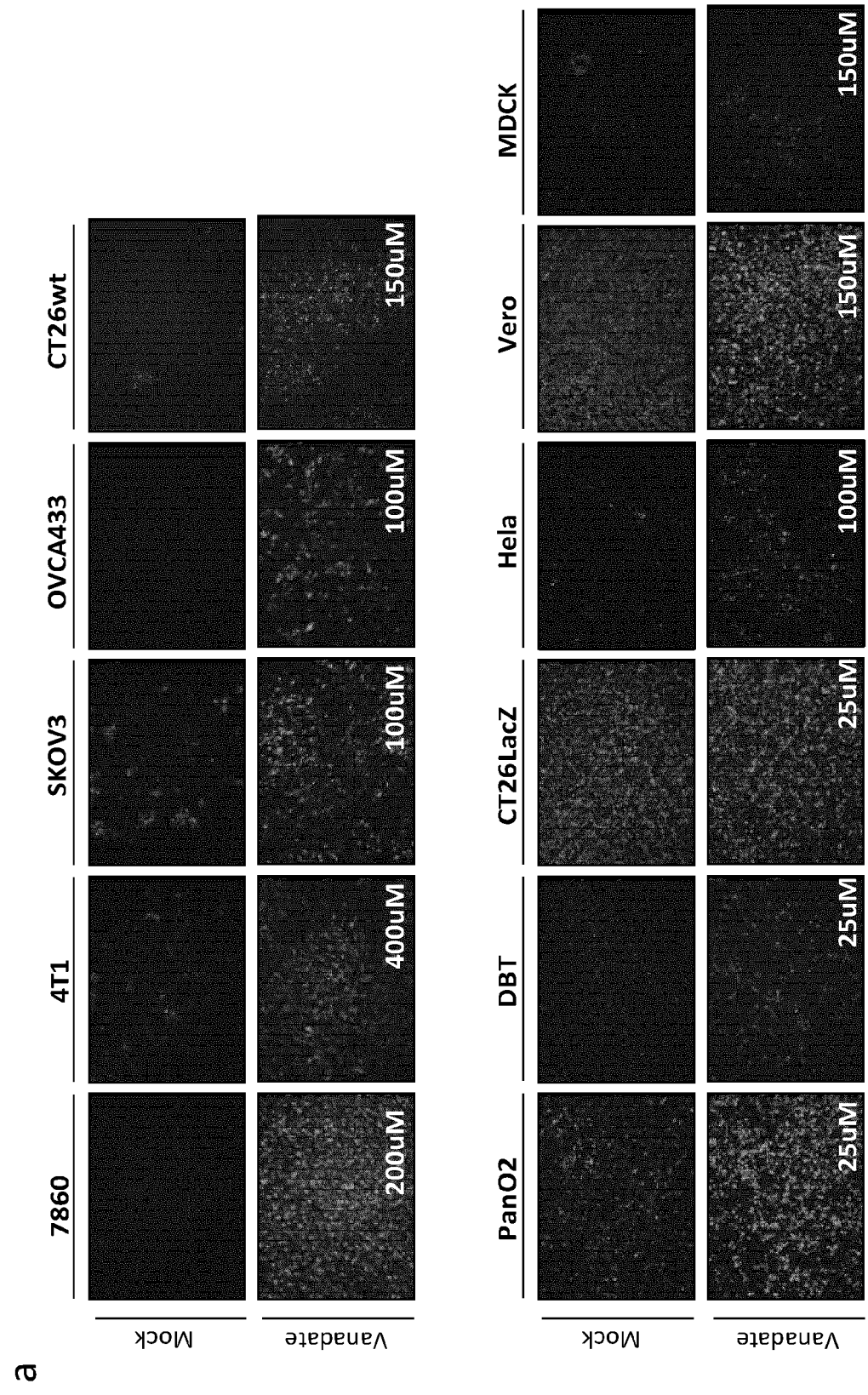
FIG. 7 shows results in which Vanadate enhances VSVD51 infection in resistant cancer cells. Various cancer cell lines were pretreated for 4 hours with the indicated concentration of orthovanadate and were subsequently infected with oncolytic VSVΔ51 expressing GFP at an MOI of 0.01. (a) Corresponding fluorescent images are presented (b) and viral titer were determined 24 hours post infection from supernatants (N=3)
Figure 7:
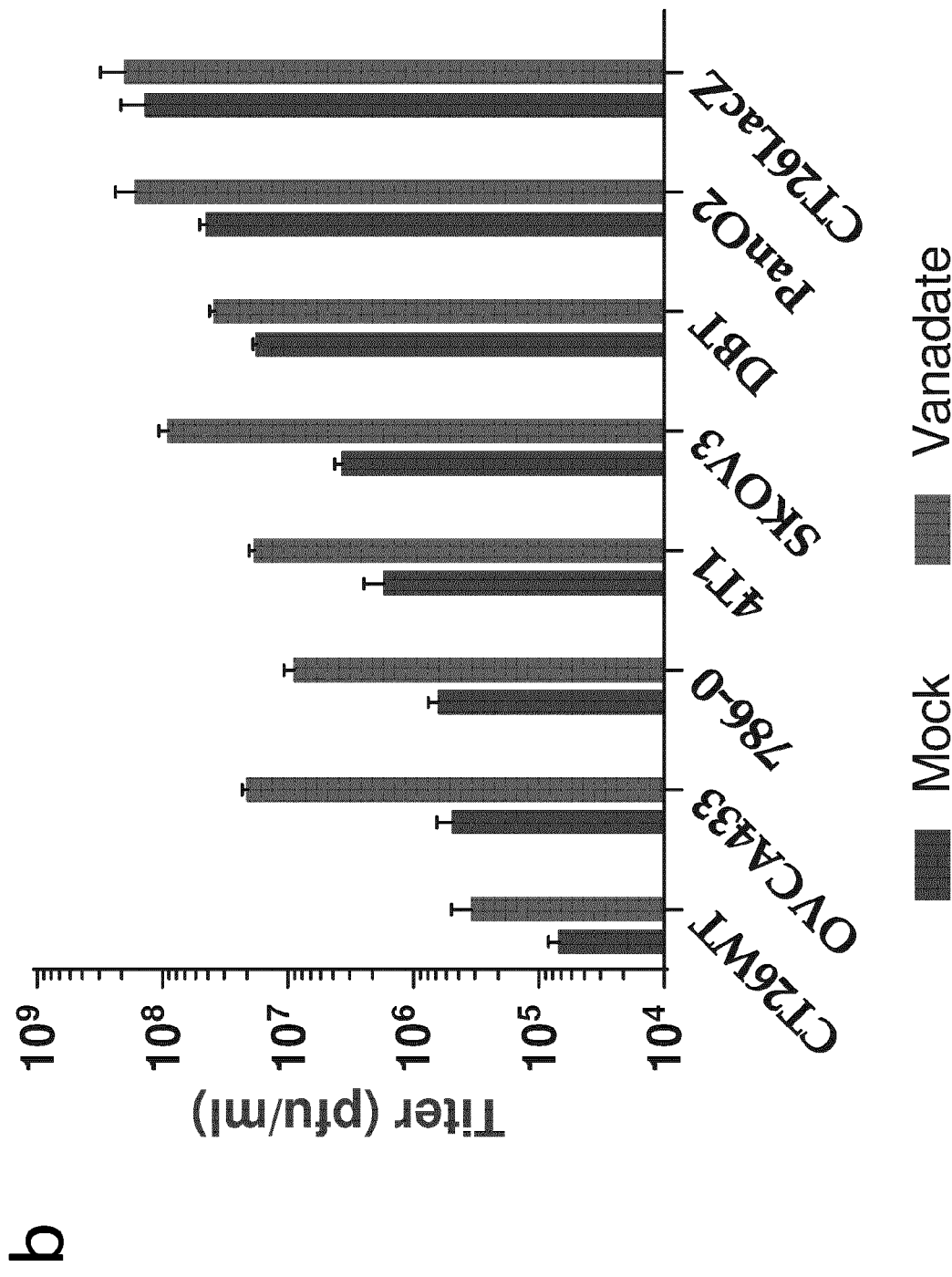
Figure 8:
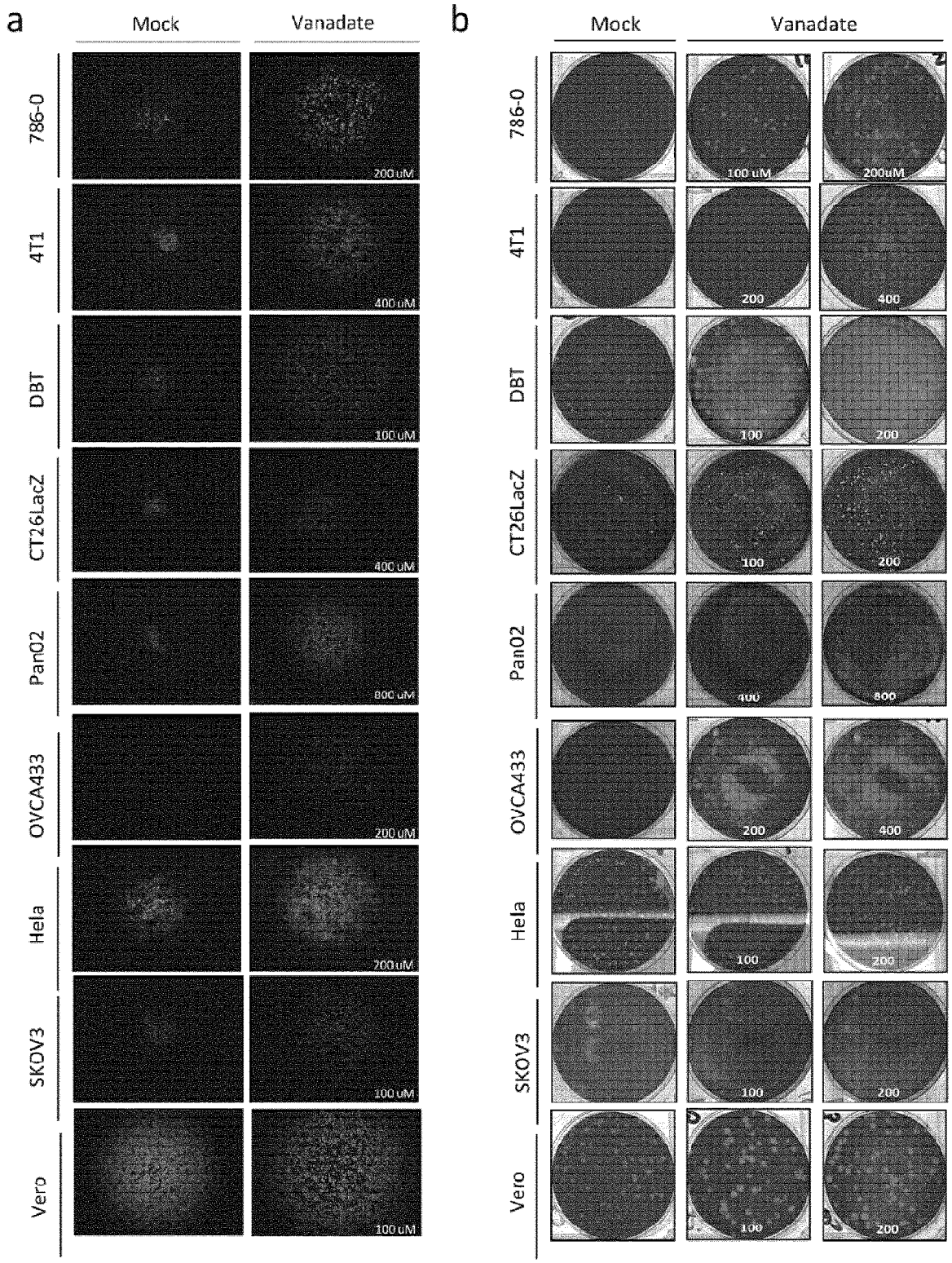
FIG. 8 shows results in which Vanadate enhances VSVD51 spread in cancer cells. Various cancer cell lines were pretreated for 4 hours with the indicated concentration of orthovanadate and were subsequently infected with oncolytic VSVΔ51 expressing GFP for, an agarose overlay was added after 1 hour of infection. (a) Fluorescence microscopy of a representative plaque 24 hour after infection. (b) Corresponding coomassie blue stain of the full wells in (a) illustrating the enhancement of the plaque diameters in presence of orthovanadate.
Figure 11:
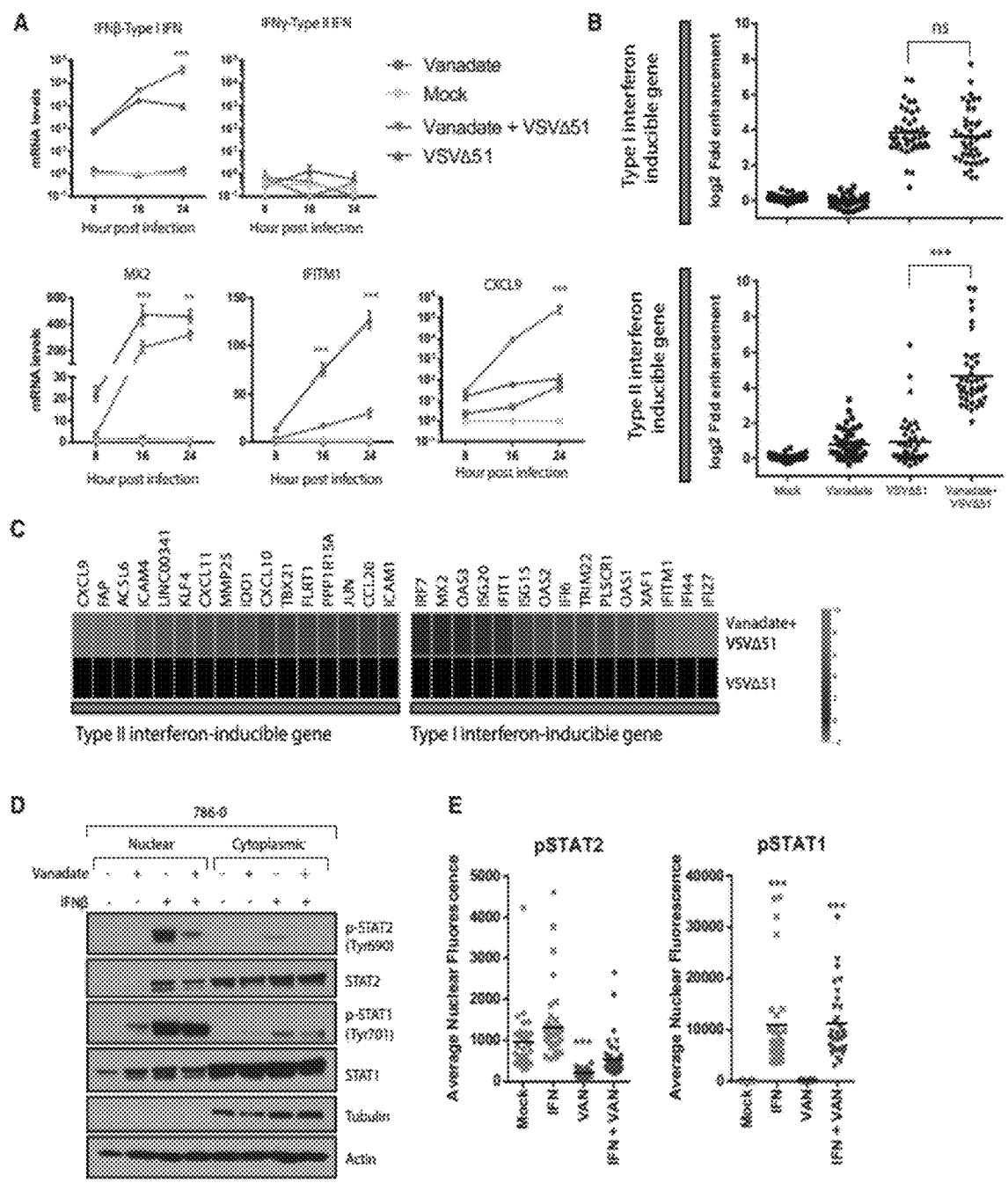
FIG. 11 shows results in which Vanadate inhibits the type I Interferon response and potentiates a proinflammatory response via type II interferon. Cell lysates of 786-0 treated with vanadate and VSVΔ51 expressing GFP were collected at indicated time points. RNA was extracted and probed for expression of (a) ifnβ, ifnγ, mx2, ifitm1 and cxcl9 genes by qPCR (N=3; Error bars indicate SEM; $p<0.01$, *$p<0.0001$ by 2 way ANOVA; comparing the VSVΔ51 condition to the Vanadate+VSVΔ51 condition). (b) RNA was used for gene expression microarray analysis. Data is normalized to untreated control, indicating log 2 fold change in gene expression of genes documented to be induced by Type I or Type II IFN. (Bars indicate mean; 1-way ANOVA; NS, no statistical significance, *** $p<0.0001$, comparing combination treatment to virus alone condition), (c) Heatmap showing the expression levels of the differentially expressed IFN stimulated genes. Expression of genes was normalized to values obtained for mock-treated, infected control. Color scale indicates log 2 fold change. (d) 786-0 cells were pretreated with vanadate (1000 μM) for 4 hours and challenged with IFNβ (100 U/ml). One hour later, fractionated cell lysates were probed for pSTAT1, STAT1, pSTAT2, STAT2 and actin. (e) Immunofluorescence for pSTAT1, pSTAT2 and STAT2 was performed in 786-0 cells treated with vanadate (1000 μM) for 4 hours and with human IFNβ (1000 U) for 1 hour. Quantification of the average nuclear fluorescence associated to pSTAT1 or pSTAT2 in each condition (N=30; Bars indicate mean; 1-way ANOVA, * $p<0.05$,  $p<0.001$, * $p<0.0001$, as compared to the mock condition counterpart)
Figure 12:
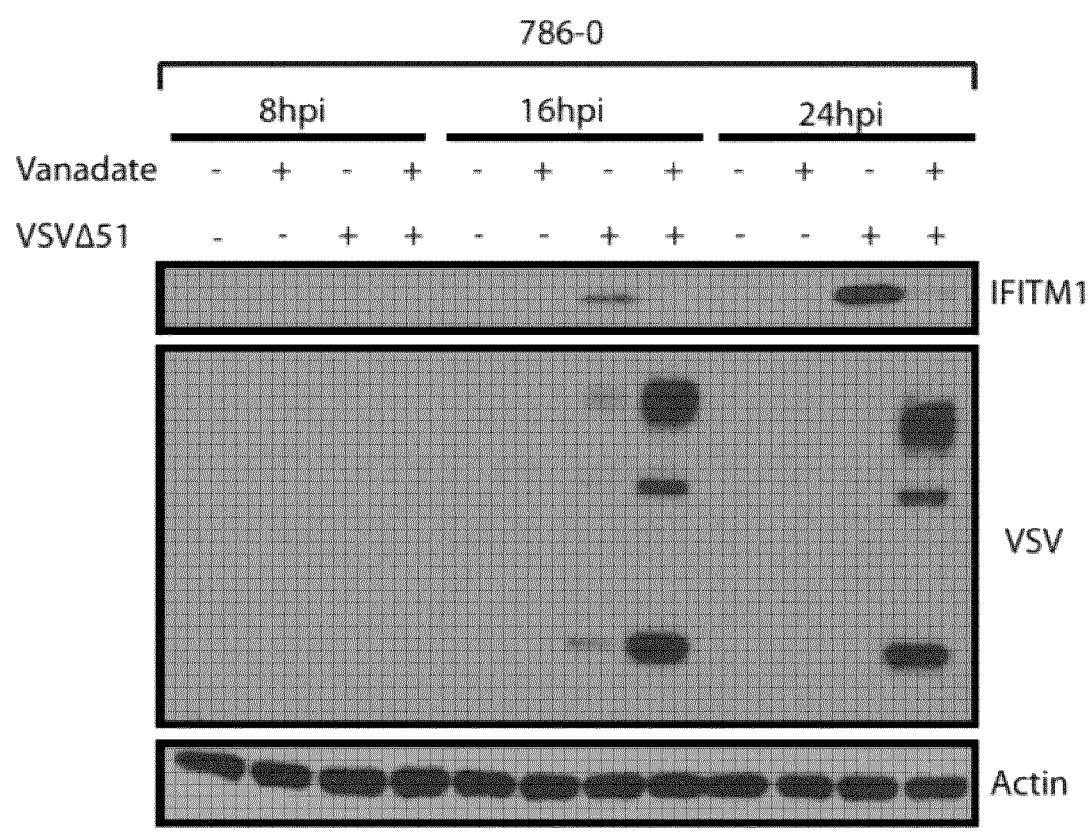
FIG. 12 shows results in which Vanadate decreased protein expression levels of genes induced by Type I IFN. Cell lysates of 786-0 treated with vanadate and VSVΔ51 expressing GFP was collected at indicated time points. Protein was extracted and probed for IFITM1, VSV and actin by western blot.

To gain insight on how combination treatment with vanadate and VSVΔ51 could lead to robust anti-tumor immunity, we used gene expression microarrays took at the impact of VSVΔ51 and Vanadium-based compounds (orthovanadate and metavanadate), alone or in combination, on gene expression profiles 24 h post infection of 786-0 cells. In line with our demonstration that vanadate stimulates an anti-tumor immune response, gene set-enrichment analyses using GOrilla revealed that vanadate alone induced inflammatory responses, and immune system processes; which were further potentiated in combination with VSVΔ51. Uniquely, the infection of vanadate treated cells led to the increased expression of a number of proinflammatory cytokines (CCL8, CCL3, IL6, TNF, IFNβ, CCL5) and many genes typically induced by type II IFN (IFNγ), including chemokines such as CXCL9, CXCL10, and CXCL11 (FIG. 11b,c and FIG. 6a,b). Among others, CXCL9 plays a key role in leukocyte trafficking and its mRNA was up-regulated by more than 100,000 fold during viral infection of vanadate-treated cells compared to mock (FIG. 6a, b, FIG. 11a). We further validated the vanadate-mediated increase in mRNA expression of IFNγ induced chemokines such as CXCL9 in mouse CT26WT cells which were used for our in vivo models, as well as its secretion by ELISA in various human cancer cell lines (FIG. 6b) While many genes typically induced by IFNγ were up-regulated upon infection of vanadate-treated cells, IFNγ itself was not up-regulated at any time-point post infection under any condition tested in 786-0 (FIG. 11a,b). On the other hand, IFNβ mRNA was up-regulated by more than 10-fold 24 h following infection (FIG. 11a) in vanadate treated cells compared to mock. Surprisingly, genes typically induced by Type I IFN were either unaffected or decreased in these conditions (FIG. 11b,c). Indeed, genes induced by Type I IFN, such as MX2 and IFITM1 with known antiviral function against rhabdoviruses, were robustly downregulated as early as 8 h post-infection (FIG. 11a). Furthermore, protein expression levels of IFITM1 was potently repressed by vanadate in infected cells 16 and 24 h following infection (FIG. 12). The synergistic up-regulation of CXCL9 was also observed in CT26WT colon cancer cells (FIG. 6b) for which combination treatment with orthovanadate potentiated close to 20% complete remissions in syngeneic mice. In this model, it was found that combination treatment lead to increased accumulation of T-cells within the tumor (FIG. 6c, d).

Importantly, IFNβ and IFNγ bind to distinct receptors and lead to differential activation of STAT1 and STAT2 (Signal Transducer and Activator of Transcription) transcription factors. Phosphorylation of STATs leads to their dimerization and nuclear translocation to activate transcription of IFN-stimulated genes (ISGs). Some of these genes are regulated by both type I and type II IFNs, whereas others are selectively regulated by one or the other. Type I IFNs induce the phosphorylation of both STAT1 and STAT2, leading to the formation of the ISGF3 complex composed of a STAT1-STAT2 heterodimer and IRF9 that binds specific promoter regions known as IFN-stimulated response elements (ISREs); while type II IFN primarily induce the phosphorylation of STAT1, leading to the formation of STAT1-STAT1 homodimers that bind IFNγ-activated-sequence (GAS) elements (Mechanisms of type-1 and type-ii-interferon-mediated signaling, Plantanias, LC, Nat Rev Immunol, 2005). Consistent with a shift from a type I towards a type II IFN response, vanadate treatment inhibited the IFNβ-induced phosphorylation of STAT2 and reduced its nuclear accumulation but did not similarly affect STAT1 as observed by Western blot (FIG. 11d). Supporting this idea, immunofluorescence also revealed that whereas activated STAT1 translocated to the nucleus following infection of vanadate-treated cells, STAT-2 remained mostly in the cytoplasm (FIG. 11e). Remarkably, this suggests, without wishing to be bound by theory, that vanadate enhances OV activity through a previously unappreciated mechanism that converts a predominantly antiviral type I IFN response into a type II IFN response, through the preferential repression of STAT2 activation. This signal "rewiring" may lead to up-regulation of proinflammatory cytokines and chemokines that favour the generation of a T cell dependent anti-tumor response.

Clustering analyses (FIG. 6a) revealed a subset of genes encoding for secreted proteins that were either induced by vanadium compounds, VSVΔ51, or the combination of the both as compared to mocks. Consistent with immunomodulation, treatment of cells with vanadium-based compounds led to the up-regulation of multiple cytokines, most prominently IL6, CXCL8, CCL20, TNF, IL17B and CXCL2. As expected, VSVΔ51 infection also led to the up-regulation of multiple but different sets of cytokines including TNFSF13B, CXCL10, IFNB1, CCL5, CXCL11, and IFNL1. With the exception of TNFSF13B, these same cytokines were substantially more highly expressed in VSVΔ51-infected cells co-treated with vanadium-based compounds, consistent with increased viral infection resulting from vanadium compound treatment in these cells (FIG. 1c). Importantly, the combination of VSVΔ51 and vanadium compounds led to the up-regulation of multiple cytokines not up-regulated by either VSVΔ51 or vanadium compounds used as single agents. Most significantly, this includes cytokines such as CXCL9, CCL8, CCL3, IFNW1, IFNA10, IFNA17, INHBA, TNFSF15, and IFNA7. Realtime PCR validation of gene expression data revealed that T-cell chemoattractants such as CXCL9 were vastly up-regulated (over 100,000× over VSVΔ51 alone) in 786-0 cells upon combination treatment with orthovanadate (FIG. 6b).

Materials and Methods

Drugs, Chemicals and Cytokines.

Drugs, chemicals and cytokines and their respective supplier and solvent used in this study are listed below.

| Name | Formula | Abbreviation | Solvent | Supplier |
| --- | --- | --- | --- | --- |
| Sodium orthovanadate | $Na_3VO_4$ | vanadate | Water | Sigma-Aldrich (St. Louis, Missouri) |
| Ammonium metavanadate | $NH_4VO_3$ | metavanadate | Water | Sigma-Aldrich (St. Louis, Missouri) |
| Vanadium(IV) oxide sulfate hydrate | $VOSO_4 \cdot xH_2O$ | VS | Water | Sigma-Aldrich (St. Louis, Missouri) |
| Vanadium(V) oxytriethoxide | $OV(OC_2H_5)_3$ | VOx | DMSO | Sigma-Aldrich (St. Louis, Missouri) |
| Bis(maltolato) oxovanadium(IV) | $C_{12}H_{10}O_7V$ | BMOV | DMSO | Sigma-Aldrich (St. Louis, Missouri) |
| Vanadium(III) bromide | $VBr_3$ | $VBr_3$ | Water | Sigma-Aldrich (St. Louis, Missouri) |
| Vanadium(IV) fluoride | $VF_4$ | $VF_4$ | Water | Santa Cruz (Dallas, Texas) |
| potassium permanganate | $KMnO_4$ | $KMnO_4$ | Water | Sigma-Aldrich (St. Louis, Missouri) |
| Chromium(VI) oxide | $CrO_3$ | $CrO_3$ | Water | Sigma-Aldrich (St. Louis, Missouri) |

| Name | Formula | Abbreviation | Solvent | Supplier |
|---|---|---|---|---|
| L-Ascorbic acid | $C_6H_8O_6$ | L-AA | Water | Sigma-Aldrich (St. Louis, Missouri) |
| Tiron | $(OH)_2C_6H_2(SO_3NO_2 \cdot H_2O)$ | Tiron | Water | Sigma-Aldrich (St. Louis, Missouri) |
| Potassium Phosphate | $K_2HPO_4$ | $K_2HPO_4$ | Water | |
| Sodium phosphate monobasic monohydrate | $NaH_2PO_4\ H_2O$ | $NaH_2PO_4\ H_2O$ | Water | |
| Sodium phosphate dibasic anhydrous | $NaHPO_4$ | $NaHPO_4$ | Water | |
| Sodium phosphate monobasic anhydrous | $NaH_2PO_4$ | $NaH_2PO_4$ | Water | |
| Tetrasodium pyrophosphate | $Na_4P_2O7$ | $Na_4P_2O_7$ | Water | |
| D-Luciferin, potassium salt | $C_{11}H_7KN_2O_3S_2$ | Luciferin | PBS | Biotium (Hayward, California) |
| Human IFN 2a alpha | | hIFNa | PBS | Sigma-Aldrich (St. Louis, Missouri) |
| Human | | hIFNb | PBS | PBL (Piscataway, NJ) |

Cell Lines.

CT26 wt (colon), CT26-LacZ (colon), DBT (astrocyte) and Pan02 (pancreatic) mouse cancer cells; 786-0 (renal), SKOV3 (ovarian) human cancer cells; Vero monkey kidney cells; and GM-38 normal human fibroblasts were obtained from the American Type Culture Collection (Manassas, Va.). Cells were cultured in HyQ high-glucose Dulbecco's modified Eagle's medium (Hyclone, Waltham, Mass.) supplemented with 10% fetal calf serum (CanSera, Etobicoke, Ontario, Canada). All cell lines were incubated at 37° C. in a 5% $CO_2$ humidified incubator.

Viruses and Quantification.

The Indiana serotype of VSV (VSVD51 or wild type) was used throughout this study and was propagated in Vero cells. VSVD51-expressing GFP or firefly luciferase are recombinant derivatives of VSVD51 described previously[37]. All viruses were propagated on Vero cells and purified on 5-50% Optiprep (Sigma, St Louis, Mo.) gradient and all virus titres were quantified by the standard plaque assay on Vero cells as previously described[38].

Cell Viability Assay.

The metabolic activity of the cells was assessed using alamarBlue (Bio-Rad, Mississauga, ON) according to the manufacturer's protocol. Treated and/or infected cells in a 96-well plate (Corning, Manassas, Va.) were treated, at indicated time, with 10 uL of alamar blue in each well and incubated for 2 to 4 hours. Fluorescence was measure at 590 nm upon excitation at 530 nm using a Fluoroskan Ascent FL (Thermo Labsystems, Beverly, Mass.).

Microarray and Analysis.

786-0 cells were plated at a density of $1 \times 10^6$ in 6-well dishes and allowed to adhere overnight. The next day, cells were pretreated for 4 hours with orthovanadate (150 uM), metavanadadate (150 uM) or the vehicle. Following pretreatment, the cells were infected with VSVΔ51 at an MOI of 0.01 or left uninfected. Twenty-four hours post infection, RNA was collected using an RNA-easy kit (Qiagen, Valencia, Calif., USA). Biological triplicates were subsequently pooled and RNA quality was measured using Agilent 2100 Bioanalyzer (Agilent Technologies) before hybridization. Hybridized to Affymetrix Human PrimeView Array was performed by The Centre for Applied Genomics, The Hospital for Sick Children, Toronto, Canada. Microarray data was processed using Transcriptome Analysis Console (TAC) 3.0 under default parameters of Gene Level Differential Expression Analysis. Fold change in gene expression was calculated for each gene in relation to uninfected, untreated control. Heatmaps of normalized expression values were generated using R package pheatmap. Volcano plots of gene expression values were generated using R. Gene ontology enrichments anlysis was evaluated using GOrilla[39] following correction for multiple hypothesis testing (Benjamini-Hochberg).

Mouse Tumor Models.

CT26 wt, CT26-LacZ, DBT, Pan02 Models.

Six-week-old female Balb/c mice (or C57BL/6 mice for the Pan02 model) obtained from Charles River Laboratories (Wilmington, Mass.) were given subcutaneous tumours by injecting $3 \times 10^5$ syngeneic CT26 wt, CT26-LacZ, or DBT (or $1 \times 10^5$ for the Pan02 model) cells suspended in 100 μl PBS. 11 days (CT26 wt, CT26-LacZ) or 13 days (DBT) or 45 days (Pan02) post implantation, tumours were treated intratumourally once with a chemical compound (dissolved in 25 μl PBS) or the vehicle as indicated. Four hours later, tumors were injected intratumorally with $1 \times 10^8$ p.f.u. (in 25 μl PBS) of the indicated virus. Tumour sizes were measured every other day using an electronic caliper. Tumour volume was calculated as=(length$^2 \times$width)/2. For survival studies, mice were culled when tumours had reached 1,500 mm$^3$. For in vivo imaging, an IVIS (Perkin Elmer, Waltham, Mass.) was used as described previously[40][41]. Quantification of the bioluminescent signal intensities in each mice was measured using Living Image® v2.50.1 software.

Dose Escalation Studies.

Six-week-old Balb/c mice were intraperitoneally administered various doses of chemical compounds dissolved in PBS (approximately 50 μL) as indicated. Mortality and body weight loss were monitored for 10-14 days. Mice were euthanized upon experimental endpoint (when drug treatment resulted in greater than 20% body weight loss).

All experiments were performed in accordance with the University of Ottawa Animal Care and Veterinary Services guidelines for animal care under the protocol OHRI-2265 and OHRI-2264.

Ex Vivo Tumor Model.

Balb/c mice were implanted with subcutaneous CT26 wt or DBT cells. Mice were sacrificed after tumors had reached at least 10 mm×10 mm in size. Tumor, lung, spleen and brain tissue were extracted from the mice, cut into 2 mm thick slices and cored into 2 mm×2 mm pieces using a punch biopsy. Each tissue core was incubated in 1 mL of Dulbecco's Modified Eagle's Medium (DMEM) supplemented with 10% fetal bovine serum, 30 mM HEPES and were incubated at 37° C. in a 5% $CO_2$ humidified incubator. Cores were treated for 4 hours with indicated concentration of chemical compound. Subsequently the cores were then infected VSVΔ51-GFP. GFP pictures were taken for each core 24 hours post infection.

Immunoblotting.

Cells were pelleted and lysed on ice for 30 minutes using in 50 mM HEPES, pH 7.4, 150 mM NaCl, 10 mM EDTA, 10 mM $Na_4P_2O_7$, 100 mM NaF, 2 mM $Na_3VO_4$, protease inhibitor cocktail (Roche) and 1% Triton X-100. Following protein determination by Bradford assay (Bio-Rad Protein Assay Solution, Mississauga, ON), 20 pg of clarified cell extract were electrophoresed on 4-15% Mini-PROTEAN® TGX™ Precast Gels (Bio-Rad) using the Mini-PROTEAN® Tetra Cell Systems (Bio-rad) and transferred on nitrocellulose membranes (Hybond-C, Bio-Rad). Blots were blocked with 5% BSA and probed with polyclonal rabbit antibodies specific for Phospho-Stat1 (Tyr701, #9171, Cell Signalling Technology, Danvers, Mass., used at 1:1,000 for 1 hour) and Stat1 (#9172, Cell Signalling Technology, Danvers, Mass., used at 1:1,000), with monoclonal rabbit or mouse antibodies specific for ß-Actin (#4970, Cell Signalling Technology, Danvers, Mass., used at 1:1,000) or α-Tubulin (sc-8035, Santa Cruz Biotechnology, Dallas, Tex., used at 1:500). Blots were then probed with a goat anti-rabbit or mouse peroxidase-conjugated antibodies (Jackson Immunoresearch Labs, West Grove, Pa.). Bands were visualized using the Supersignal West Pico Chemiluminescent substrate (Thermo Scientific Pierce, Rockford Ill.).

Quantitative Real-Time PCR.

786-0 or Ct26 wt cells were pretreated for 4 h with chemical compound or the vehicle, and were infected with VSVΔ51 at MOI 0.01 or left uninfected. 24 hours post infection, cells were collected and RNA extraction was performed using the Qiagen RNeasy kit (Qiagen). RNA quantity and purity was assessed using a NanoDrop ND-1000 spectrophotometer (Thermo Scientific, Waltham, Mass.) RNA was converted to cDNA with RevertAid H Minus First Strand cDNA Synthesis Kit (Thermo Scientific). Real-time PCR reactions were performed according to the manufacturer's protocol with the QuantiTect SYBR Green PCR kit (Qiagen) on a 7500 Fast Real-Time PCR system (Applied Biosystems, Foster City, Calif.). Gene expression relative to GAPDH or b-actin. Fold induction was calculated relative to the untreated/uninfected samples for each gene. List of qPCR primers used in this study are listed below.

| Model | Gene | Forward Primer (5'→3') | Reverse Primer (5'→3') |
|---|---|---|---|
| VSV | M | (SEQ ID NO: 1) ATACTCAGATGTGGCAGCCG | (SEQ ID NO: 2) GATCTGCCAATACCGCTGGA |
| Human | CXCL9 | (SEQ ID NO: 3) AGTGCAAGGAACCCCAGTAG | (SEQ ID NO: 4) AGGGCTTGGGGCAAATTGTT |
| | CCL8 | (SEQ ID NO: 5) TGCTGAAGCTCACACCCTTG | (SEQ ID NO: 6) GGAAACTGAATCTGGCTGAGCA |
| | CCL3 | (SEQ ID NO: 7) TTCCGTCACCTGCTCAGAAT | (SEQ ID NO: 8) CAGCAGCAAGTGATGCAGAGA |
| | IL6 | (SEQ ID NO: 9) ACCCCCAATAAATATAGGACTGGA | (SEQ ID NO: 10) GAAGGCGCTTGTGGAGAAGG |
| | CXCL8 | (SEQ ID NO: 11) ACCGGAAGGAACCATCTCAC | (SEQ ID NO: 12) GGCAAAACTGCACCTTCACAC |
| | TNF | (SEQ ID NO: 13) GCTGCACTTTGGAGTGATCG | (SEQ ID NO: 14) GAGGGTTTGCTACAACATGGG |
| | CXCL10 | (SEQ ID NO: 15) CTGAGCCTACAGCAGAGGAAC | (SEQ ID NO: 16) AGGTACTCCTTGAATGCCACTT |
| | CXCL11 | (SEQ ID NO: 17) CAGCATTTCTACTCCTTCCAAGA | (SEQ ID NO: 18) TGGGGAAGCCTTGAACAACT |
| | CCL5 | (SEQ ID NO: 19) GCAGTCGTCCACAGGTCAAG | (SEQ ID NO: 20) TCTTCTCTGGGTTGGCACAC |
| | IFNb | (SEQ ID NO: 21) CATTACCTGAAGGCCAAGGA | (SEQ ID NO: 22) CAGCATCTGCTGGTTGAAGA |
| | IFIT3 | (SEQ ID NO: 23) GCACAGACCTAACAGCACCC | (SEQ ID NO: 24) TTGGTGACCTCACTCATGATGGC |
| | GAPDH | (SEQ ID NO: 25) ACAGTCAGCCGCATCTTCTT | (SEQ ID NO: 26) GTTAAAAGCAGCCCTGGTGA |
| Mouse | CXCL9 | (SEQ ID NO: 27) CAGTGTGGAGTTCGAGGAACC | (SEQ ID NO: 28) TTTGTTGCAATTGGGGCTTGG |
| | CCL3 | (SEQ ID NO: 29) CCATATGGAGCTGACACCCC | (SEQ ID NO: 30) TCAGGAAAATGACACCTGGCT |
| | IL6 | (SEQ ID NO: 31) TCCTCTCTGCAAGAGACTTCC | (SEQ ID NO: 32) GGTCTGTTGGGAGTGGTATCC |
| | CXCL11 | (SEQ ID NO: 33) CAGCTGCTCAAGGCTTCCTTA | (SEQ ID NO: 34) CAACTTTGTCGCAGCCGTTA |
| | CCL5 | (SEQ ID NO: 35) CTGCTGCTTTGCCTACCTCT | (SEQ ID NO: 36) CGAGTGACAAACACGACTGC |
| | IFNb | (SEQ ID NO: 37) CAGTGTGGAGTTCGAGGAACC | (SEQ ID NO: 38) TTTGTTGCAATTGGGGCTTGG |
| | b-Actin | (SEQ ID NO: 39) AGGTCTCAAACATGATCTG | (SEQ ID NO: 40) AGGTATCCTGACCCTGAAG |

Elisa.

786-0 cells plated in 12-well dishes, were pretreated with drug or the vehicle for 4 h, and subsequently infected with VSVΔ51-GFP at indicated MOI or left uninfected. Cell supernatants were collected at different times post infection as indicated. IFN alpha and IFN beta quantification was performed using the Verikine Human IFN alpha or IFN beta ELISA kit (PBL Assay Science) by following the manufacturers' instructions. Absorbance values at 450 nM were measured on a Multiskan Ascent Microplate Reader (MXT Lab Systems, Vienna, Va.).

Supernatant Transfer and Filter Experiment.

786-0 cells plated in 12-well dishes, were pretreated with drug or the vehicle for 4 h, and subsequently infected with VSVΔM51-AG-GFP at an MOI of 10. This virus can infect cells but cannot exit the cell because of the lack of the viral G protein, thus preventing release of viral particles in the supernatant. 24 post infection supernatants were filtered through a 3-kDa filter (Millipore, Billerica, Mass.) before being transferred to fresh 786-0 and process for further analysis.

Tumoral T-Cell Quantification.

Mice were sacrificed and the tumors were collected at the indicated time points. The tumours were dissosiated using the mouse tumor MACS Dissociation Kit (Miltenyi Biotec, Germany). Lysis of red blood cells was performed using ACK lysis buffer. For surface staining, cells were incubated with combinations of anti-CD45-BV786 and anti-CD3-AF300 (BD Biosciences, San Jose, Calif.) for 30 minutes. Cells were then washed twice and resuspended in FACS buffer for analysis using a BD LSRFortessa flow cytometer (BD Biosciences, San Jose, Calif.).

Cytokine Array.

Supernatants from treated 786-0 cells were assayed screened with the RayBio® Cytokine Antibody Arrays—Human Cytokine Antibody Array System 3 (RayBiotech, Norcross, Ga.). The assay was performed according to the manufacturer's instructions. Data were analyzed using ImageJ and Analysis Tool for AAH-CYT-3 (RayBiotech).

Statistics.

Statistical significance was calculated using Student's T-test with Welch's correction, one-way or two way ANOVA test as indicated in the figure legends. The Gehan-Breslow-Wilcoxon was used to determine significant differences in plots for survival studies. For all studies, significance was considered to mean a P value below or equal to 0.05. Error bars represent standard error of the mean. Statistical analyses were performed using GraphPad Prism 6.0 and Excel.

REFERENCES

1. Ilkow, C. S., et al., *From scourge to cure: tumour-selective viral pathogenesis as a new strategy against cancer.* PLoS Pathog, 2014. 10(1): p. e1003836.
2. Arulanandam, R., et al., *Microtubule disruption synergizes with oncolytic virotherapy by inhibiting interferon translation and potentiating bystander killing.* Nat Commun, 2015. 6: p. 6410.
3. Forbes, N. E., R. Krishnan, and J. S. Diallo, *Pharmacological modulation of anti-tumor immunity induced by oncolytic viruses.* Front Oncol, 2014. 4: p. 191.
4. Liu, T. C. and D. Kim, *Gene therapy progress and prospects cancer: oncolytic viruses.* Gene Ther, 2008. 15(12): p. 877-84.
5. Zamarin, D., et al., *Localized oncolytic virotherapy overcomes systemic tumor resistance to immune checkpoint blockade immunotherapy.* Sci Transl Med, 2014. 6(226): p. 226ra32.
6. Russell, S. J., K. W. Peng, and J. C. Bell, *Oncolytic virotherapy.* Nat Biotechnol, 2012. 30(7): p. 658-70.
7. Coffin, R. S., *From virotherapy to oncolytic immunotherapy: where are we now?* Curr Opin Virol, 2015. 13: p. 93-100.
8. Lichty, B. D., et al., *Going viral with cancer immunotherapy.* Nat Rev Cancer, 2014. 14(8): p. 559-67.
9. Zhang, J., et al., *Maraba MG1 virus enhances natural killer cell function via conventional dendritic cells to reduce postoperative metastatic disease.* Mol Ther, 2014. 22(7): p. 1320-32.
10. Workenhe, S. T. and K. L. Mossman, *Oncolytic virotherapy and immunogenic cancer cell death: sharpening the sword for improved cancer treatment strategies.* Mol Ther, 2014. 22(2): p. 251-6.
11. Andtbacka, R. H., et al., *Talimogene Laherparepvec Improves Durable Response Rate in Patients With Advanced Melanoma.* J Clin Oncol, 2015. 33(25): p. 2780-8.
12. Lawler, S. E. and E. A. Chiocca, *Oncolytic Virus-Mediated Immunotherapy: A Combinatorial Approach for Cancer Treatment.* J Clin Oncol, 2015. 33(25): p. 2812-4.
13. Hu, J. C., et al., *A phase I study of OncoVEXGM-CSF, a second-generation oncolytic herpes simplex virus expressing granulocyte macrophage colony-stimulating factor.* Clin Cancer Res, 2006. 12(22): p. 6737-47.
14. Swarup, G., S. Cohen, and D. L. Garbers, *Inhibition of membrane phosphotyrosyl-protein phosphatase activity by vanadate.* Biochem Biophys Res Commun, 1982. 107(3): p. 1104-9.
15. Huyer, G., et al., *Mechanism of inhibition of protein-tyrosine phosphatases by vanadate and pervanadate.* J Biol Chem, 1997. 272(2): p. 843-51.
16. Chasteen, N. D., *Vanadium in biological systems: physiology and biochemistry.* 1990, Dordrecht, The Netherlands; Boston: Kluwer Academic Publishers. viii, 225 p.
17. Tracey, A. S., G. R. Willsky, and E. Takeuchi, *Vanadium: chemistry, biochemistry, pharmacology, and practical applications.* 2007, Boca Raton, Fla.: CRC Press. 250 p.
18. Bowman, B. J. and C. W. Slayman, *The effects of vanadate on the plasma membrane ATPase of Neurospora crassa.* J Biol Chem, 1979. 254(8): p. 2928-34.
19. Morita, A., et al., *Sodium orthovanadate suppresses DNA damage-induced caspase activation and apoptosis by inactivating p53.* Cell Death Differ, 2006. 13(3): p. 499-511.
20. Morita, A., et al., *Sodium orthovanadate inhibits p53-mediated apoptosis.* Cancer Res, 2010. 70(1): p. 257-65.
21. Mustelin, T., T. Vang, and N. Bottini, *Protein tyrosine phosphatases and the immune response.* Nat Rev Immunol, 2005. 5(1): p. 43-57.
22. Secrist, J. P., et al., *Stimulatory effects of the protein tyrosine phosphatase inhibitor, pervanadate, on T-cell activation events.* J Biol Chem, 1993. 268(8): p. 5886-93.
23. Watson, F. and S. W. Edwards, *Stimulation of primed neutrophils by soluble immune complexes: priming leads to enhanced intracellular Ca2+ elevations, activation of phospholipase D, and activation of the NADPH oxidase.* Biochem Biophys Res Commun, 1998. 247(3): p. 819-26.
24. Di Gioacchino, M., et al., *In vitro effects of vanadate on human immune functions.* Ann Clin Lab Sci, 2002. 32(2): p. 148-54.

25. Ehring, G. R., et al., *Vanadate induces calcium signaling, Ca2+ release-activated Ca2+ channel activation, and gene expression in T lymphocytes and RBL-2H3 mast cells via thiol oxidation.* J Immunol, 2000. 164(2): p. 679-87.
26. O'Shea, J. J., et al., *Activation of human peripheral blood T lymphocytes by pharmacological induction of protein-tyrosine phosphorylation.* Proc Natl Acad Sci USA, 1992. 89(21): p. 10306-10.
27. Heyliger, C. E., A. G. Tahiliani, and J. H. McNeill, *Effect of vanadate on elevated blood glucose and depressed cardiac performance of diabetic rats.* Science, 1985. 227(4693): p. 1474-7.
28. Thompson, K. H., et al., *Vanadium treatment of type 2 diabetes: a view to the future.* J Inorg Biochem, 2009. 103(4): p. 554-8.
29. Srivastava, A. K. and M. Z. Mehdi, *Insulino-mimetic and anti-diabetic effects of vanadium compounds.* Diabet Med, 2005. 22(1): p. 2-13.
30. Evangelou, A. M., *Vanadium in cancer treatment.* Crit Rev Oncol Hematol, 2002. 42(3): p. 249-65.
31. Bishayee, A., et al., *Vanadium in the detection, prevention and treatment of cancer: the in vivo evidence.* Cancer Lett, 2010. 294(1): p. 1-12.
32. Rehder, D., *The potentiality of vanadium in medicinal applications.* Future Med Chem, 2012. 4(14): p. 1823-37.
33. Leon, I. E., et al., *Vanadium and cancer treatment: antitumoral mechanisms of three oxidovanadium(IV) complexes on a human osteosarcoma cell line.* J Inorg Biochem, 2014. 134: p. 106-17.
34. Gordon, Y. J., et al., *Vanadate promotes reactivation and iontophoresis-induced ocular shedding of latent HSV-1 Win different host animals.* Curr Eye Res, 1990. 9(10): p. 1015-21.
35. Yamamoto, F., et al., *Enhancement of Newcastle disease virus-induced fusion of mouse L cells by sodium vanadate.* Microbiol Immunol, 1984. 28(1): p. 75-83.
36. Wang, E. and P. W. Choppin, *Effect of vanadate on intracellular distribution and function of 10-nm filaments.* Proc Natl Acad Sci USA, 1981. 78(4): p. 2363-7.
37. Stojdl, D. F., et al., *VSV strains with defects in their ability to shutdown innate immunity are potent systemic anti-cancer agents.* Cancer Cell, 2003. 4(4): p. 263-75.
38. Diallo, J. S., et al., *Propagation, purification, and in vivo testing of oncolytic vesicular stomatitis virus strains.* Methods Mol Biol, 2012. 797: p. 127-40.
39. Eden, E., et al., *GOrilla: a tool for discovery and visualization of enriched GO terms in ranked gene lists.* BMC Bioinformatics, 2009. 10: p. 48.
40. Le Boeuf, F., et al., *Synergistic interaction between oncolytic viruses augments tumor killing.* Mol Ther, 2010. 18(5): p. 888-95.
41. Doman, M. H., et al. *First-in-class small molecule potentiators of cancer virotherapy* Sci Rep. 2016. 26(6): 26786.
42. Zamarin, D. et al., *Localized oncolytic virotherapy overcomes systemic tumor resistance to immune checkpoint blockade immunotherapy.* Sci Transl Med. 2014 6(226):226.
43. Engeland, C. E., et al., *CTLA-4 and PD-L1 checkpoint blockade enhances oncolytic measles virus therapy.* Mol Ther. 2014 22(11):1949-59.
44. Cockle, J. V. et al., *Combination viroimmunotherapy with checkpoint inhibition to treat glioma, based on location-specific tumor profiling.* Neuro Oncol. 2016 April; 18(4):518-27.45. Puzanov, I., et al., *Talimogene Laherparepvec in Combination With Ipilimumab in Previously Untreated, Unresectable Stage IIIB-IV Melanoma.* J Clin Oncol. 2016 Aug. 1; 34(22):2619-26.
46. Huyer, G., et al., *Mechanism of inhibition of protein-tyrosine phosphatases by vanadate and pervanadate.* J Biol Chem. 1997 Jan. 10; 272(2):843-51.
47. Günther, T. M. et al., *Sodium orthovanadate associated with pharmacological doses of ascorbate causes an increased generation of ROS in tumor cells that inhibits proliferation and triggers apoptosis.* Biochem Biophys Res Commun. 2013 Jan. 18; 430(3):883-8.
48. Zafarullah, M., et al., *Molecular mechanisms of N-acetylcysteine actions.* Cell Mol Life Sci. 2003 January; 60(1):6-20.
49. Hebenstreit D et al., *JAK/STAT-dependent gene regulation by cytokines.* Drug News Perspect. 2005 May; 18(4):243-9.
50. Ruotsalainen J J et al., *Clonal variation in interferon response determines the outcome of oncolytic virotherapy in mouse CT26 colon carcinoma model.* Gene Ther. 2015 January; 22(1):65-75.

All references cited herein and elsewhere in the instant specification are herein incorporated by reference in their entirety.

What is claimed is:

1. A method for enhancing infection, growth, spread, or titer of an oncolytic RNA virus in a cancer or tumor cell, said method comprising:
   administering a vanadium-containing compound to the cancer or tumor cell before, after, or concurrently with infection of the cancer or tumor cell with the oncolytic RNA virus.

2. The method according to claim 1, wherein the administration of the vanadium-containing compound enhances an oncolytic activity, a cytokine-induced cell death activity, and/or a cytotoxic activity of the oncolytic RNA virus.

3. The method according to claim 1, wherein the administration of the vanadium-containing compound potentiates an immune response to, upregulates a cytokine response to, and/or enhances an immunotherapeutic activity of the oncolytic RNA virus.

4. The method according to claim 1, wherein the administration of the vanadium-containing compound to the cancer or tumor cell is for treating a tumor or cancer in a subject in need thereof.

5. The method according to claim 1, wherein the vanadium-containing compound comprises Orthovanadate, Metavanadate, Vanadium (V) oxytriethoxyde (VOx), Vanadium (IV) oxide sulphate (VS) and bismaltolato oxovanadium (IV) (BMOV), Vanadium tetra-fluoride and Vanadium tri-bromide, or a pharmaceutically acceptable salt, solvate, hydrate, reduced, or oxidized form thereof.

6. The method according to claim 1, wherein the oncolytic RNA virus comprises a reovirus, newcastle disease virus, polio virus, mumps virus, measles virus, influenza virus, Maraba virus, Rabies virus, Rotavirus, Hepatitis A virus, Rubella virus, Dengue virus, Chikungunya virus, Respiratory Syncitial Virus, LCMV, lentivirus, replicating retrovirus, or rhabdovirus, or a variant or derivative thereof.

7. The method according to claim 6, wherein the RNA virus comprises a rhabdovirus which is vesicular stomatitis virus or a derivative or variant thereof.

8. The method according to claim 1, wherein the RNA virus comprises a virus selected under specific growth conditions, subjected to one or more selection pressures, genetically modified using a recombinant technique, or any combination thereof.

9. The method according to claim 1, wherein the cell or subject is mammalian.

10. The method according to claim 9, wherein the cell or subject is human.

11. The method according to claim 1, wherein the cancer or tumor comprises lymphoblastic leukemia, myeloid leukemia, adrenocortical carcinoma, AIDS-related cancer, AIDS-related lymphoma, anal cancer, appendix cancer, astrocytoma, atypical teratoid/rhabdoid tumor, basal cell carcinoma, bile duct cancer, bladder cancer, bone cancer, osteosarcoma, malignant fibrous histiocytoma, brain stem glioma, brain tumor, cerebellar astrocytoma, cerebral astrocytoma/malignant glioma, craniopharyngioma, ependymoblastoma, medulloblastoma, pineal parenchymal tumors of intermediate differentiation, supratentorial primitive neuroectodermal tumors and pineoblastoma, visual pathway and hypothalamic glioma, spinal cord tumors, breast cancer, bronchial tumors, Burkitt lymphoma, carcinoid tumor, central nervous system lymphoma, cervical cancer, chordoma, chronic lymphocytic leukemia, chronic myelogenous leukemia, chronic myeloproliferative disorders, colon cancer, cutaneous T-Cell lymphoma, embryonal tumors, endometrial cancer, ependymoblastoma, ependymoma, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), gastrointestinal stromal cell tumor, germ cell tumors, extracranial, extragonadal, ovarian, gestational trophoblastic tumor, glioma, hairy cell leukemia, head and neck cancer, hepatocellular (Liver) cancer, histiocytosis, Langerhans cell cancer, Hodgkin lymphoma, hypopharyngeal cancer, islet cell tumors, Kaposi sarcoma, kidney cancer, laryngeal cancer, lymphocytic leukemia, hairy cell leukemia, lip and oral cavity cancer, liver cancer, non-small cell lung cancer, small cell lung cancer, Hodgkin lymphoma, non-Hodgkin lymphoma, malignant fibrous histiocytoma of bone and osteosarcoma, medulloblastoma, medulloepithelioma, melanoma, intraocular melanoma, Merkel cell carcinoma, mesothelioma, metastatic squamous neck cancer, mouth cancer, multiple endocrine neoplasia syndrome, multiple myeloma/plasma cell neoplasm, nasal cavity and paranasal sinus cancer, nasopharyngeal cancer, neuroblastoma, oral cancer, oropharyngeal cancer, ovarian cancer, pancreatic cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter cancer, transitional cell cancer, respiratory tract carcinoma, retinoblastoma, rhabdomyosarcoma, salivary gland cancer, uterine sarcoma, skin cancer, Merkel cell skin carcinoma, small intestine cancer, soft tissue sarcoma, squamous cell carcinoma, squamous neck cancer, stomach (Gastric) cancer, supratentorial primitive neuroectodermal tumors, T-Cell lymphoma, testicular cancer, throat cancer, thymoma and thymic carcinoma, thyroid cancer, trophoblastic tumor, urethral cancer, uterine cancer, endometrial cancer, uterine sarcoma, vaginal cancer, vulvar cancer, or Wilms tumor.

12. A composition comprising an oncolytic RNA virus and a vanadium-containing compound.

13. A kit comprising an oncolytic RNA virus and a vanadium-containing compound.

14. A method for producing an RNA virus comprising:
culturing a cancer or tumor cell infected with the RNA virus in an appropriate medium in the presence of a vanadium-containing compound; and
producing the RNA virus from the cancer or tumor cell via viral replication.

15. The method according to claim 1, wherein the RNA virus is VSVΔ51.

16. The method according to claim 1, wherein the vanadium-containing compound is a vanadate.

17. The method according to claim 1, wherein the vanadium-containing compound is a pharmaceutically acceptable salt of orthovanadate.

18. The composition according to claim 12, wherein the RNA virus is VSVΔ51.

19. The composition according to claim 12, wherein the vanadium-containing compound is a vanadate.

20. The kit according to claim 13, wherein the RNA virus is VSVΔ51.

21. The kit according to claim 13, wherein the vanadium-containing compound is a vanadate.

* * * * *

SEQUENCE LISTING

<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
atactcagat gtggcagccg                                            20

<210> SEQ ID NO 2
<211> LENGTH: 20
<212> TYPE: DNA
<213> ORGANISM: Artificial Sequence
<220> FEATURE:
<223> OTHER INFORMATION: primer

```
<400> SEQUENCE: 2
gatctgccaa taccgctgga                                               20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
agtgcaagga accccagtag                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
agggcttggg gcaaattgtt                                               20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tgctgaagct cacacccttg                                               20

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
ggaaactgaa tctggctgag ca                                            22

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ttccgtcacc tgctcagaat                                               20

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
cagcagcaag tgatgcagag a                                             21

<210> SEQ ID NO 9
```

```
<211> LENGTH: 24
<212> TYPE: DNA
<213> ORGANISM: Artificial Sequence
<220> FEATURE:
<223> OTHER INFORMATION: primer

<400> SEQUENCE: 9
acccccaata aatataggac tgga                                           24

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gaaggcgctt gtggagaagg                                                20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
accggaagga accatctcac                                                20

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
ggcaaaactg caccttcaca c                                              21

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gctgcacttt ggagtgatcg                                                20

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
gagggtttgc tacaacatgg g                                              21

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
```

```
ctgagcctac agcagaggaa c                                              21

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
aggtactcct tgaatgccac tt                                             22

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
cagcatttct actccttcca aga                                            23

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
tggggaagcc ttgaacaact                                                20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gcagtcgtcc acaggtcaag                                                20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tcttctctgg gttggcacac                                                20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
gcacagacct aacagcaccc                                                20

<210> SEQ ID NO 22
<211> LENGTH: 23
<212> TYPE: DNA
```

```
<213> ORGANISM: Artificial Sequence
<220> FEATURE:
<223> OTHER INFORMATION: primer

<400> SEQUENCE: 22
ttggtgacct cactcatgat ggc                                            23

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
gcacagacct aacagcaccc                                                20

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
ttggtgacct cactcatgat ggc                                            23

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
acagtcagcc gcatcttctt                                                20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
gttaaaagca gccctggtga                                                20

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
cagtgtggag ttcgaggaac c                                              21

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
tttgttgcaa ttggggcttg g                                              21
```

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
ccatatggag ctgacacccc                                               20

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
tcaggaaaat gacacctggc t                                             21

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
tcctctctgc aagagacttc c                                             21

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
ggtctgttgg gagtggtatc c                                             21

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
cagctgctca aggcttcctt a                                             21

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
caactttgtc gcagccgtta                                               20

<210> SEQ ID NO 35
<211> LENGTH: 20
<212> TYPE: DNA
<213> ORGANISM: Artificial Sequence
<220> FEATURE:

```
<223> OTHER INFORMATION: primer

<400> SEQUENCE: 35
ctgctgcttt gcctacctct                                           20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
cgagtgacaa acacgactgc                                           20

<210> SEQ ID NO 37
<211> LENGTH: 21
<212> TYPE: DNA
<213> ORGANISM: Artificial Sequence
<220> FEATURE:
<223> OTHER INFORMATION: primer

<400> SEQUENCE: 37
cagtgtggag ttcgaggaac c                                         21

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
tttgttgcaa ttggggcttg g                                         21

<210> SEQ ID NO 39
<211> LENGTH: 19
<212> TYPE: DNA
<213> ORGANISM: Artificial Sequence
<220> FEATURE:
<223> OTHER INFORMATION: primer

<400> SEQUENCE: 39
aggtctcaaa catgatctg                                            19

<210> SEQ ID NO 40
<211> LENGTH: 19
<212> TYPE: DNA
<213> ORGANISM: Artificial Sequence
<220> FEATURE:
<223> OTHER INFORMATION: primer

<400> SEQUENCE: 40
aggtatcctg accctgaag                                            19
```